United States Patent
Lebedev et al.

(10) Patent No.: US 8,133,669 B2
(45) Date of Patent: Mar. 13, 2012

(54) CHEMICALLY MODIFIED NUCLEOSIDE 5'-TRIPHOSPHATES FOR THERMALLY INITIATED AMPLIFICATION OF NUCLEIC ACID

(75) Inventors: Alexandre Lebedev, San Diego, CA (US); Inna Koukhareva, San Diego, CA (US)

(73) Assignee: Trilink Biotechnologies, San Diego, CA (US)

( * ) Notice: Subject to any disclaimer, the term of this patent is extended or adjusted under 35 U.S.C. 154(b) by 0 days.

(21) Appl. No.: 12/470,449

(22) Filed: May 21, 2009

(65) Prior Publication Data

US 2010/0003724 A1  Jan. 7, 2010

Related U.S. Application Data

(60) Provisional application No. 61/056,324, filed on May 27, 2008.

(51) Int. Cl.
- *C12Q 1/68* (2006.01)
- *C12P 19/34* (2006.01)
- *G01N 15/06* (2006.01)
- *B01L 3/00* (2006.01)
- *C07G 3/00* (2006.01)
- *C07H 21/04* (2006.01)

(52) U.S. Cl. .......... 435/6; 435/91.1; 422/430; 422/68.1; 536/4.1; 536/23.1; 536/24.33; 536/26.6

(58) Field of Classification Search .............. 435/6, 91.1, 435/1, 91.2; 422/430, 68.1; 536/4.1, 23.1, 536/24.33, 26.6
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 5,302,509 A | 4/1994 | Cheeseman |
| 5,763,594 A | 6/1998 | Hiatt et al. |
| 5,773,258 A | 6/1998 | Birch et al. |
| 5,808,045 A | 9/1998 | Hiatt et al. |
| 5,872,244 A | 2/1999 | Hiatt et al. |
| 5,990,300 A | 11/1999 | Hiatt et al. |
| 6,232,465 B1 | 5/2001 | Hiatt et al. |
| 6,242,193 B1 | 6/2001 | Anazawa et al. |
| 6,509,157 B1 | 1/2003 | Martinez |
| 6,664,079 B2 | 12/2003 | Ju et al. |
| 6,762,298 B2 | 7/2004 | Beaucage et al. |

(Continued)

FOREIGN PATENT DOCUMENTS

EP  1218391  4/2007

(Continued)

OTHER PUBLICATIONS

Ailenberg et al., Controlled Hot Start and Improved Specificity in Carrying Out PCR Utilizing Touch-Up and Loop Incorporated Primers (TULIPS) *BioTechniques* 29(5):1018-1024 (2000).

(Continued)

*Primary Examiner* — Jezia Riley
(74) *Attorney, Agent, or Firm* — Foley & Lardner LLP; Stephen E. Reiter

(57) ABSTRACT

Provided herein are methods and compositions for nucleic acid replication. These methods involve the use of 3'-substituted nucleoside 5'-triphosphates or 3'-substituted terminated primers in nucleic acid replication reactions. In certain aspects, the methods are accomplished by use of 3'-substituted NTPs and/or 3'-substituted terminated primers which provide utility in nucleic acid replication. In preferred embodiments, the NTPs and/or primers are substituted at the 3'-position with particular heat labile chemical groups such as ethers, esters or carbonate esters.

63 Claims, 8 Drawing Sheets

Two possible mechanisms of Hot Start PCR with 3'-substituted NTPs

U.S. PATENT DOCUMENTS

| | | | |
|---|---|---|---|
| 7,279,563 | B2 | 10/2007 | Kwiatkowski |
| 7,355,037 | B2 | 4/2008 | Beaucage et al. |
| 7,414,116 | B2 | 8/2008 | Milton et al. |
| 2003/0162199 | A1 | 8/2003 | Bonner |
| 2007/0281308 | A1 | 12/2007 | Zon et al. |

FOREIGN PATENT DOCUMENTS

| | | |
|---|---|---|
| WO | WO 91/06678 | 5/1991 |
| WO | WO 92/10587 | 6/1992 |
| WO | WO 02/088387 | 11/2002 |
| WO | WO 2008/016562 | 2/2008 |
| WO | WO 2008/037568 | 4/2008 |

OTHER PUBLICATIONS

Allawi et al., Invader Plus Method Detects Herpes Simplex Virus in Cerebrospinal Fluid and Simultaneously Differentiates Types I and 2, *J Clin Microbiol* 44(9): 3443-3447 (2006).

Ausubel et al., Chapter 7, DNA Sequencing, *Current Protocols in Molecular Biology*, 7.0.1-7.0.15 (1999).

Bi et al., Design and Synthesis of a Chemically Cleavable Fluorescent Nucleotide, 3'-O-Allyl-dGTP-allyl-Bodipy-FL-510, as a Reversible Terminator for DNA Sequencing by Synthesis, *J. Amer. Chem. Soc.*, 128(8): 2542-2543 (2006).

Budowle et al., Building Microbial Forensics as a Response to Bioterrorism, *Science*, 301: 1852-1853 (2003).

Burgess and Cook, Synthesis of Nucleoside Triphosphates, *Chem. Rev.*, 100: 2047-2059 (2000).

Bustin et al., Pitfalls of Quantitative Real-Time Reverse-Transcription Polymerase Chain Reaction, *J. of Biomolecular Techniques*, 15: 155-166 (2004).

Chen, et al., Fluorescence Polarization in Homogeneous Nucleic Acid Analysis, *Genome Res.*, 9: 492-498 (1999).

Chou, et al., Prevention of pre-PCR mis-priming and primer dimerization improves low-copy-number amplifications, *Nucleic Acids Res.* 20: 1717-1723 (1992).

Cieślak, et al., Thermolytic Properties of a 3-(2-Pyridyl)-1-propyl and 2[N-Methyl-N-(2-pyridyl)] aminoethyl Phosphate/Thiophosphate Protecting Groups in Solid-Phase Synthesis of Oligodeoxyribunonucleotides, *J. Org. Chem.*, 68: 10123-10129 (2003).

Cieślak et al., Thermolytic 4-Methylthio-1-butyl Group for Phosphate/Thiophosphate Protection in Solid-Phase Synthesis of DNA Oligonucleotides, *J. Org. Chem.*, 69: 2509-2515 (2004).

Cozza et al., TAMGeS: a Three-Array Method for Genotyping of SNPs by a dual-colour approach, *BMC Genomics*, 8: 1-14 (2007).

Crey-Desbiolles et. al., Hybridization properties and enzymatic replication of oligonucleotides containing the photocleavable 7-nitroindole base analog, *Nucleic Acids Res.* 33: 1532-1543 (2005).

Dahiya et al., A novel p53 mutation at codon 132 (AAG→AGG) in human renal cancer, *Biochemistry and Molecular Biology International*, 44: 407-415 (1998).

Dang et al., Oligonucleotide Inhibitors of *Taq* DNA Polymerase Facilitate Detection of Low Copy Number Targets by PCR, *J. Mol. Biol.*, 264: 268-278 (1996).

De la Vega et al., Assessment of two flexible and compatible SNP genotyping platforms: TaqMan® SNP Genotyping Assays and the SNPlex™ Genotyping System, *Mutat Res,*. 573: 111-135 (2005).

Dunbar, Applications of Luminex® xMAP™ technology for rapid, high-throughput multiplexed nucleic acid detection, *Clin Chim Acta*, 363: 71-82 (2006).

Easton et al., Genome-wide association study identifies novel breast cancer susceptibility loci, *Nature*, 447: 1087-1093 (2007).

Elnifro et al., Multiplex PCR : Optimization and Application in Diagnostic Virology, *Clin. Microbiol. Rev.*, 13: 559-570 (2000).

Grajkowski, The 2-N-Formyl-N-methyl)aminoethyl Group as a Potential Phosphate/Thiophosphate Protecting Group in Solid-Phase Oligodeoxyribonucleotide Synthesis, *Org. Lett.*, 3: 1287-1290 (2001).

Hafner et al., Isothermal Amplification and Multimerization of DNA by *Bst* DNA Polymerase, *Biotechniques*, 30(4): 852-867 (2001).

Hill et. al., Polymerase recognition of synthetic oligodeoxyribonucleotides incorporating degenerate pyrimidine and purine bases, *Proc Natl Acad Sci U S A*, 95: 4258-4263 (1998).

Jeng et al., The Use of Aryl Azido ATP Analogs as Photoaffinity Labels for Myosin ATPase, *J. Supramol. Struct.*, 3: 448-468 (1975).

Kincaid et. al., Exploration of factors driving incorporation of unnatural dNTPS into DNA by Klenow fragment (DNA polymerase 1) and DNA polymerase α, *Nucleic Acids Res*. 33: 2620-2628 (2005).

Kolmodin et al., Polymerase Chain Reaction: Basic Principles and routing practice. Chapter 73 in *The Nucleic Acid Protocols Handbook*, Totowa, N.J.: Humana Press, Inc., 569-580 (2000).

Koukhareva et al., Heat Activatable 3'-modified dNTPs : Synthesis and Application for Hot Start PCR, *Nucleic Acids Symposium*, 52: 259-260 (2008).

Koukhareva et al., A New Approach to Improved Hot Start PCR : Nucleoside 5'-Triphosphates with Thermolabile 3'-Protecting Group, *Collection Symposium Series*, 10: 259-263 (2008).

Kwok, Methods for Genotyping Single Nucleotide Polymorphisms, *Annu Rev Genomics Hum Genet*, 2: 235-258 (2001).

Langaee et al., Genetic variation analyses by Pyrosequencing, *Mutat Res*, 573(1-2): 96-102 (2005).

Lebedev et al., The chirality problem in P-substituted oligonucleotides, *Perspect. Drug Discov. Des.*, 4:17-40 (1996).

Lekanne Deprez et al., Sensitivity and accuracy of quantitative real-time polymerase chain reaction using SYBR green I depends on cDNA synthesis conditions, *Analytical Biochem.*, 307: 63-69 (2002).

Loakes D., Survey and Summary: The applications of universal DNA analogues, *Nucleic Acids Res.* 29: 2437-2447 (2001).

Ludwig et al., Rapid and Efficient Synthesis of Nucleoside 5'-O-(1-Thiotriphosphates), 5'-Triphosphates and 2',3'-Cyclophosphorothioates Using 2- chloro-4H-1,3,2-benzodioxaphosphorin-4-one, *J. Org. Chem.*, 54: 631-635 (1989).

Lunardi et. al., Exploration of Adenosine 5'-Diphosphate-Adenosine 5'-Triphosphate Binding Sites of *Escherichia coli* Adenosine 5'-Triphosphatase with Arylazido Adenine Nucleotides, *Biochemistry*, 20: 473-480 (1981).

Markoulatos et al., Multiplex Polymerase Chain Reaction: A Practical Approach, *J. of Clin. Laboratory Analysis*, 16: 47-51 (2002).

Matsuzakil et al., Parallel Genotyping of Over 10,000 SNPs Using a One-Primer Assay on a High Density Oligonucleotide Array, *Genome Res*, 14: 414-425 (2004).

Meng, et al, Design and Synthesis of a Photocleavable Fluroescent Nucleotide 3'-O-Allyl-dGTP-PC-Bodipy-FL-510 as a Reversible Terminator for DNA Sequencing by Synthesis, *J. Org. Chem.*, 71: 3248-3252 (2006).

Metzker, et al., Termination of DNA synthesis by novel 3'-modified-deoxyribonucleoside 5'-triphosphates, *Nucleic Acids Res.*, 22: 4259-4267 (1994).

Metzker, M., Emerging technologies in DNA sequencing, *Genome Research* 15: 1767-1776 (2005).

Mizuguchi et al., Characterization and Application to Hot Start PCR of Neutralizing Monoclonal Antibodies against KOD DNA Polymerase, *J. Biochem.* (Tokyo), 126: 762-768 (1999).

Moretti et al., Enhancement of PCR Amplification Yield and Specificity Using AmpliTaq Gold™ DNA Polymerase, *BioTechniques*, 25: 716-722 (1998).

Mueller et al., JumpStart™ PCR—Hot Start PCR Enzymes and Mixes, *LifeScience Quarterly*, 2: 2-5 (2001).

Preparata, et al., DNA Sequencing by Hybridization Using Semi-Degenerate Bases, *J. Comput. Biol.* 11: 753-765 (2004).

Puskas et al., Reduction of Misprinting in Amplification Reactions with Restricted PCR, *Genome Research*, 5: 309-311 (1995).

Ramakers et al., Assumption-free analysis of quantitative real-time polymerase chain reaction (PCR) data, *Neurosci Lett*. 339: 62-66 (2003).

Saiki, Amplification of Genomic DNA, Chapter 2 in *PCR Protocols: A Guide to Methods and Applications*. San Diego: Academic Press, Inc., 13-20 (1990).

Saldanha et al., A Sensitive PCR Method for Detecting HCV RNA in Plasma Pools, Blood Products, and Single Donations, *J. Medical Virol.*, 43: 72-76 (1994).

Sato et al., HLA typing of aortic tissues from unidentified bodies using hot start polymerase chain reaction-sequence specific primers, *Legal Medicine*, 5: S191-S193 (2003).

Schafer et al., Energy Transfer Inhibition in Photosynthesis by 3'-aryl-$N_3$-ADP, AN ADP Analog, *FEBS Lett.*, 87(2): 318-322 (1978).

Shen et al., High-throughput SNP genotyping on universal bead arrays, *Mutat Res*, 573: 70-82 (2005).

Stec et al., Stereocontrolled Synthesis of Oligo(nucleoside phosphorothioate)s, *Chem. Int. Ed. Engl.*, 33: 709-722 (1994).

Tanzer et al., A Hot Start Reverse Transcription-Polymerase Chain Reaction Protocol That Initiates Multiple Analyses Simultaneously, *Anal. Biochem.*, 273: 307-310 (1999).

Waldner et al., Hydrophobic Effects in Duplexes with Modified Oligonucleotide Backbones and RNA, *Bioorg. & Med. Chem. Letters* 6(19): 2363-2366 (1996).

Wharam et al., Specific detection of DNA and RNA targets using a novel isothermal nucleic acid amplification assay based on the formation of a three-way junction structure, *Nucleic Acids Res*, 29(11): 2-8 (2001).

Wilk et al., The 4-oxopentyl group as a labile phosphate/thiophosphate protecting group for synthetic oligodeoxyribonucleotides, *Tetrahedron Lett.*, 42: 5635-5639 (2001).

Wilk et al., The 3'-(*N-tert*-Butylcarboxamido)-1-propyl Group as an Attractive Phosphate/Thiophosphate Protecting Group for Solid-Phase Oligodeoxyribonucleotide Synthesis, *J. Org. Chem.*, 67: 6430-6438 (2002).

Zhang et al., Differential priming of RNA templates during cDNA synthesis markedly affects both accuracy and reproducibility of quantitative competitive reverse-transcriptase PCR, *Biochem. J.*, 337: 231-241 (1999).

International Search Report for PCT Patent Application No. PCT/US2009/044910 dated Sep. 1, 2009.

Axelrod, et al, Nucleic Acid Research, (1978), 5:3549-3583.

International Search Report dated Sep. 1, 2009 in application PCT/US2009/044910.

Kutateladze, et al, FEBS Letters, (1986), 207:205-212.

Hot Start activation of 3'-substituted NTP (A) or terminated primer (B)

A)

B)

X = thermolabile 3'-substitution group

Agarose gel analysis of PCR mixtures

Each PCR sample contains mixture of dTTP-3'-OX, dATP, dCTP and dGTP

Lambda DNA: Ratio of Amplicon to off-target products

CHEMICALLY MODIFIED NUCLEOSIDE 5'-TRIPHOSPHATES FOR THERMALLY INITIATED AMPLIFICATION OF NUCLEIC ACID

CROSS-REFERENCE TO RELATED APPLICATION

This patent application claims priority to U.S. Provisional Patent Application No. 61/056,324, entitled "Chemically Modified Nucleoside 5'-Triphosphates for Thermally Initiated Amplification of Nucleic Acid," filed May 27, 2008 which is hereby incorporated by reference in its entirety for all purposes.

STATEMENT OF GOVERNMENT SUPPORT

The United States Government has certain rights in this invention pursuant to Grant No. GM079836 awarded by the National Institute for General Medical Science.

FIELD OF THE INVENTION

Provided herein are methods and compositions for replication of nucleic acids. In certain particular aspects and embodiments, the methods and compositions are for hot start nucleic acid amplification.

BACKGROUND OF THE INVENTION

The following description is provided to assist the understanding of the reader. None of the information provided or references cited is admitted to be prior art in the present invention.

Poymerase Chain Reaction (PCR) is likely the most widely used method in modern molecular biology and biotechnology, and is rapidly being applied to genetic testing, diagnostics, forensics and biodefense. Kolmodin, L. A. et al., Nucleic Acid Protocols Handbook, 569-580 (Rapley, R. ed., Humana Press 2000); Budowle, B., et al., 301 Science, 1852-1853 (2003); Sato, Y. et al., 5 (Suppl. 1) Legal Medicine, S191-S193 (2003); Saldanha. J., et al., 43 J. Medical Virol., 72-76 (1994); Dahiya. R., et al., 44 Biochemistry and Molecular Biology International, 407-415 (1998); and Elnifro, E. M., et al., 13 Clin. Microbiol. Rev., 559-570 (2000). PCR is described in U.S. Pat. Nos. 4,683,195 and 4,683,202. In each cycle of the PCR amplification process there are typically several steps. The double-stranded DNA target sequence is first thermally denatured at elevated temperatures (~95° C.). The first occurrence of denaturation is oligonucleotide primer to each strand at lower temperatures (~60° C.). These forward and reverse oriented oligonucleotide primers are then each extended from their 3'-termini at an elevated temperature (~70° C.) by a thermally stable, magnesium ion-dependent, DNA polymerase which incorporates 2'-deoxyribonucleoside 5'-triphosphates (dNTPs) and generates pyrophosphate (PPi).

The utility of PCR is driven by its ability to rapidly provide target amplifications of ~$10^6$-fold as well as high specificity, which depends in part on the specificity of oligonucleotide primer hybridization. Oligonucleotide primer sequences and length are therefore designed to hybridize to only the intended target sequence, at the temperatures used for annealing. However, PCR amplification reactions are typically prepared over a period of minutes or hours at ambient room temperatures which are well below the temperature range needed to ensure specificity of oligonucleotide primer hybridization. Under such low stringency sample preparation conditions and following an initial pre-PCR denaturation step, oligonucleotide primers may bind non-specifically to other sequences and potentially initiate synthesis of undesired extension products, which can be amplified along with the target sequence. Amplification of non-specific target sequences having partial complementarity to the primers, so called "mis-priming," can compete with amplification of desired target sequences, and can significantly decrease efficiency of amplification of the desired sequence, especially for low-copy number targets (Chou, Q., et al., 20 Nucleic Acids Res. 1717-1723 (1992)).

Formation of "primer dimers" is another problematic form of non-specific hybridization, which, according to Chou, Q., et al., results from amplification of two oligonucleotide primers extended across one another's sequence without significant intervening sequence. These investigations further noted that primer dimers may undergo amplified oligomerization during PCR to create a complex mixture of oligonucleotide primer artifacts, the quantity and quality of which often varies inversely with the yield of specific PCR product in low copy number amplifications.

While the aforementioned problems due to mis-priming and primer dimer formation can be encountered in all applications of PCR, these issues can be particularly challenging for high-sensitivity analytical PCR schemes, such as those used for detection of blood-borne infectious agents (Saldanha, J., et al.; Elnifro, E. M., et al.), biohazardous microbes (Budowle, B., et al.), defective or cancerous genes (Dahiya, R., et al.), and forensics (Budowle, B., et al.; Y. Sato, et al.). In addition, there is a much greater chance for formation of spurious amplification products in multiplex PCR. Markoulatos, P., et al., 16 J. of Clin. Laboratory Analysis, 47-51 (2002). In reverse transcriptase PCR (RT-PCR), the most sensitive means for detection of a target RNA sequence is to use a gene-specific oligonucleotide primer in the RT step. Zhang, J., et al., 337 Biochem. J., 231-241 (1999); Lekanne Deprez, R. H., et al., 307 Analytical Biochem., 63-69 (2002); Bustin, S, A., et al., 15 J. of Biomolecular Techniques, 155-166 (2004). In view of the importance of these high-sensitivity applications requiring high specificity to avoid serious, adverse consequences of "false negatives" and "false positives," it is critical to have reagents and protocols which provide assays that are functionally free of artifacts due to mis-priming and primer dimer formation.

A number of general strategies have been investigated for reducing non-specific amplification based on the so-called "hot start" process which aims at impairing undesired amplification due to mis-priming and oligonucleotide primer dimer formation under low-stringency conditions e.g., at room temperature during sample preparation and following an initial pre-PCR denaturation step. Amplification subsequently begins when the reaction mixture reaches high-stringency, i.e., "hot" temperatures to "start" polymerase-mediated extension of oligonucleotide primers hybridized only to target sequences. Thus temperature triggers enzymatic extension of oligonucleotide primers only at elevated temperatures when the stringency of primer/target hybridization conditions is optimal for specificity.

These general strategies for "hot start" include the use of (1) temperature-sensitive materials, such as waxes as barriers or sequestrants to control mixing of the reagents (Chou, Q., et al.; Tanzer, L. R., et al., 273 Analytical Biochem., 307-310 (1999)); (2) oligonucleotide aptamers (Dang, C., et al., 264 J. Mol. Biol., 268-278 (1996)) or antibodies (Eastlund, E., et al., 2 LifeScience Quarterly, 2-5 (2001); Mizuguchi, H., et al., 126 J. Biochem. (Tokyo), 762-768 (1999)) that inhibit the function of DNA polymerases; (3) use of a second thermostable enzyme, such as pyrophosphatase (Clark, D. R., et al., International Patent Application No. WO 2002088387) to remove suppression by added pyrophosphate (PPi); (4) chemically modified polymerases with hydrolytically reversible reagents, such as citraconic acid-modified lysine (Birch, D. E., et al., U.S. Pat. No. 5,773,258) in AmpliTaq Gold (Moretti, T., et al., 25 BioTechniques, 716-722 (1998); Saldanha, J., et al.); (5) oligonucleotide primer sequence constructs that disfavor low-temperature mis-priming, such as competitor sequences (Puskas, L. G., et al., 5 Genome Research, 309-311 (1995)) or "touch-up and loop-incorporated oligonucleotide primers" (TULIPS-PCR) (Ailenberg, M. et al., 29(5) BioTechniques, 1018-1023 (2000)); and (6) chemically modified primer containing phosphotriester internucleotide linkage(s) near the 3'-end of the primer (i.e., phosphotriester primers) (Zon, G., et al., U.S. Patent Appl. No. 20070281308 (2007)).

SUMMARY OF THE INVENTION

Provided herein are methods and compositions for nucleic acid replication. These methods involve the use of nucleoside 5'-triphosphates (NTPs), oligonucleotide primers and enzyme in temperature dependent nucleic acid template dependent polymerization reactions. In certain aspects, the methods are accomplished by use of modified NTPs, which provide utility in nucleic acid replication. In particularly preferred embodiments, the modified NTPs have a 3'-substitution, i.e., a group other than a hydroxyl group at the terminal 3'-position. The use of such NTPs in methods can be for nucleic acid amplification, in particular hot start amplification. In certain embodiments the 3'-substitution of the NTP impairs polymerase mediated oligonucleotide primer extension prior to the initial incubation period at an elevated temperature of nucleic acid replication, such as in the initial denaturation step of PCR. In certain aspects and embodiments, provided are methods and compositions in which the 3'-substitution group of the NTPs as disclosed herein converts to an open 3'-hydroxyl (3'-OH) group during or after the initial denaturation step of the nucleic acid replication and, where applicable, during subsequent replication cycles.

In some aspects, methods are provided in which nucleic acid (e.g., DNA) is replicated where at least one modified NTP is added to a replication reaction that has a 3'-substitution as disclosed herein. Preferably the 3-'-substitution of the at least one modified NTP does not support (e.g., in some embodiments, preferably a nucleic acid polymerase is capable of incorporating and/or extending unsubstituted or natural NTPs and is not capable of incorporating and/or extending 3'-substituted NTPs), impairs or prevents polymerase mediated oligonucleotide primer extension prior to the initial incubation period, i.e., the initial denaturation temperature, of nucleic acid replication such as in 80-105° C. for PCR and 42-70° C. for RT-PCR. In certain preferred embodiments, the 3'-substitution impairs nucleic acid polymerase mediated incorporation of a 3'-substituted NTP with an oligonucleotide primer thus preventing 3'-extension of the primer. This type of 3'-substituted NTP represents a "non substrate NTP." In other certain preferred embodiments, a 3'-substituted NTP can incorporate onto the 3'-end of an oligonucleotide primer and the 3'-substitution group then impairs any further nucleic acid polymerase mediated extension of the oligonucleotide primer. This type of 3'-substituted NTP represents a "terminating NTP."

Thermolabile protecting groups suitable for modification groups of the compositions and methods described herein (e.g., 3'-substitutions and internucleotide linkages) have been described in literature for use in the oligonucleotide synthesis process. See, e.g., Grajkowski, et al., 3 Org. Lett., 1287-1290 (2001); Wilk. A., et al., 42 Tetrahedron Lett., 5635-5439 (2001); Wilk, A., et al., 67 J. Org. Chem., 6430-6438 (2002); Cieslak, J. et al., 68 J. Org. Chem., 10123-10129 (2003); Cieslak, J. et al., 69 J. Org. Chem., 2509-2515 (2004); Beaucage,. et al., U.S. Patent Appl. No. 20050020827 (2005); and Beaucage, et al., U.S. Pat. No. 6,762,298.

Several applications based on the use of 3'-substituted NTPs and nucleoside diphosphates (NDPs) have been developed. Jeng et al., 3 J. Supramol. Struct., 448-468 (1975) described synthesis of 3'-arylazido ATP analogs and their use as photoaffinity labels for myosin ATPase. Similar compounds were prepared and tested in other ATPase systems (Schafer, et. al., 87 FEBS Lett., 318-322 (1978): Lunardi, et. al., 20 Biochemistry, 473-480 (1981)). Hiatt et al., U.S. Pat. No. 6,232,465 and referenced patents describes 3'-protected nucleoside 5'-triphosphates for enzyme catalyzed template-independent creation of phosphodiester bonds for use in oligonucleotide synthesis. After formation of the phosphodiester bond the 3'-protecting group of the incorporated nucleotide can be chemically removed and synthesis of the oligonucleotide can be continued. Another use of 3'-substituted NTPs is sequencing by step-wise synthesis. Cheeseman, U.S. Pat. No. 5,302,509, describes 3'-modified NTPs containing a removable fluorescent label for sequencing polynucleotides. Metzker, et al., 22 Nucleic Acids Res. 4259-4267 (1994) describes synthesis of modified NTPs with a UV-removable 3'-protecting group as a key component for development of a new sequencing strategy. A similar approach includes the use of dye labeled NTPs containing 3'-O-allyl and 3'-O-methoxyethyl protecting groups, as developed by Ju. et al. U.S. Pat. No. 6,664,079; Meng, Q., et al, 78 J. Org. Chem., 3248-3252 (2006); and Bi. L., et al., 125 J. Amer. Chem. Soc., 2542-2543 (2006)). The 3'-O-allyl protecting group is removable by palladium catalyst in neutral aqueous solution at elevated temperature. Other patents also describe synthesis and use of 3'-substituted dNTPs with a removable 3'-substitution group. For example, the 3'-blocking group can be removed by adding hydrochloric acid to pH 2 (e.g., Tsien, R. Y, WO 91/06678); or by adding a reducing agent such as mercaptoethanol (e.g., Kwiatkowski, M., U.S. Pat. No. 7,279, 563); or by the addition of tris-(2-carboxyethyl)phosphine (e.g., Milton, J., et al, U.S. Pat. No. 7,414,116). Certain 3'-substitution groups can be removed by UV irradiation (e.g., Dower, et al., WO 92/10587). Removable 3'-substitution groups have been described for oligonucleotides (e.g. Bi, W., WO 08/016562 (A2)).

In certain aspects, provided are compositions (i.e., 3'-substituted NTPs) that include the chemical formulas depicted in Formulas IA and IB further described herein. In related aspects, provided are methods in which DNA is replicated using compositions that include the chemical formulas depicted in Formulas IA and IB further described herein; and/or using oligonucleotides that include at least one monomer unit derived from the incorporation of a 3'-substituted NTP that includes chemical formulas depicted in Formulas IA and IB.

As used herein, the term "non substrate NTP" refers to a 3'-substituted NTP that has a 3'-substitution which is unable to incorporate into an oligonucleotide primer (FIG. 1A). A non substrate NTP of the methods and compositions provided herein has two states. The non substrate NTP is in an inactive state due to the presence of a 3'-substitution group and is not a substrate for nucleic acid polymerase (FIG. 1A). Upon reaching an initial denaturation temperature, often 95° C., an inactive non substrate NTP can be converted to an active state by thermally induced intra- and/or intermolecular conversion of the 3'-substitution group or by other chemical reaction that results in the conversion of the 3'-substitution group to an unmodified or open 3'-OH group. This active state of the non substrate NTP is the corresponding natural or 3'-unsubstituted NTP or functional derivative thereof, which possesses an unsubstituted or open 3'-OH group, and can be a substrate for nucleic acid polymerase and supports nucleic acid replication (FIGS. 1 and 2). In particularly preferred embodiments, partial or complete conversion of the 3'-substitution group occurs during incubation at approximately 95° C. for approximately 1-120 minutes. In some embodiments, 3'-substituted NTPs as disclosed herein may be used in conjunction with one or more other hot start methods and compositions as known in the art such as use of temperature-sensitive materials, such as waxes as barriers or sequestrants to control mixing of the reagents; oligonucleotide aptamers or antibodies that inhibit the function of DNA polymerases, use of a second thermostable enzyme, such as pyrophosphatase to remove suppression by added pyrophosphate (PPi); chemically modified polymerases with hydrolytically reversible reagents, such as citraconic acid-modified lysine; oligonucleotide primer sequence constructs that disfavor low-temperature mis-priming, such as competitor sequences; and chemically modified primer containing phosphotriester internucleotide linkage(s) near the 3'-end of the primer (i.e., phosphotriester primers)). In preferred embodiments, conversion of the 3'-substitution group occurs with respect to temperature and does not require enzymes, additional chemicals, or modified polymerization reaction conditions other than those normally used in replication reactions with standard dNTPs. Different 3'-substitution groups for nucleosides and nucleotides of the compositions and methods provided herein are described, for example, in Greene, T. W. and Wuts, P. G. M., Protective groups in organic synthesis, John Wiley & Sons, Inc. (1999).

As used herein, the term "terminating NTP" refers to a 3'-substituted NTP which is capable of being incorporated onto the 3'-end of an oligonucleotide primer (FIG. 1B). As a result of incorporation of the terminating NTP a terminated primer is formed and further elongation of the primer is prevented. A terminating NTP has two states and in both states is a substrate for nucleic acid polymerase. The terminating NTP is in a terminating state due to the presence of a 3'-substitution group. Incorporation of a terminating NTP onto the 3'-end of a primer results in a formation of (N+1) elongated terminated primer and prevents further extension of the primer (FIG. 1B). At elevated temperatures, such as 95° C., the terminating NTP can transform to an active state by thermally induced intra- and/or intermolecular removal of the 3'-substitution group or by other chemical reaction that results in the conversion of the 3'-substitution group to an unmodified or open 3'-OH group (FIG. 1B). In this state, the terminating NTP is converted to the corresponding natural or unsubstituted NTP or functional derivative thereof, which possesses an unsubstituted or open 3'-OH and can be a substrate for nucleic acid polymerase. In particularly preferred embodiments partial or complete conversion of the 3'-substitution group occurs during incubation at approximately 95° C. for approximately 1-120 minutes. In preferred embodiments, conversion of the 3'-substitution group occurs with respect to temperature and does not require enzymes, additional chemicals, or modified polymerization reaction conditions other than those normally used in replication reactions with standard dNTPs. Different 3'-substitution groups for nucleosides and nucleotides of the compositions and methods provided herein are described, for example, in Greene, T. W., et al.

In the event that a nucleic acid polymerase incorporates a terminating NTP onto the 3'-end of a primer, the terminating NTP becomes a part of a (N+1) elongated primer which is referred to as a "terminated primer." The terminated primer cannot be further elongated and stays in a "terminated state" due to the presence of a 3'-substitution group at its terminus, at the last 3'-nucleotide unit originated from the incorporated terminating NTP, until a high temperature is reached, often 95° C. This terminating state for a terminated primer is equivalent to the inactive state defined herein for a non substrate NTP. In a preferred embodiment, a terminated primer includes an additional modification, for example, a modified nucleoside residue with modified sugar, base, (5'-3')-internucleotide linkage, or any combination thereof in addition to containing a 3'-substitution group. More preferably a terminated primer contains a thermally labile 3'-substitution group. Upon reaching a high temperature (e.g., the initial denaturation temperature of PCR), the terminated primer can become an extendable primer by thermally induced intra- and/or intermolecular fragmentation which removes the 3'-substitution group (FIGS. 1B and 2). The "extendable primer" possesses an unsubstituted or open 3'-OH and is capable of elongation by nucleic acid polymerase. In particularly preferred embodiments partial or complete conversion of the 3'-substitution group occurs after incubation at approximately 95° C. for approximately 1-120 minutes. In preferred embodiments, conversion of the 3'-substitution group of the terminated primer occurs with respect to temperature and does not require enzymes, additional chemicals, or modified polymerization reaction conditions other than those normally used in replications with standard dNTPs.

In a preferred embodiment, one or more of the components of a NTP polymerization reaction mixture, such as a 3'-substituted NTP, modified NTP, unmodified NTP, or combination thereof, present in the polymerization reaction, may be labeled with a detectable label. Thus, following replication, the target segment can be identified, for example, by size, mass, affinity capture or color. The detectable label is preferably a fluorescent dye, the affinity capture label is preferably biotin.

In another aspect, the methods and compositions herein provide for 3'-substituted NTPs for nucleic acid replication including a NTP that has one or more modification groups. The 3'-substituted NTPs may include one or more of the chemical structures depicted in Formulas IA and IB further described herein.

In yet another aspect, the methods and compositions herein provide for methods of synthesis of 3'-substituted NTPs as disclosed herein.

Kits including 3'-substituted NTPs for performing replication as described herein are also provided. For example, kits may contain PCR reagents for common replication targets such as housekeeping genes. The kit containing a 3'-substituted NTP may include a container marked for nucleic acid replication, instructions for performing nucleic acid replication and/or one or more reagents selected from the group consisting of modified primers, unmodified primers, modified NTPs (e.g., 3'-substituted NTPs), unmodified NTPs, nucleic acid polymerase, magnesium chloride or other divalent cation (e.g., magnesium and manganese) and reaction buffer. In one embodiment, the kit includes 3'-substituted NTPs, a nucleic acid polymerase and a least one additional enzyme (e.g., a second nucleic acid polymerase, reverse transcriptase, ligase or restriction enzyme), and may include additional buffer components suitable for the at least one additional enzyme(s). Preferably the kit includes two or more nucleic acid replication reagents, preferably three or more and more preferably, four or more. The kit containing a 3'-substituted NTP may also include oligonucleotide primers. In one embodiment, the oligonucleotide primers are modified, e.g., having any substitution or modification at the internucleotide linkages, nucleoside sugars, triphosphate chain, and/or nucleoside bases. The kits may include a container marked for nucleic acid replication, instructions for performing nucleic acid replication and/or one or more reagents selected from the group consisting of dNTPs, nucleic acid polymerase, magnesium, and reaction buffer.

The methods and compositions provided herein for nucleic acid replication are useful in applications that employ synthetic and/or natural NTPs, modified oligonucleotide primers, unmodified oligonucleotide primers and polymerase for extension of nucleic acid. The NTPs of the methods and compositions provided herein may have a single 3'-substitution or may optionally have additional modification sites.

The 3'-substituted NTPs of the methods and compositions provided herein have significant advantages. For example, an end user can use the same replication protocols and methods already in use with unsubstituted standard NTPs. The 3'-substituted NTPs of the methods and compositions provided herein are compatible with existing replication systems and reagents (including various hot start PCR methods); no additional enzymes or reagents are needed but can be used. Standard chemical and enzymatic synthesis methods can be used to synthesize the 3'-substituted NTPs of the methods and compositions provided herein. Polymerase based replication applications requiring fidelity can be used with the 3'-substituted NTPs of the methods and compositions provided herein.

As used herein, the term "replication," "amplification" or "amplify" refers to methods known in the art for copying a target nucleic acid, thereby increasing the number of copies of a selected nucleic acid sequence. Replication and amplification involving the compositions and methods provided herein may employ 3'-substituted NTPs and/or primers with nucleic acid polymerase extension. Replication or amplification of target nucleic acid may be exponential, nonlinear or linear. Preferably, replication or amplification is exponential or nonlinear. A target nucleic acid may be DNA, RNA, cDNA or a modified nucleic acid template. While the exemplary methods described hereinafter relate to PCR amplification, numerous other methods suitable for the methods and compositions provided herein are known in the art for enzymatic amplification and reproduction of nucleic acids. For example, other enzymatic replication and amplification methods include isothermal methods, rolling circle methods, Hot-start PCR, real-time PCR, Allele-specific PCR, Assembly PCR or Polymerase Cycling Assembly (PCA), Asymmetric PCR, Colony PCR, Emulsion PCR, Fast PCR, Real-Time PCR, nucleic acid ligation, Gap Ligation Chain Reaction (Gap LCR), Ligation-mediated PCR, Multiplex Ligation-dependent Probe Amplification, (MLPA), Gap Extension Ligation PCR (GEXL-PCR), quantitative PCR (Q-PCR), Quantitative real-time PCR (QRT-PCR), multiplex PCR, Helicase-dependent amplification, Intersequence-specific (ISSR) PCR, Inverse PCR, Linear-After-The-Exponential-PCR (LATE-PCR), Methylation-specific PCR (MSP), Nested PCR, Overlap-extension PCR, PAN-AC assay, Reverse Transcription PCR (RT-PCR), Rapid Amplification of cDNA Ends (RACE PCR), Single molecule amplification PCR (SMA PCR), Thermal asymmetric interlaced PCR (TAIL-PCR), Touchdown PCR, long PCR, nucleic acid sequencing (including DNA sequencing and RNA sequencing), transcription, reverse transcription, duplication, DNA or RNA ligation, and other nucleic acid extension reactions known in the art. The skilled artisan will understand that other methods may be used either in place of, or together with, PCR methods, including enzymatic replication reactions developed in the future. See, e.g., Saiki, "Amplification of Genomic DNA" in PCR Protocols, Innis et al., eds., Academic Press, San Diego, Calif., 13-20 (1990); Wharam, et al., 29(11) Nucleic Acids Res, E54-E54 (2001); Hafner, et al., 30(4) Biotechniques, 852-6, 858, 860 passim (2001); Ross, P., et al., International Patent Appl. No. WO 91/06678; Kwiatkowski, M., U.S. Pat. Nos. 6,255,475, 6,309,836, and 6,639,088 and EP1218391; Anazawa, T., et al., U.S. Pat. No. 6,242,193; Ju, et al., U.S. Pat. No. 6,664,079; Tsien, R. Y., et al., International Patent Appl. No. WO 91/06678; and Dower, et al., International Patent Appl. No. WO 92/10587.

As used herein, the terms "nucleic acid," "nucleotide sequence," or "nucleic acid sequence" refer to an oligonucleotide, polynucleotide, or any fragment thereof, any ribo- or deoxyriboderivatives and to naturally occurring or synthetic molecules containing natural and/or modified nucleotide residues and internucleotide linkages. These phrases also refer to DNA or RNA of natural (e.g., genomic) or synthetic origin which may be single-stranded, double-stranded, triple-stranded or tetra-stranded and may represent the sense or the antisense strand, or to any DNA-like or RNA-like material. An "RNA equivalent," in reference to a DNA sequence, is composed of the same linear sequence of nucleotides as the reference DNA sequence with the exception that all or most occurrences of the nitrogenous base thymine are replaced with uracil, and the sugar backbone is composed of ribose instead of 2'-deoxyribose. Additional alternative nucleic acid backbones suitable for the methods and compositions provided herein include but are not limited to phosphorothioate, phosphoroselenoate, alkyl phosphotriester, aryl phosphotriester, alkyl phosphonate, aryl phosphonate, Locked Nucleic Acids (LNA), and Peptide Nucleic Acids (PNA) and phosphoboronate. RNA may be used in the methods described herein and/or may be converted to cDNA by reverse-transcription for use in the methods described herein.

As used herein, the term "3'-substituted NTP" refers to a nucleoside 5'-triphosphate having a chemical moiety group other than an open hydroxyl group at the 3'-position. The 3'-substituted NTP includes, for example, a NTP containing a modified sugar, base or triphosphate chain, or any combination of modified sugar, base or triphosphate chain as presented, for example, in Formulas IA and IB further described herein. Examples of such NTPs can be found, for example in "Nucleoside Triphosphates and Their Analogs: Chemistry, Biotechnology and Biological Applications," Vaghefi, M., ed., Taylor and Francis, Boca Raton (2005); Metzker, M. L. 15 Genome Research 1767-1776 (2005) (and references therein).

As used herein, the term "primer," "oligonucleotide" or "oligonucleotide primer" refers to a ribo- or deoxyribo-polynucleotide, usually single stranded, may be naturally occurring or synthetic, and usually include a sequence of between about 5 to about 50 nucleotides, more preferably about 10 to about 30 nucleotides or more preferably about 15 to about 25 nucleotides. Oligonucleotides may contain one or more modification groups. Oligonucleotides may include DNA, RNA, PNA, LNA, and/or other modified nucleosides. The skilled artisan is capable of designing and preparing primers that are appropriate for replication of a target sequence. The length of the primer hybridization sequence of the primers for use in the methods and compositions provided herein depends on several factors including the nucleotide sequence identity and the temperature at which these nucleic acids are hybridized or used during in vitro nucleic acid replication. The considerations necessary to determine a preferred length for the primer hybridization sequence of a primer of a particular sequence identity are well known to the person of ordinary skill. For example, the length of a short nucleic acid or oligonucleotide can relate to its hybridization specificity or selectivity.

As used herein, the term "terminated primer" refers to a primer or oligonucleotide primer containing a 3'-substitution group incorporated by nucleic acid polymerase mediated incorporation of a terminating NTP onto the 3'-end of the primer. The terminated primer, which may include one or more additional modification groups of the methods and compositions provided herein, cannot be elongated prior to conversion of the 3'-substitution group to an open 3'-OH group. The terminated primer may include natural DNA or RNA nucleosides, modified nucleosides or nucleoside analogs, containing natural intermucleotide phosphodiester linkages or modifications thereof, or combination thereof Preferably, a 3'-substitution group is thermally labile and dissociates from the terminated primer at an increasing rate as the temperature of the replication reaction medium is raised.

As used herein, the term "extendable primer" refers to a primer or oligonucleotide primer containing an unmodified or open 3'-OH group and which can be extended by nucleic acid polymerase incorporation of a NTP onto the 3'-end of the primer. The extendable primer can be the original starting primer or can be a transformed terminated primer from which a 3'-substitution group has been converted to a free 3'-OH group.

As used herein, the term "3'-substitution group" refers to a chemical moiety at the 3'-position of a NTP or primer other than an unmodified or open hydroxyl group (3'-OH). In certain embodiments, the chemical moiety is an ether, ester, or carbonate. In certain preferred embodiments, the 3'-substitution group is selected from the group consisting of O-(p-toluene)sulfonate; O-phosphate: O-nitrate; O-[4-methoxy] tetrahydropyranyl; O-[4-methoxy]-tetrahydrothiopyranyl; O-tetrahydrothiopyranyl; O-[5-methyl]-tetrahydrofuranyl; O-[2-methyl, 4-methoxy]-tetrahydropyranyl; O-[5-methyl]-tetrahydropyranyl; O-tetrahydropyranyl; O-tetrahydrofuranyl; O-phenoxyacetyl; O-methoxyacetyl; O-acetyl; O—C(O)—OCH$_3$; O—C(O)—CH$_2$CH$_2$CN; and O—C(S)—OCH$_3$. In some particularly preferred embodiments, the 3'-substitution group is selected from the group consisting of O-methoxytetrahydropyranyl; O-tetrahydropyranyl; and O-tetrahydrofuranyl.

The 3'-substituted NTPs of the methods and compositions provided herein preferably have no or reduced efficacy for oligonucleotide or nucleic acid extension. Preferably, extension is considered impaired when a 3'-substituted NTP is at least 50% less efficacious as a substrate in a replication reaction compared to its corresponding 3'-unsubstituted NTP, preferably at least 60% less efficacious, preferably at least 70% less efficacious, more preferably at least 80% less efficacious, more preferably at least 90% less efficacious, more preferably at least 95% less efficacious, more preferably at least 99% less efficacious and most preferably 100% less efficacious as a substrate in a replication reaction than its corresponding 3'-unsubstituted NTP. One of ordinary skill in the art is able to readily determine the level of substrate activity and efficacy of NTPs. One method of determining substrate efficacy is illustrated in Example 4. In certain preferred embodiments, 3'-substitution groups are heat labile and dissociate from a 3'-substituted NTP at an increasing rate as the temperature of the replication reaction medium is raised.

As used herein, the term "3-unsubstituted," "natural," or "unmodified" in the context of NTPs and oligonucleotide primers refers to NTPs and oligonucleotide primers without a modification group or the functional equivalent of a NTP or oligonucleotide primer without a modification group.

In addition to the 3'-substitution group, a 3'-substituted NTP or 3'-substituted primer may contain one or more additional modification groups. As used herein, the term "modification group" refers to any chemical moiety which can be attached to a NTP or primer at locations which include, but are not limited to the phosphate, sugar, triphosphate chain or nucleoside base moieties. The modification group of a NTP or primer may be a group of any nature compatible with the process of nucleic acid replication. The modification group may be a labile group which dissociates from a modified NTP or modified primer at an increasing rate as the temperature of the enzyme reaction medium is raised. In one embodiment, the modification group of the modified primer present in the polymerization reaction may be present at an intermucleotide linkage, e.g., such as described in U.S. Patent Application No. 20070281308, In another embodiment, the modification group of a modified NTP or primer present in the polymerization reaction may be a detectable label. Thus, following replication, the target segment can be identified by size, mass, affinity capture and/or color. The detectable label is preferably a fluorescent dye; the affinity capture label is preferably biotin.

As used herein, the term "terminus" with respect to an oligonucleotide refers to the nucleotides at the 3' or 5' end of an oligonucleotide. Preferably the terminus of an oligonucleotide includes the terminal 6 nucleotides, more preferably the terminal 5 nucleotides, more preferably the terminal 4 nucleotides, more preferably the terminal 3 nucleotides, more preferably the terminal 2 nucleotides, or more preferably the terminal nucleotide.

As used herein, the term "convert," "dissociate," "dissociation" or "fragmentation" refers to the removal or transformation of a modification group (e.g., by removal or transformation of a 3'-substitution group to a 3'-OH group), from a NTP or primer. Removal or transformation of a modification group may be partial, e.g., when the 3'-substitution group dissociates from a fraction of modified molecules, or complete, when the 3'-substitution group dissociates from all modified molecules. In certain preferred embodiments, removal or transformation of a modification group at the 3'-position results in the formation of an open 3'-OH group at the 3'-position of a NTP or primer. Removal or transformation of a modification group may occur by an intramolecular reaction or by reaction with another molecule. Preferably, removal or transformation of a 3'-substitution group converts a 3'-substituted NTP to the active state and a terminated primer to an extendable primer.

As used herein, the term "intermucleotide linkage" refers to the bond or bonds that connect two nucleosides of an oligonucleotide primer or nucleic acid and may be a natural phosphodiester linkage or modified linkage.

As used herein, the term "target," "target nucleic acid sequence," or "nucleic acid target" refers to a sequence of nucleotides to be identified.

As used herein, the term "label" or "detectable label" refers to any compound or combination of compounds that may be attached or otherwise associated with a molecule so that the molecule can be detected directly or indirectly by detecting the label. A detectable label can be a radioisotope (e.g., carbon, phosphorus, iodine, indium, sulfur, tritium etc.), a mass isotope (e.g., H$^2$, C$^{13}$ or N$^{15}$), a dye or fluorophore (e.g., cyanine, fluorescein or rhodamine), a hapten (e.g., biotin) or any other agent that can be detected directly or indirectly.

After incorporation of a labeled NTP into an amplicon or other polymerization product, the label may be detected.

As used herein, the term "heat induction" or "heat conversion" refers to the process by which heat is applied to remove or transform the 3'-substitution group of a 3'-substituted NTP, thereby generating a suitable substrate for nucleic acid polymerases. The term heat induction or heat conversion also refers to the process by which heat is applied to remove or transform the 3'-substitution group of a terminated primer generating an extendable primer thus making it a substrate for nucleic acid polymerases.

As used herein, the term "hot start" refers to a nucleic acid replication reaction where polymerase mediated nucleic acid replication is impaired until the reaction reaches a desired temperature, which is preferably an initial temperature above the optimal extension temperature of the enzyme. In hot start PCR applications, initial temperatures reach between about 80-105° C.; or at least 80° C., or at least 85° C., or at least 90° C., or about 94° C., or about 95° C., or about 96° C., or about 100° C. Preferably, "hot start" PCR requires that the nucleic acid polymerase and all other PCR components are added before the initial denaturation step. The term hot start is well known in the art and there are a number of methods known to impair replication such as modified polymerases, oligonucleotides with secondary structures impairing hybridization or oligonucleotides with chemical modifications impairing extension and reagents contained in temperature sensitive barriers such as wax. In a preferred embodiment, hot start amplification is initiated by heat induced conversion of a 3'-substitution group in a non substrate NTP, terminating NTP or terminated primer to an open 3'-OH group.

As used herein, the term "mis-priming" refers to non-specific initiation of nucleic acid polymerase mediated primer extension. In particular it relates to the nucleic acid sequences having a certain degree of non-complementarity to the primer and potentially initiating synthesis of undesired extension products, which can be amplified along with the target sequence.

As used herein, the term "inactive state" or "inactive" in the context of a NTP refers to a non substrate NTP with a 3'-substitution group. In one embodiment, the attachment of a 3'-substitution group to the NTP makes it inactive and impairs incorporation of the 3'-substituted NTP into an oligonucleotide primer, thus preventing 3'-extension by a nucleic acid polymerase (FIG. 1A). As used herein, the term "terminating state" in the context of a terminating NTP, refers to a 3'-substituted NTP capable of being incorporated onto the 3'-end of a primer to form an unextendable N+1 extended primer (i.e., terminated primer) (FIG. 1B).

As used herein, the term "terminating state" in the context of a primer, refers to a primer that contains a 3'-substitution group at its 3'-end (FIG. 1B). In one embodiment, the incorporation of a 3'-substituted terminating NTP onto the 3'-end of the primer causes temporary termination of the extension of the primer. The resulting terminated primer does not support nucleic acid replication reactions and cannot be extended further until the 3'-substitution group is converted to an open 3'-OH group.

As used herein, the terms "active state" or "active" in the context of a NTP, refer to a NTP which can be a substrate for polymerase. Preferably, an "active" NTP does not have a 3'-substitution or it may be a terminating NTP containing a converted 3'-substitution group. Preferably, an active NTP has an unmodified 3'-OH group and can serve as a substrate for nucleic acid polymerase in replication reactions. An active state NTP may be a NTP that has never had a 3'-substitution or a NTP from which a 3'-substitution has been converted, removed or transformed.

As used herein, the term "primer dimer(s)" refers to a non-specific oligonucleotide primer extension product(s) which results from amplification of two extended oligonucleotide primers hybridized across one another's sequence without significant intervening sequence.

As used herein, the term "hybridize" or "specifically hybridize" refers to a process where two complementary nucleic acid strands anneal to each other under appropriately stringent conditions. Hybridizations to target nucleic acids are typically and preferably conducted with probe-length nucleic acid molecules, preferably 20-100 nucleotides in length. Nucleic acid hybridization techniques are well known in the art. See, e.g., Sambrook, et al., Molecular Cloning: A Laboratory Manual, Second Edition, Cold Spring Harbor Press, Plainview, N.Y. (1989), Ausubel, F. M., et al., Current Protocols in Molecular Biology, John Wiley & Sons, Secaucus, N.J. (1994).

As used herein, the term "stringent hybridization condition" refers to hybridization conditions which do not allow for hybridization of two nucleic acids which are not completely complementary.

As used herein, the term "sample" or "test sample" refers to any liquid or solid material believed to include nucleic acid of interest. A test sample may be obtained from any biological source (i.e., a biological sample), such as cells in culture or a tissue sample or synthetically produced including a chemically synthesized template.

As used herein, the term "complement," "complementary," or "complementarity" in the context of an oligonucleotide or polynucleotide (i.e., a sequence of nucleotides such as an oligonucleotide primers or a target nucleic acid) refers to standard Watson/Crick base pairing rules. A complement sequence can also be a sequence of DNA or RNA complementary to the DNA sequence or its complement sequence, and can also be a cDNA. For example, the sequence "5'-A-G-T-C-3'" is complementary to the sequence "3'-T-C-A-G-5'." Certain nucleotides not commonly found in natural nucleic acids or chemically synthesized may be included in the nucleic acids described herein; these include but not limited to base and sugar modified nucleosides, nucleotides, and nucleic acids, such as inosine, 7-deazaguanosine, 2'-O-methylguanosine, 2'-fluoro-2'-deoxycytidine, Locked Nucleic Acids (LNA), and Peptide Nucleic Acids (PNA). Complementarity need not be perfect; stable duplexes may contain mismatched base pairs, degenerative, or unmatched nucleotides. Those skilled in the art of nucleic acid technology can determine duplex stability empirically considering a number of variables including, for example, the length of the oligonucleotide, base composition and sequence of the oligonucleotide, incidence of mismatched base pairs, ionic strength, other hybridization buffer components and conditions.

Complementarity may be "partial" in which only some of the nucleotide bases of two nucleic acid strands are matched according to the base pairing rules. Complementarity may be complete or total where all of the nucleotide bases of two nucleic acid strands are matched according to the base pairing rules. Complementarity may be absent where none of the nucleotide bases of two nucleic acid strands are matched according to the base pairing rules. The degree of complementarity between nucleic acid strands has significant effects on the efficiency and strength of hybridization between nucleic acid strands. This is of particular importance in amplification reactions, as well as detection methods that depend upon binding between nucleic acids. The terms may also be used in reference to individual nucleotides, especially within the context of polynucleotides. For example, a particular nucleotide within an oligonucleotide may be noted for its complementarity, or lack thereof, to a nucleotide within another nucleic acid strand, in contrast or comparison to the complementarity between the rest of the oligonucleotide and the nucleic acid strand.

As used herein, the term "substantially complementary" refers to two sequences that hybridize under stringent hybridization conditions. The skilled artisan will understand that substantially complementary sequences need not hybridize along their entire length. In particular, substantially complementary sequences comprise a contiguous sequence of bases that do not hybridize to a target sequence, positioned 3' or 5' to a contiguous sequence of bases that hybridize under stringent hybridization conditions to a target sequence.

As used herein, the term "forward primer" refers to an oligonucleotide primer that anneals to the anti-sense strand of single stranded RNA, single stranded DNA, or double stranded DNA. A "reverse primer" anneals to the sense strand of single stranded RNA, single stranded DNA, or double stranded DNA.

As used herein, an oligonucleotide primer is "specific" for a nucleic acid if the oligonucleotide primer hybridization sequence of the oligonucleotide primer has at least 50% sequence identity with a portion of the nucleic acid when the oligonucleotide primer and the nucleic acid are aligned. An oligonucleotide primer that is specific for a nucleic acid is one that, under the appropriate hybridization or washing conditions, is capable of hybridizing to the target of interest and not substantially hybridizing to nucleic acids sequences which are not of interest. Higher levels of sequence identity are preferred and include at least 75%, at least 80%, at least 85%, at least 90%, at least 95%, at least 99%, and more preferably 100% sequence identity.

As used herein, the term "nucleoside" includes all naturally occurring nucleosides, including all forms of nucleoside bases and furanosides found in natural nucleic acids. Base rings most commonly found in naturally occurring nucleosides are purine and pyrimidine rings. Naturally occurring purine rings include, for example, adenine, guanine, and $N^6$-methyladenine. Naturally occurring pyrimidine rings include, for example, cytosine, thymine, and 5-methylcytosine. Naturally occurring nucleosides for example include but not limited to ribo and 2'-deoxyribo derivatives of adenosine, guanosine, cytidine, thymidine, uridine, inosine, 7-deazaguanosine, 7-methyl guanosine.

As used herein, the terms "nucleoside analogs," "modified nucleosides." or "nucleoside derivatives" include synthetic nucleosides as described herein. Nucleoside derivatives also include nucleosides having modified base or/and sugar moieties, with or without protecting groups. Such analogs include, for example, 2'-deoxy-2'-fluorouridine, 2'-O-methyluridine and the like. The compounds and methods of provided herein include such base rings and synthetic analogs thereof, as well as unnatural heterocycle-substituted base sugars, and even acyclic substituted base sugars. Moreover, nucleoside derivatives include other purine and pyrimidine derivatives, for example, halogen-substituted purines (e.g., 6-fluoropurine), halogen-substituted pyrimidines, $N^6$-ethyladenine, $N^4$-(alkyl)-cytosines, 5-ethylcytosine, and the like. Nucleoside derivatives and analogs encompass a wide variety of modifications, such as those described in U.S. Pat. No. 6,762,298.

As used herein, the terms "universal base NTP," "degenerate base NTP." "universal base NTP analog" and "degenerate base NTP analog" includes, for example, a NTP analog with an artificial base which is preferably recognizable by nucleic acid polymerase as a substitute for any specific NTP such as dATP, ATP, dTTP, dUTP, dCTP, CTP, dGTP, GTP and other specific NTP. NTPs with universal bases or degenerate bases can also be used and examples can be found in Loakes, D., 29 Nucleic Acids Res. 2437-2447 (2001); Crey-Desbiolles, C., et. al., 33 Nucleic Acids Res. 1532-1543 (2005); Kincaid, K., et. al., 33 Nucleic Acids Res. 2620-2628 (2005); Preparata, F P, Oliver, J S, 11 J. Comput. Biol. 753-765 (2004); and Hill, F., et. al., 95 Proc Natl Acad Sci USA. 4258-4263 (1998).

As used herein, the term "modified oligonucleotide" includes, for example, an oligonucleotide containing a modified nucleoside, a modified intermucleotide linkage, or having any combination of modified nucleosides and intermucleotide linkages (even if only a natural nucleosides are present in the oligonucleotide chain). Examples of oligonucleotide intermucleotide linkage modifications can be found, for example, in Waldner, et al., 6 Bioorg. Med. Chem. Letters 2363-2366 (1996). Examples of modified oligonucleotides are phosphorothioate, phosphotriester and methylphosphonate derivatives of oligonucleotides can be found, for example, in Stec, W. J., et al., 33 Chem. Int. Ed. Engl., 709-722 (1994); Lebedev, A. V., et al., E., 4 Perspect. Drug Discov. Des., 17-40 (1996); and Zon, et al., U.S. Patent Application No. 200702281308. The ten modified oligonucleotide encompasses oligonucleotides having a 3'-substitution at the 3'-terminal nucleotide, As used herein, the term "acyl" denotes the group —C(O)$R^a$, where $R^a$ is hydrogen, lower alkyl, cycloalkyl, heterocyclyl, aryl, heteroaryl, and the like.

As used herein, the term "substituted acyl" denotes the group —C(O)$R^{a'}$, where $R^{a'}$ is substituted lower alkyl, substituted cycloalkyl, substituted heterocyclyl, substituted aryl, substituted heteroaryl, and the like.

As used herein, the term "acyloxy" denotes the group —OC(O)$R^b$, where $R^b$ is hydrogen, lower alkyl, substituted lower alkyl, cycloalkyl, substituted cycloalkyl, heterocyclyl, substituted heterocyclyl, aryl, substituted aryl, heteroaryl, substituted heteroaryl, and the like.

As used herein, the term "alkane" refers to an organic compound that includes carbon atoms and hydrogen atoms, and includes C—H bonds and additionally includes C—C single bonds in alkanes other than methane. The term "alkane" includes straight-chain alkanes such as alkanes having from 1 to 20 carbon atoms. In some embodiments, alkanes include straight-chain alkanes such as alkanes having from 1 to 8 carbon atoms such as methane, ethane, propane, butane, pentane, hexane, heptane, and octane. The term "alkane" also includes branched-chain alkanes such as, but not limited to branched chain alkanes having from 1 to 20, and in some embodiments from 1 to 8 carbon atoms such as, but not limited to, 2-methylpropane, 2,2-dimethylpropane, 2-methylbutane, 2,3-dimethylbutane, 2,2-dimethylbutane, 2-methylpentane, 3-methylpentane, 2,3-dimethylpentane, 2,4-dimethylpentane, 2,2-dimethylpentane, 3,3-dimethylpentane, 2-methylhexane, 3-methylhexane, 2,2-dimethylhexane, 2,3-dimethylhexane, 2,4-dimethylhexane, 2,5-dimethylhexane, 3,3-dimethylhexane, 3.4-dimethylhexane, 2-methylheptane, 3-methylheptane, 4-methylheptane, 3-ethylpentane, 3-ethyl-2-methylpentane, 3-ethylhexane, and the like, A C—C or a C—H bond of an alkane may be replaced with a bond to another group such as a hydroxyl group, a halogen such as F, Cl, Br, or I, a sulfhydryl group, or an amine group. Alkanes replaced with such groups may respectively be named as hydroxyalkanes, haloalkanes such as fluoroalkanes. chloroalkanes, bromoalkanes, iodoalkanes, mercaptoalkanes, and aminoalkanes.

As used herein, the term "alkenyl" refers to a straight-chain or branched-chain hydrocarbyl, which has one or more double bonds and, unless otherwise specified, contains from about 2 to about 20 carbon atoms, preferably from about 2 to about 10 carbon atoms, more preferably from about 2 to about 8 carbon atoms, and most preferably from about 2 to about 6 carbon atoms. Examples of alkenyl radicals include vinyl, allyl, 1,4-butadienyl, isopropenyl, and the like.

As used herein, the term "alkenylaryl" refers to alkenyl-substituted aryl groups and "substituted alkenylaryl" refers to alkenylaryl groups further bearing one or more substituents as set forth herein.

As used herein, the term "alkenylene" refers to divalent straight or branched chain hydrocarbyl groups having at least one carbon-carbon double bond, and typically containing 2-20 carbon atoms, preferably 2-12 carbon atoms, preferably 2-8 carbon atoms, and "substituted alkenylene" refers to alkenylene groups further bearing one or more substituents as set forth herein.

As used herein, the term "alkyl" refers to a single bond chain of hydrocarbons usually ranging from 1-20 carbon atoms, preferably 1-8 carbon atoms, examples include methyl, ethyl, propyl, isopropyl, and the like. Examples of such alkyl radicals include methyl, ethyl, propyl, isopropyl, n-butyl, sec-butyl, isobutyl, tert-butyl, pentyl, isoamyl, hexyl, octyl, dodecanyl, and the like.

As used herein, the term "lower alkyl" refers to a straight chain or a branched chain of hydrocarbons usually ranging from 1-6 carbon atoms, preferably 2-5 carbon atoms. Examples include ethyl, propyl, isopropyl, and the like.

As used herein, the term "alkylene" refers to a divalent hydrocarbyl containing 1-20 carbon atoms, preferably 1-15 carbon atoms, straight chain or branched, from which two hydrogen atoms are taken from the same carbon atom or from different carbon atoms. Examples of alkylene include, but are not limited to, methylene (—$CH_2$—), ethylene (—$CH_2CH_2$—), and the like.

As used herein, the term "alkynyl" refers to a straight-chain or branched-chain hydrocarbyl, which has one or more triple bonds and contains from about 2-20 carbon atoms, preferably from about 2-10 carbon atoms, more preferably from about 2-8 carbon atoms, and most preferably from about 2-6 carbon atoms. Examples of alkynyl radicals include ethynyl. propynyl(propargyl), butynyl, and the like.

As used herein, the term "alkynylaryl" refers to alkynyl-substituted aryl groups and "substituted alkynylaryl" refers to alkynylaryl groups further bearing one or more substituents as set forth herein.

As used herein, the term "alkoxy" denotes the group —$OR^c$, where $R^c$ is lower alkyl, substituted lower alkyl, aryl, substituted aryl, aralkyl, substituted aralkyl, heteroalkyl, heteroarylalkyl, cycloalkyl, substituted cycloalkyl, cycloheteroalkyl, or substituted cycloheteroalkyl as defined.

As used herein, the term "lower alkoxy" denotes the group —$OR^d$, where $R^d$ is lower alkyl.

As used herein, the term "alkylaryl" refers to alkyl-substituted aryl groups and "substituted alkylaryl" refers to alkylaryl groups further bearing one or more substituents as set forth herein.

As used herein, the term "alkylcarbonylamino" denotes the group —$NR^eC(O)R^f$, where $R^e$ is optionally substituted alkyl, and $R^f$ is hydrogen or alkyl.

As used herein, the term "alkylsulfinyl" denotes the group —$S(O)R^g$, where $R^g$ is optionally substituted alkyl.

As used herein, the term "alkylsulfonyl" denotes the group —$S(O)_2R^g$, where $R^g$ is optionally substituted alkyl.

As used herein, the term "alkylsulfonylamino" denotes the group —$NR^eS(O)_2R^f$, where $R^e$ is optionally substituted alkyl, and $R^f$ is hydrogen or alkyl.

As used herein, the term "alkylthio" refers to the group —S—$R^h$, where $R^h$ is alkyl.

As used herein, the term "substituted alkylthio" refers to the group —S—$R^i$, where $R^i$ is substituted alkyl.

As used herein, the term "alkynylene" refers to divalent straight or branched chain hydrocarbyl groups having at least one carbon-carbon triple bond, and typically having in the range of about 2-12 carbon atoms, preferably about 2-8 carbon atoms, and "substituted alkynylene" refers to alkynylene groups further bearing one or more substituents as set forth herein.

As used herein, the term "amido" denotes the group —$C(O)NR^jR^{j'}$, where $R^j$ and $R^{j'}$ may independently be hydrogen, lower alkyl, substituted lower alkyl, alkyl, substituted alkyl, aryl, substituted aryl, heteroaryl, or substituted heteroaryl.

As used herein, the term "substituted amido" denotes the group —$C(O)NR^kR^{k'}$, where $R^k$ and $R^{k'}$ are independently hydrogen, lower alkyl, substituted lower alkyl, aryl, substituted aryl, heteroaryl, or substituted heteroaryl, provided, however, that at least one of $R^k$ and $R^{k'}$ is not hydrogen. $R^kR^{k'}$ in combination with the nitrogen may form an optionally substituted heterocyclic or heteroaryl ring.

As used herein, the term "amidino" denotes the group —$C(=NR^m)NR^{m'}R^{m''}$, where $R^m$, $R^{m'}$, and $R^{m''}$ are independently hydrogen or optionally substituted alkyl, aryl, or heteroaryl.

As used herein, the term "amino" or "amine" denotes the group —$NR^nR^{n'}$, where $R^n$ and $R^{n'}$ may independently be hydrogen, lower alkyl, substituted lower alkyl, alkyl, substituted alkyl, aryl, substituted aryl, heteroaryl, or substituted heteroaryl as defined herein. A "divalent amine" denotes the group —NH—. A "substituted divalent amine" denotes the group —NR— where R is lower alkyl, substituted lower alkyl, alkyl, substituted alkyl, aryl, substituted aryl, heteroaryl, or substituted heteroaryl.

As used herein, the term "substituted amino" or "substituted amine" denotes the group —$NR^pR^{p'}$, where $R^p$ and $R^{p'}$ are independently hydrogen, lower alkyl, substituted lower alkyl, alkyl, substituted alkyl, aryl, substituted aryl, heteroaryl, substituted heteroaryl, provided, however, that at least one of $R^p$ and $R^{p'}$ is not hydrogen. $R^pR^{p'}$ in combination with the nitrogen may form an optionally substituted heterocyclic, or heteroaryl ring.

As used herein, the term "arylalkynyl" refers to aryl-substituted alkynyl groups and "substituted arylalkynyl" refers to arylalkynyl groups further bearing one or more substituents as set forth herein.

As used herein, the term "aralkyl" refers to alkyl as defined herein, where an alkyl hydrogen atom is replaced by an aryl as defined herein. Examples of aralkyl radicals include benzyl, phenethyl, 1-phenylpropyl, 2-phenylpropyl, 3-phenylpropyl, 1-naphthylpropyl, 2-naphthylpropyl, 3-naphthylpropyl, 3-naphthylbutyl, and the like.

As used herein, the term "aroyl" refers to aryl-carbonyl species such as benzoyl and "substituted aroyl" refers to aroyl groups further bearing one or more substituents as set forth herein.

As used herein, the term "arylalkyl" refers to aryl-substituted alkyl groups and "substituted arylalkyl" refers to arylalkyl groups further bearing one or more substituents as set forth herein.

As used herein, the term "aryl" alone or in combination refers to phenyl, naphthyl or fused aromatic heterocyclic optionally with a cycloalkyl of preferably 5-7, more preferably 5-6, ring members and/or optionally substituted with 1 to 3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, aryl sulfonyl amino, heteroarylsulfonyl amino, alkylcarbonyl amino, aryl carbonyl amino, heteroarylcarbonylamino, or the like.

As used herein, the term "arylcarbonylamino" denotes the group —$NR^qC(O)R^r$, wherein $R^q$ is hydrogen or lower alkyl or alkyl and $R^r$ is optionally substituted aryl.

As used herein, the term "arylene" refers to divalent aromatic groups typically having in the range of 6 up to 14 carbon atoms and "substituted arylene" refers to arylene groups further bearing one or more substituents as set forth herein.

As used herein, the term "aryloxy" denotes the group —OAr, where Ar is an aryl, or substituted aryl group.

As used herein, the term "arylsulfonylamino" denotes the group —$NR^qS(O)_2R^r$, where $R^q$ is hydrogen or lower alkyl, or alkyl and $R^r$ is optionally substituted aryl.

As used herein, the term "a carbamate group" denotes the group —O—C(O)—$NR_2$, where each R is independently H, alkyl, substituted alkyl, aryl, or substituted aryl as set forth herein.

As used herein, the term "dithiocarbamate group" denotes the group —S—C(S)—$NR^2$, where each R is independently H, alkyl, substituted alkyl, aryl, or substituted aryl as set forth herein.

As used herein, the term "carbocycle" refers to a saturated, unsaturated, or aromatic group having a single ring or multiple condensed rings composed of linked carbon atoms. The ring(s) can optionally be unsubstituted or substituted with, e.g., halogen, lower alkyl, alkoxy, alkylthio, acetylene, amino, amido, carboxyl, hydroxyl, aryl, aryloxy, heterocycle, hetaryl, substituted hetaryl, nitro, cyano, thiol, sulfamido, and the like.

As used herein, the term "cycloalkenyl" refers to cyclic ring-containing groups containing in the range of 3-20 carbon atoms and having at least one carbon-carbon double bond, and "substituted cycloalkenyl" refers to cycloalkenyl groups further bearing one or more substituents as set forth herein.

As used herein, the term "cycloalkyl" refers to a monocyclic or polycyclic alkyl group containing 3-15 carbon atoms, and "substituted cycloalkyl" refers to cycloalkyl groups further bearing one or more substituents as set forth herein.

As used herein, the term "cycloalkylene" refers to divalent ring-containing groups containing in the range of about 3-12 carbon atoms, and "substituted cycloalkylene" refers to cycloalkylene groups further bearing one or more substituents as set forth herein.

As used herein, the term "guanidinyl" denotes the group —N=$C(NH_2)_2$ and "substituted guanidinyl" denotes the group —N=$C(NR_2)_2$, where each R is independently H, alkyl, substituted alkyl, aryl, or substituted aryl as set forth herein.

As used herein, the term "halo" or "halogen" refers to all halogens, i.e., chloro (Cl), fluoro (F), bromo (Br), and iodo (I).

As used herein, the term "heteroaryl" refers to a monocyclic aromatic ring structure containing 5 or 6 ring atoms, or a bicyclic aromatic group having 8-10 atoms, containing one or more, preferably 1-4, more preferably 1-3, even more preferably 1-2 heteroatoms independently selected from the group O, S, and N, and optionally substituted with 1-3 groups or substituents of halo, hydroxy, alkoxy, alkylthio, alkylsulfinyl, alkylsulfonyl, acyloxy, aryloxy, heteroaryloxy, amino optionally mono- or di-substituted with alkyl, aryl or heteroaryl groups, amidino, urea optionally substituted with alkyl, aryl, heteroaryl, or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intended to include oxidized S or N, such as sulfinyl, sulfonyl, and N-oxide of a tertiary ring nitrogen. A carbon or nitrogen atom is the point of attachment of the heteroaryl ring structure such that a stable aromatic ring is retained. Examples of heteroaryl groups are phthalimide, pyridinyl, pyridazinyl, pyrazinyl, quinazolinyl, purinyl, indolyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl, and the like. A substituted heteroaryl contains a substituent attached at an available carbon or nitrogen to produce a stable compound.

As used herein, the term "substituted heteroaryl" refers to a heterocycle optionally mono or poly substituted with one or more functional groups, e.g., halogen, lower alkyl, lower alkoxy, alkylthio, acetylene, amino, amido, carboxyl, hydroxyl, aryl, aryloxy, heterocycle, substituted heterocycle, hetaryl, substituted hetaryl, nitro, cyano, thiol, sulfamido, and the like.

As used herein, the term "heteroarylcarbonylamino" denotes the group —$NR^qC(O)R^r$, where $R^q$ is hydrogen or lower alkyl, and $R^r$ is optionally substituted aryl.

As used herein, the term "heteroaryloxy" denotes the group —OHet, where Het is an optionally substituted heteroaryl group.

As used herein, the term "heteroarylsulfonylamino" denotes the group —$NR^qS(O)_2R^s$, where $R^q$ is hydrogen or lower alkyl and $R^s$ is optionally substituted heteroaryl.

As used herein, the term "heterocycle" refers to a saturated, unsaturated, or aromatic group having a single ring (e.g., morpholino, pyridyl or furyl) or multiple condensed rings (e.g., naphthpyridyl, quinoxalyl, quinolinyl, indolizinyl or benzo[b]thienyl) and having carbon atoms and at least one hetero atom, such as N, O or S, within the ring, which can optionally be unsubstituted or substituted with, e.g., halogen, lower alkyl, lower alkoxy, alkylthio, acetylene, amino, amido, carboxyl, hydroxyl, aryl, aryloxy, heterocycle, hetaryl, substituted hetaryl, nitro, cyano, thiol, sulfamido, and the like.

As used herein, the term "substituted heterocycle" refers to a heterocycle substituted with 1 or more, e.g., 1, 2, or 3, substituents selected from the group consisting of optionally substituted alkyl, optionally substituted alkenyl, optionally substituted alkynyl, halo, hydroxy, alkoxy, alkylthio, alkylsulfinyl, alkylsulfonyl, acyloxy, aryl, substituted aryl, aryloxy, heteroaryloxy, amino, amido, amidino, urea optionally substituted with alkyl, aryl, heteroaryl or heterocyclyl groups, aminosulfonyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, acyl, carboxyl, heterocycle, substituted heterocycle, hetaryl, substituted hetaryl, nitro, cyano, thiol, sulfonamido, and oxo, attached at any available point to produce a stable compound.

As used herein, the term "hydrocarbyl" refers to any organic radical where the backbone thereof comprises carbon and hydrogen only. Thus, hydrocarbyl embraces alkyl, cycloalkyl, alkenyl, cycloalkenyl, alkynyl, aryl, alkylaryl, arylalkyl, arylalkenyl, alkenylaryl, arylalkynyl, alkynylaryl, and the like.

As used herein, the term "substituted hydrocarbyl" refers to any of the above-referenced hydrocarbyl groups further bearing one or more substituents selected from hydroxy, hydrocarbyloxy, substituted hydrocarbyloxy, alkylthio, substituted alkylthio, arylthio, substituted arylthio, amino, alkylamino, substituted alkylamino, carboxy, —C(S)SR, —C(O)SR, —C(S)NR$_2$, where each R is independently hydrogen, alkyl or substituted alkyl, nitro, cyano, halo, —SO$_3$M or —OSO$_3$M, where M is H, Na, K, Zn, Ca, or meglumine, guanidinyl, substituted guanidinyl, hydrocarbyl, substituted hydrocarbyl, hydrocarbylcarbonyl, substituted hydrocarbylcarbonyl, hydrocarbyloxycarbonyl, substituted hydrocarbyloxycarbonyl, hydrocarbylcarbonyloxy, substituted hydrocarbylcarbonyloxy, acyl, acyloxy, heterocyclic, substituted heterocyclic, heteroaryl, substituted heteroaryl, heteroarylcarbonyl, substituted heteroarylcarbonyl, carbamoyl, monoalkylcarbamoyl, dialkylcarbamoyl, arylcarbamoyl, a carbamate group, a dithiocarbamate group, aroyl, substituted aroyl, organosulfonyl, substituted organosulfonyl, organosulhinyl, substituted alkylsulfinyl, alkylsulfonylamino, substituted alkylsulfonyl amino, arylsulfonylamino, substituted arylsulfonylamino, a sulfonamide group, sulfuryl, and the like, including two or more of the above-described groups attached to the hydrocarbyl moiety by such linker/spacer moieties as —O—, —S—, —NR—, where R is hydrogen, alkyl or substituted alkyl, —C(O)—, —C(S)—, —C(=NR')—, —C(=CR'$_2$)—, where R' is alkyl or substituted alkyl, —O—C(O)—, —O—C(O)—O—, —O—C(O)—NR— (or —NR—C(O)—O—), —NR—C(O)—, —NR—C(O)—NR—, —S—C(O)—, —S—C(O)—O—, —S—C(O)—NR—, —O—S(O)$_2$—, —O—S(O)$_2$—O—, —O—S(O)$_2$—NR—, —O—S(O)—, —O—S(O)—O—, —O—S(O)—NR—, —O—NR—C(O)—, —O—NR—C(O)—O—, —O—NR—C(O)—NR—, —NR—O—C(O)—, —NR—O—C(O)—O—, —NR—O—C(O)—NR—, —O—NR—C(S)—, —O—NR—C(S)—O—, —O—NR—C(S)—NR—, —NR—O—C(S)—, —NR—O—C(S)—O—, —NR—O—C(S)—NR—, —O—C(S)—, —O—C(S)—O—, —O—C(S)—NR— (or —NR—C(S)—O—), —NR—C(S)—, —NR—C(S)—NR—, —S—S(O)$_2$—, —S—S(O)$_2$—O—, —S—S(O)$_2$—NR—, —NR—O—S(O)—, —NR—O—S(O)—O—, —NR—O—S(O)—NR—, —NR—O—S(O)$_2$—, —NR—O—S(O)$_2$—O—, —NR—O—S(O)$_2$—NR—, —O—NR—S(O)—, —O—NR—S(O)—O—, —O—NR—S(O)—NR—, —O—NR—S(O)$_2$—O—, —O—NR—S(O)$_2$—NR—, —O—NR—S(O)$_2$—, —O—P(O)R$_2$—, —S—P(O)R$_2$—, or —NR—P(O)R$_2$—, where each R is independently hydrogen, alkyl or substituted alkyl, and the like.

As used herein, the term "hydrocarbyloxy" denotes —O-hydrocarbyl groups containing 2-20 carbon atoms and "substituted hydrocarbyloxy" refers to hydrocarbyloxy groups further bearing one or more substituents as set forth herein.

As used herein, the term "hydrocarbylcarbonyl" refers to —C(O)-hydrocarbyl groups containing 2-20 carbon atoms and "substituted hydrocarbylcarbonyl" refers to hydrocarbylcarbonyl groups further bearing one or more substituents as set forth herein.

As used herein, the term "hydrocarbyloxycarbonyl" refers to —C(O)—O-hydrocarbyl containing 2-20 carbon atoms and "substituted hydrocarbyloxycarbonyl" refers to hydrocarbyloxycarbonyl groups further bearing one or more substituents as set forth herein.

As used herein, the term "hydrocarbylcarbonyloxy" refers to —O—C(O)-hydrocarbyl groups 2-20 carbon atoms and "substituted hydrocarbylcarbonyloxy" refers to hydrocarbylcarbonyloxy groups further bearing one or more substituents as set forth herein.

As used herein, the term "hydrocarbylene" refers to any divalent organic radical wherein the backbone thereof comprises carbon and hydrogen only. Thus, hydrocarbylene embraces alkylene, cycloalkylene, alkenylene, cycloalkenylene, alkynylene, arylene, alkylarylene, arylalkylene, arylalkenylene, alkenylarylene, arylalkynylene, alkynylarylene, and the like, and "substituted hydrocarbylene" refers to any of the above-referenced hydrocarbylene groups further bearing one or more substituents as set forth herein.

As used herein, the term "hydroxyl" or "hydroxy" refers to the group —OH.

As used herein, the term "organosulfinyl" denotes the group —S(O)-organo, where organo embraces alkyl-, alkoxy-, alkylamino-, and aryl moieties, as well as substituted alkyl-, alkoxy-, alkylamino-, and aryl moieties.

As used herein, the term "organosulfonyl" denotes the group —S(O)$_2$-organo, where organo embraces alkyl-, alkoxy- and alkylamino-moieties, as well as substituted alkyl-, alkoxy- or alkylamino-moieties.

As used herein, the term "oxo" refers to an oxygen substituent double bonded to the attached carbon.

As used herein, the term "sulfinyl" denotes the group —S(O)—.

As used herein, the term "substituted sulfinyl" denotes the group —S(O)R$^t$, where R$^t$ is lower alkyl, substituted lower alkyl, cycloalkyl, substituted cycloalkyl, cycloalkylalkyl, substituted cycloalkylalkyl, heterocyclyl, substituted heterocyclyl, heterocyclylalkyl, substituted hetereocyclylalkyl, aryl, substituted aryl, heteroaryl, substituted heteroaryl, heteroaralkyl, substituted heteroaralkyl, aralkyl, or substituted aralkyl.

As used herein, the term "sulfonyl" denotes the group —S(O)$_2$—.

As used herein, the term "substituted sulfonyl" denotes the group —S(O)$_2$R$^t$, where R$^t$ is lower alkyl, substituted lower alkyl, cycloalkyl, substituted cycloalkyl, cycloalkylalkyl, substituted cycloalkylalkyl, heterocyclyl, substituted heterocyclyl, heterocyclylalkyl, substituted hetereocyclylalkyl, aryl, substituted aryl, heteroaryl, substituted heteroaryl, heteroaralkyl, substituted heteroaralkyl, aralkyl, or substituted aralkyl.

As used herein, the term "sulfonylamino" denotes the group —NR$^q$S(O)$_2$— where R$^q$ is hydrogen or lower alkyl.

As used herein, the term "substituted sulfonylamino" denotes the group —NR$^q$S(O)$_2$R$^u$, where R$^q$ is hydrogen or lower alkyl and R$^u$ is lower alkyl, substituted lower alkyl, cycloalkyl, substituted cycloalkyl, heterocyclyl, substituted heterocyclyl, aryl, substituted aryl, heteroaryl, substituted heteroaryl, heteroaralkyl, substituted heteroaralkyl, aralkyl, or substituted aralkyl.

As used herein, the term "sulfuryl" denotes the group —S(O)$_2$—.

As used herein in connection with numerical values, the term "approximately" or "about" means 30% of the indicated value.

BRIEF DESCRIPTION OF THE FIGURES

represents the substitution group. FIG. 2A shows conversion of a 3'-substituted dNTP containing a 3'-X group to an unsubstituted, active state 3'-OH dNTP. FIG. 2B shows conversion of "terminated primer" containing a 3'-X substitution group to an unsubstituted extendable primer.

DETAILED DESCRIPTION OF THE INVENTION

A nucleic acid replication reaction such as PCR involves (a) hybridization of an oligonucleotide primer to a target nucleic acid followed by (b) incorporation of nucleoside 5'-triphosphates (NTPs) into an oligonucleotide by a nucleic acid polymerase to form at least one copy, preferably multiple copies of a target sequence. However, the replication reaction often yields unwanted products due to mis-priming and primer dimer formation which affect efficiency and accuracy of the procedure and possible downstream procedures. Many unwanted products are produced during sample preparation and the initial temperature increase (initial denaturation step) of an replication reaction.

The methods and compositions herein provide improved methods and compositions for nucleic acid replication. In particular aspects, the methods and compositions are directed to the use of NTPs in temperature dependent nucleic acid replication reactions. In other aspects, the process of nucleic acid replication employs one or more 3'-substituted NTPs with a heat-removable modification group preferably at the 3'-position of a sugar, the presence of which impairs the formation of undesired amplification products.

In one aspect, provided herein is a method of replicating nucleic acids using at least one modified NTP, where the modified NTP includes one or more modification groups with at least one substitution group at the 3'-position. In some preferred embodiments, the substitution group at the 3'-position converts to a 3'-OH group or dissociates from the NTP during the initial denaturation step of the replication reaction. For example, the initial denaturation step occurs at about 42-70° C. for 10-100 minutes in a reverse transcriptase reaction and at about 94° C., 95° C., 96° C. or 100° C. for 3-30 minutes for PCR reactions. One of skill in the art would be able to determine the parameters in which the initial denaturation step occurs based on the replication application being performed with the 3'-substituted NTPs provided herein.

Figure 1:
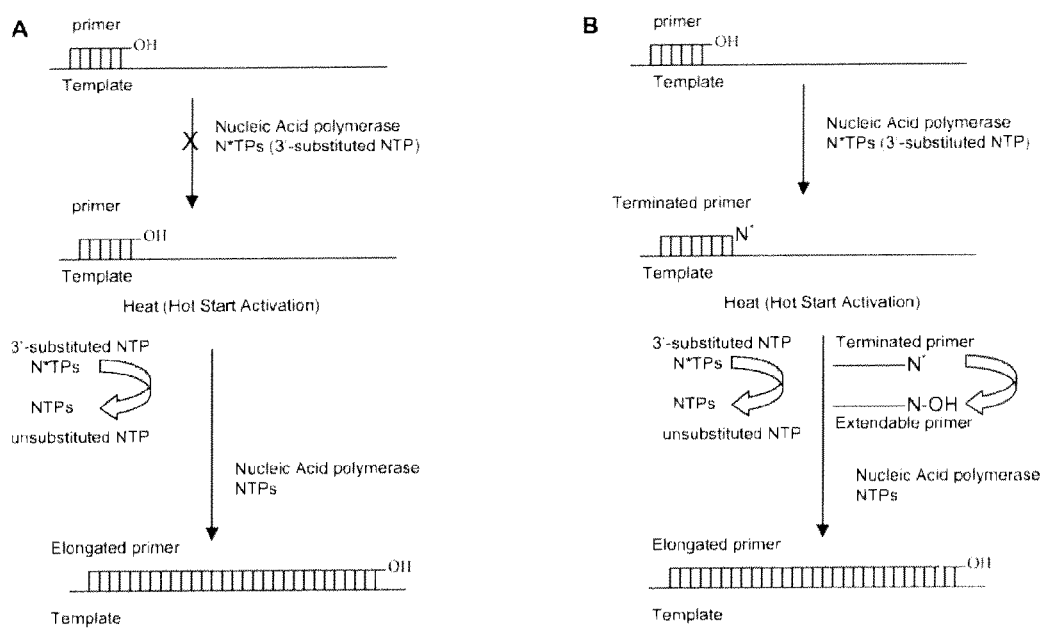
FIGS. 1A and 1B are schematic representations of two mechanisms illustrating how nucleic acid polymerase mediated primer extension can be impaired by a 3'-substituted dNTP prior to Hot Start activation.
Figure 2:
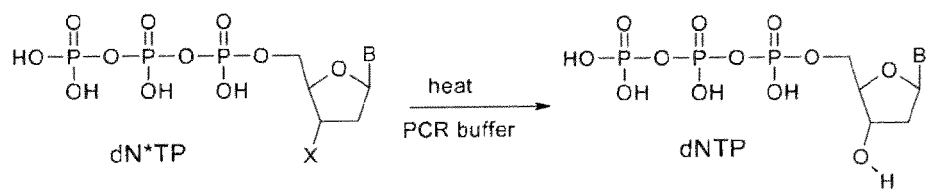
FIGS. 2A and 2B are schematic representations of exemplary schemes for thermally induced Hot Start activation. "X"
Figure 2:
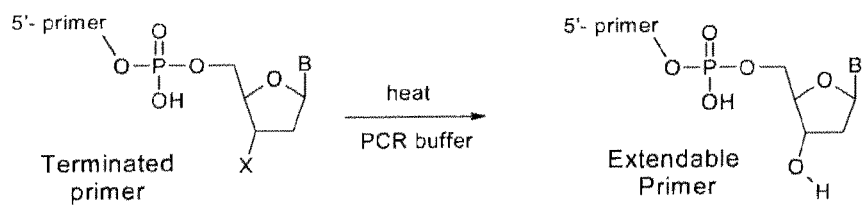

In preferred embodiments, the methods and compositions herein provide a 3'-substituted NTP, where the NTP possesses one or more modification groups, where at least one modification is at the 3'-position (i.e., a 3'-substituted NTP). According to one mechanism, the 3'-substituted NTP is a non substrate NTP and cannot be used as a substrate by nucleic acid polymerase (FIG. 1A). Therefore, the 3'-substituted NTP is not incorporated into an oligonucleotide or polynucleotide chain until the 3'-substitution group is removed or otherwise converted to a free hydroxyl group. In a second mechanism, the 3'-substituted NTP is a terminating NTP and can be incorporated by nucleic acid polymerase to elongate a polynucleotide or oligonucleotide primer by one modified nucleoside unit at the 3'-position, producing a terminated primer (FIG. 1B). Accordingly, further chain extension of the terminated primer is prevented unless and until the 3'-substitution group is removed, or otherwise converted to a free hydroxyl group, to generate an extendable primer. Therefore, the 3'-substitution of the NTP impairs nucleic acid polymerase mediated primer extension prior to the initial incubation period at an elevated temperature of replication such as in the initial denaturation step of PCR, which is preferably at about 95° C. for 1-120 minutes. Upon reaching a desired temperature, e.g., high temperatures, the terminated primer becomes an extendable primer by thermally induced intra- or/and intermolecular fragmentation which removes the 3'-substitution group, or otherwise converts the 3'-substitution group in to an open (i.e., unmodified) 3'-hydroxyl group. The extendable primer possessing an open 3'-hydroxyl group (3'-OH) and can be efficiently elongated by nucleic acid polymerase.

Partial conversion (e.g., from a fraction of all modified molecules) or complete conversion (e.g., from all modified molecules) of the 3'-substitution groups provided herein to 3'-hydroxyl groups preferably occurs after incubation at approximately 95° C. within 1-120 minutes, preferably within 1-30 minutes, preferably within 1-15 minutes, preferably within 1-10 minutes, more preferably within 1-5 minutes, and more preferably within 1-2 minutes. In certain embodiments, conversion of the 3'-substituted NTP or terminated primer to an active state occurs in respect to temperature and does not require enzymes, additional chemicals, or modified polymerization reaction conditions but can be used in conjunction with them. In certain embodiments, the replication reaction does not include any additional substances. Examples of additional substances include, but are not limited to chemical compounds and enzymes. In particular embodiments, additional substances not included in a replication reaction are chemical cleaving reagents such as those used in the art to remove 3'-substitution groups (e.g., palladium catalyst in neutral aqueous solution at elevated temperature (see e.g., Ju, et al., U.S. Pat. No. 6,664,079; Meng, Q., et al, 78 J. Org. Chem., 3248-3252 (2006); and Bi, L., et al., 128 J. Amer. Chem. Soc., 2542-2543 (2006)), hydrochloric acid to pH 2 (see e.g., Tsien, R. Y, WO 91/06678), a reducing agent such as mercaptoethanol (see e.g., Kwiatkowski, M., U.S. Pat. No. 7,279,563) or by the addition of tris-(2-carboxyethyl)phosphine (see e.g., Milton, J., et al, U.S. Pat. No. 7,414,116). In particular embodiments, removal of the 3'-substitution group is not by UV irradiation (see e.g., Dower, et al., WO 92/10587). In some embodiments, the replication reaction does not include chemical cleavage of the 3'-substitution group (e.g., by a cleaving enzyme). In other embodiments, the replication reaction is a sequencing reaction that does not include any additional substances, preferably the additional substance not included in the replication reaction is a cleaving agent. In some other embodiments, the replication reaction is not sequencing by step-wise synthesis (e.g., linear replication of a target sequence).

In one aspect, 3'-substituted NTPs and derivatives thereof in accordance with the invention provide compounds of Formula IA:

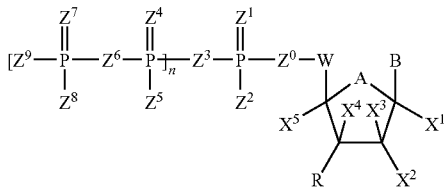

wherein:
n is 0 or 1;
B is selected from a substituted or non-substituted purine or pyrimidine, any aza or deaza derivative thereof, or any "universal base" or "degenerate base" of any NTP analog, which is preferably recognizable by a nucleic acid polymerase;
A is selected from the group consisting of O, S, Se, $CR^1R^2$, and $NR^1$;
W is selected from the group consisting of O, S, Se, $CR^1R^2$, and $NR^1$;
each $R^1$ and each $R^2$ is independently selected from the group consisting of H, F, Cl, Br, I, $OR^3$, $SR^3$, $SeR^3$, $NR^3R^4$, $C(Y)R^5$, and substituted or non-substituted alkyl, alkenyl, alkynyl, aryl, and aralkyl,
wherein any substituent may each optionally contain one or more heteroatoms;
each $R^3$ and each $R^4$ is independently selected from the group consisting of H or substituted or non-substituted alkyl, alkenyl, alkynyl, aryl, and aralkyl,
wherein any substituent may each optionally contain one or more heteroatoms;
each $R^5$ is selected from the group consisting of H, F, Cl, Br, $OR^3$, $SR^3$, $SeR^3$, $NR^3R^4$, $C(Y)R^3$ and substituted or non-substituted alkyl, alkenyl, alkynyl, aryl, and aralkyl,
wherein any substituent may each optionally contain one or more heteroatoms;
each Y is selected from the group consisting of O, S, Se, $CR^1R^2$, and $NR^1$;
$Z^1$, $Z^4$ and $Z^7$ are each independently selected from the group consisting of O, S, Se, $CR^1R^2$, and $NR^1$;
$Z^0$ and $Z^6$ are each independently selected from the group consisting of O, S, Se, $O_2$, $CR^1R^2$, $NR^1$, and $C(Y)$;
$Z^3$ is selected from the group consisting of O, S, Se, $O^2$, $CR^1R^2$, $NR^1$, $C(Y)$, a 3'-O-oligonucleotidyl residue, and an oligonucleotide primer,
wherein when n is 0, $Z^3$ is a 3'-O-oligonucleotidyl residue or an oligonucleotide primer, and
wherein when n is 1, $Z^3$ is O, S, Se, $O_2$, $CR^1R^2$, $NR^1$, or $C(Y)$;
$Z^2$, $Z^5$, and $Z^8$ are each independently selected from the group consisting of H, F, $OR^3$, $SR^3$, $SeR^3$, $NR^3R^4$, $NR^3OR^3$, $NR^3$—$NR^3R^4$, CN, $N_3$, $(BH_3)^-M^+$, and $C(Y)R^5$;
$Z^9$ is selected from the group consisting of H, F, $OR^3$, $SR^3$, $SeR^3$, $NR^3R^4$, $NR^3OR^3$, $NR^3$—$NR^3R^4$, CN, $N_3$, $(BH_3)^-M^+$, $C(Y)R^5$, and phosphate;
$Z^{10}$ is selected from the group consisting of O, S, and Se;
$M^+$ is a cation;

$X^1$, $X^2$, $X^3$, $X^4$ and $X^5$ are each independently selected from the group consisting of $R^1$, $NR^3OR^3$, $NR^3$—$NR^3R^4$, CN, $N_3$, NO, $NO_2$, NCO, NCS, OCN, SCN, and $SSR^3$;
R is selected from the group consisting of

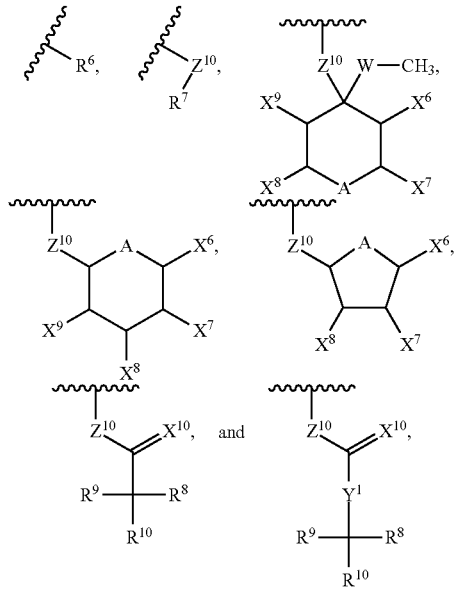

R may be optionally covalently attached through appropriate atoms or group of atoms to $X^1$, $X^2$, $X^3$, $X^4$, $X^5$, $Z^0$, $Z^1$, $Z^2$, $Z^3$, $Z^4$, $Z^5$, $Z^6$, $Z^7$, $Z^8$, $Z^9$, A, W, or B portion of the NTP molecule depicted in Formula IA, each $R^6$ is independently selected from the group consisting of inorganic acid residue, or derivative thereof, with the exception of carbonic acid, where the derivatives may include but are not limited to halogen, sulfonate, thiosulfonate, seleno-sulfate, seleno-sulfonate, sulfate ester, sulfate thioester, sulphite, sulphinate, sulphinic ester, nitrate, nitrite, phosphorus, selenium and boron containing acids;

each $R^7$, each $R^8$, each $R^9$, and each $R^{10}$ is independently selected from the group consisting of hydrogen, and a straight or branched optionally substituted hydrocarbyl group having from 1-20 carbon atoms, preferably 1-10 carbon atoms, preferably 1-6 carbon atoms, wherein the hydrocarbyl is alkyl, alkenyl or alkynyl which may optionally include at least one substituent selected from the group consisting of halo, oxo, hydroxyl, alkoxy, amino, amido, cycloalkyl, heterocycloalkyl, aryl, aryloxy, and heteroaryl;

each $X^6$, each $X^7$, each $X^8$, and each $X^9$ is independently selected from any substituted or unsubstituted group consisting of acyl, acyloxy, alkenyl, alkenylaryl, alkenylene, alkyl, lower alkyl, alkylene, alkynyl, alkynylaryl, alkoxy, lower alkoxy, alkylaryl, alkylcarbonylamino, alkylsulfinyl, alkylsulfonyl, alkylsulfonylamino, alkylthio, alkynylene, amido, amidino, amino, arylalkynyl, aralkyl, aroyl, arylalkyl, aryl, arylcarbonylamino, arylene, aryloxy, arylsulfonylamino, carbamate, dithiocarbamate, cycloalkenyl, cycloalkyl, cycloalkylene, guanidinyl, halo, halogen, heteroaryl, heteroarylcarbonylamino, heteroaryloxy, heteroarylsulfonylamino, heterocycle, heterocycle, hydrocarbyl, hydrocarbyl, hydrocarbylcarbonyl, hydrocarbyloxycarbonyl, hydrocarbylcarbonyloxy, hydrocarbylene, organosulfinyl, hydroxyl, organosulfinyl, organosulfonyl, sulfinyl, sulfonyl, sulfonylamino, and sulfuryl;

each $X^{10}$ is independently selected from the group consisting of O, S, Se, $NR^{11}$, $N-OR^{11}$, and $CR^{11}R^{12}$;

each $R^{11}$ and each $R^{12}$ is independently selected from any substituted or unsubstituted group consisting of acyl, acyloxy, alkenyl, alkenylaryl, alkenylene, alkyl, lower alkyl, alkylene, alkynyl, alkynylaryl, alkoxy, lower alkoxy, alkylaryl, alkylcarbonylamino, alkylsulfinyl, alkylsulfonyl, alkylsulfonylamino, alkylthio, alkynylene, amido, amidino, amino, arylalkynyl, aralkyl, aroyl, arylalkyl, aryl, arylcarbonylamino, arylene, aryloxy arylsulfonylamino carbamate, dithiocarbamate, cycloalkenyl, cycloalkyl, cycloalkylene, guanidinyl, halo, halogen, heteroaryl, heteroarylcarbonylamino, heteroaryloxy, heteroarylsulfonylamino, heterocycle, heterocycle, hydrocarbyl, hydrocarbyl, hydrocarbylcarbonyl, hydrocarbyloxycarbonyl, hydrocarbylcarbonyloxy, hydrocarbylene, organosulfinyl, hydroxyl, organosulfinyl, organosulfonyl, sulfinyl, sulfonyl, sulfonylamino, and sulfuryl; and each $Y^1$ is independently selected from the group consisting of O, S, Se, $NR^6$, $N-OR^6$, and $CR^6R^7$.

In certain embodiments of Formula IA, B is thymine, cytosine, adenine, guanine, uracil, aminoallyl-uracil, 7-deazaguanine, 7-deaza-7-methylguanine, 7-deaza-7-iodoguanine, 7-deaza-7-aminoallyl-guanine, 7-deaza-8-azaguanine, 7-deazadenine, 2,6-diaminopurine, 5-nitro-cytosine, 5-aminoallyl-cytosine, 5-(Biotin-16)-cytosine, 5-(Fluorescein-11)-cytosine, 4-methylamino-cytosine, 2-thio-5-methyluracil, or 4-thio-5-methyluracil.

In preferred embodiments of Formula IA, B is adenine, guanine, cytosine, thymine, or uracil.

In certain embodiments of Formula IA, $X^1$, $X^3$, and $X^4$ are H; W is $CH^2$; $Z^0$, $Z^1$, $Z^6$ and $Z^7$ are O; and $Z^5$ and $Z^8$ are OH, as shown below.

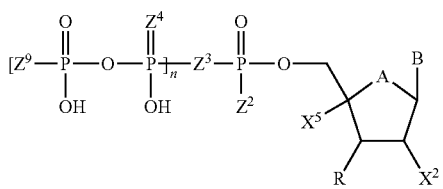

In certain embodiments of Formula IA, A is NH, O, $CH^2$, or S; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; and $Z^2$, $Z^5$, $Z^8$ and $Z^9$ are OH, as shown below.

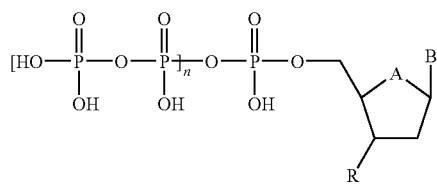

In certain embodiments of Formula IA, $X^2$ is H, OH, F, $CH_3$, $OCH_3$, $N^3$, $NH^2$ or $NHCH_3$; A is O; $X^1$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH, as shown below.

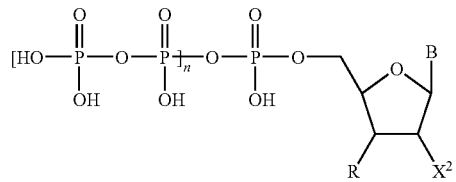

In certain embodiments of Formula IA, $X^5$ is H, SH, $CH_3$, F, $OCH_3$, $NH_2$, or $NHCH_3$; A is O; $X^1$, $X^2$, $X^3$ and $X^4$ are H; W is $CH_2$; $Z^0$, $Z^1$, $Z^3$, $Z^4$, $Z^6$ and $Z^7$ are O; and $Z^2$, $Z^5$, $Z^8$ and $Z^9$ are OH, as shown below.

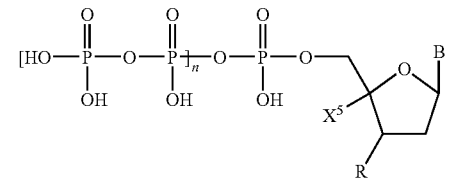

In certain embodiments of Formula IA, $Z^2$ is OH, SH, $BH_3$, $CH_3$, $OCH_3$ or $OCH_2CH_3$; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; and $Z^5$, $Z^8$ and $Z^9$ are OH, as shown below.

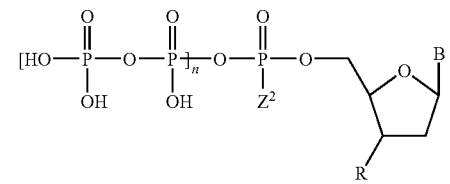

In certain embodiments of Formula IA, $Z^4$ is O or S; n is 1; A is O; $X^1$, $X^2$, $X^3$, $X^4$ and $X^5$ are H; W is $CH_2$; $Z^0$, $Z^1$, $Z^3$, $Z^6$ and $Z^7$ are O; and $Z^2$, $Z^5$, $Z^8$ and $Z^9$ are OH, as shown below.

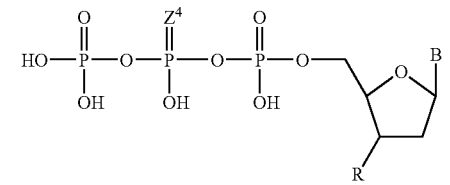

In certain embodiments of Formula IA, $Z^9$ is SH, $SCH_2CH_2CN$, OH, F, $OCH_3$, $OCH_2CH_3$, $OC_6H_5$, $NHCH_3$, $NH_2$, $NHCH_2CH_2NH_2$, $NHCH_2CH_2CH_2CH_2CH_2CH_2NH_2$ or phosphate groups; n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; and $Z^2$, $Z^5$ and $Z^8$ are OH, as shown below.

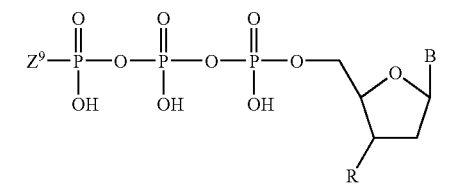

In certain embodiments of Formula IA, n is 1; A is O; $X^1$, $X^2$, $X^3$, $X^4$ and $X^5$ are H; W is $CH_2$, $Z^0$, $Z^1$, $Z^3$, $Z^4$, $Z^6$ and $Z^7$ are O; and $Z^2$, $Z^5$, $Z^8$, and $Z^9$ are OH, as shown below.

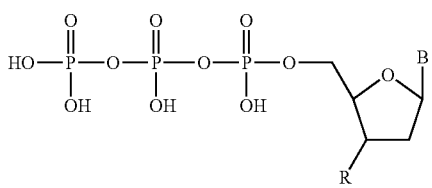

Certain preferred embodiments of Formula IA are as follows (top to bottom, left to right). In one preferred embodiment of Formula IA, n is 1; A is S; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O-(p-toluene)sulfonate. In another preferred embodiment of Formula IA, n is 1; A is O; $X^1$, $X^3$, $X^4$ and $X^5$ are H; $X^2$ is O—$CH_3$; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O-(p-toluene)sulfonate. In another preferred embodiment of Formula IA, n is 1; A is O; $X^1$, $X^2$, $X^3$ and $X^4$ are H; $X^5$=$CH_3$; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O-(p-toluene)sulfonate. In another preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$ is SH; $Z^5$, $Z^8$ and $Z^9$ are OH; and R is O-(p-toluene)sulfonate. In another preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^6$ and $Z^7$ are O; $Z^2$, $Z^5$, $Z^8$ and $Z^9$ are OH; $Z^4$ is S; and R is O-(p-toluene)sulfonate. In another preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$ and $Z^8$ are OH; $Z^9$ is SH; and R is O-(p-toluene)sulfonate.

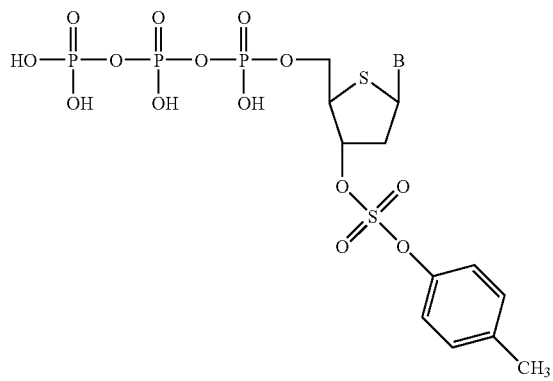

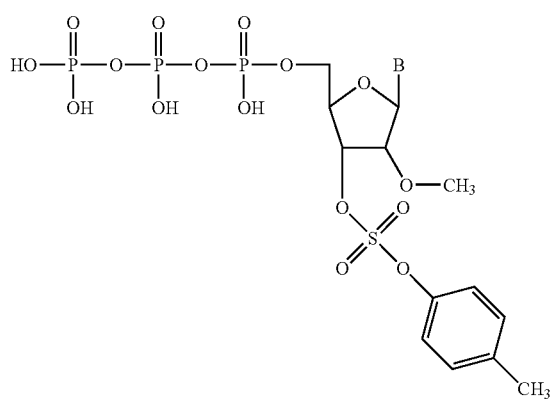

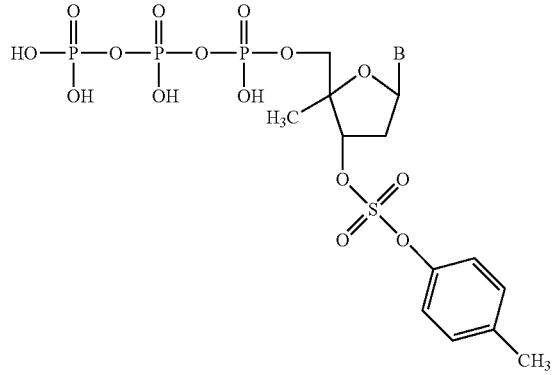

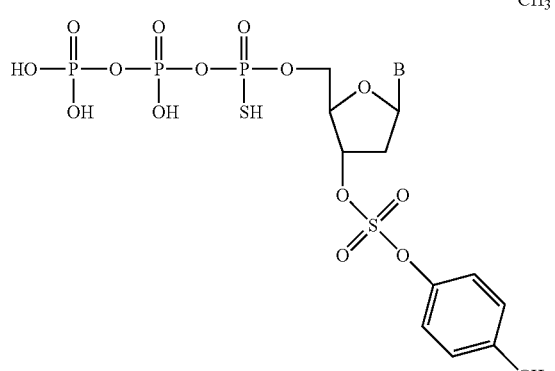

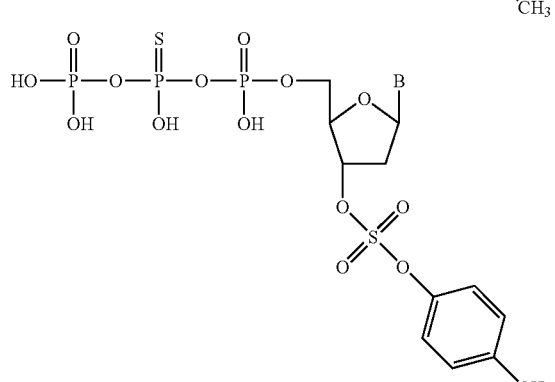

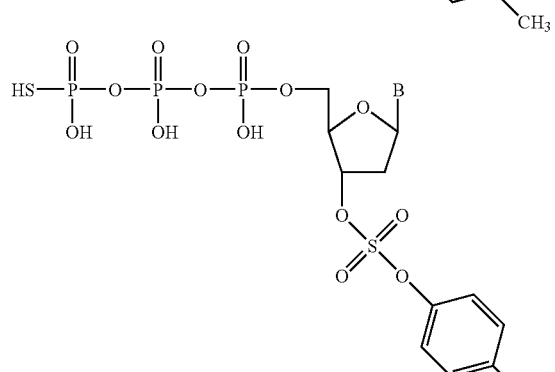

Even more preferred embodiments of Formula are as shown as follows. In one preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O-(p-toluene)sulfonate. In another preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O-phosphate. In another preferred embodiment of Formula IA, n is 1; A is O; $X^1, X^2, X^3, X^4$ and $X^5$ are H; W is $CH_2$; $Z^0, Z^1, Z^3, Z^4, Z^6$ and $Z^7$ are O; $Z^2, Z^5, Z^8$ and $Z^9$ are OH; and R is O-nitrate.

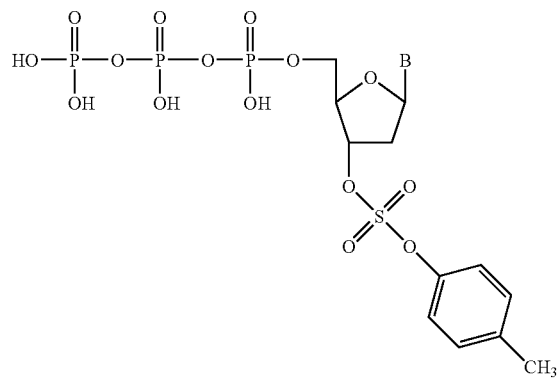

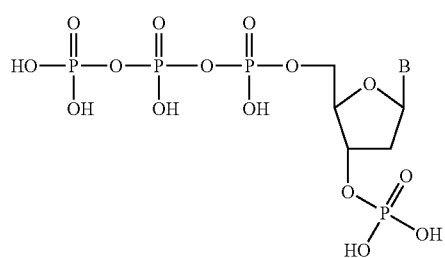

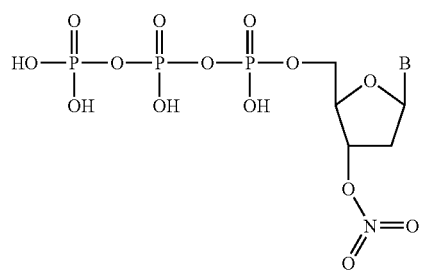

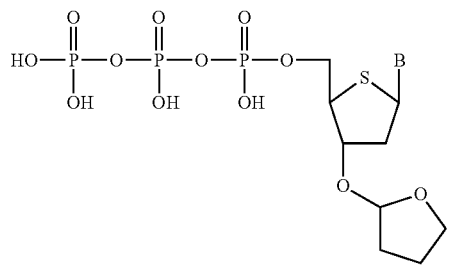

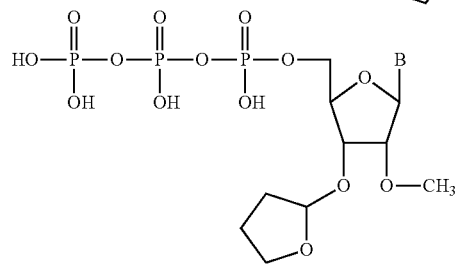

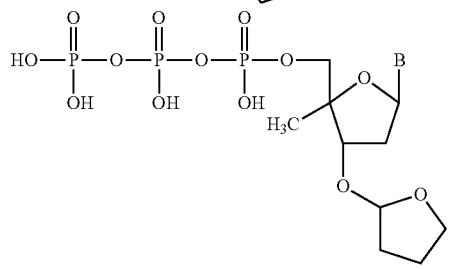

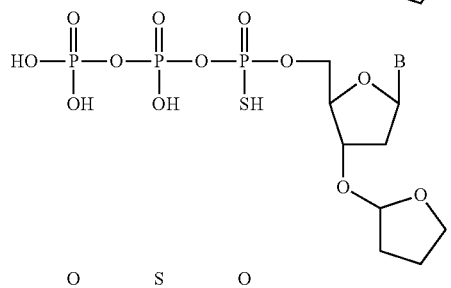

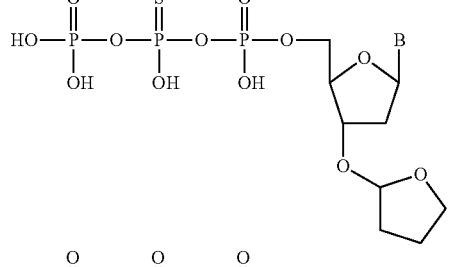

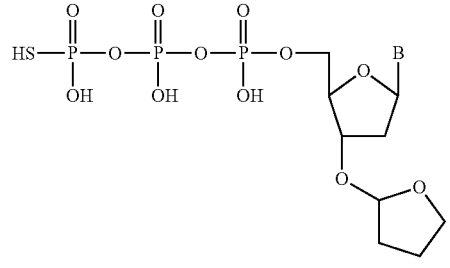

Certain preferred embodiments of Formula IA are shown as follows (left to right, top to bottom). In one preferred embodiment of Formula IA, n is 1; A is S, $X^1, X^2, X^3, X^4$ and $X^5$ are H; W is $CH_2$; $Z^0, Z^1, Z^3, Z^4, Z^6$ and $Z^7$ are O; $Z^2, Z^5, Z^8$ and $Z^9$ are OH; and R is O-tetrahydrofuranyl. In another preferred embodiment of Formula IA, n is 1; A is O; $X^1, X^3, X^4$ and $X^5$ are H; $X^2$ is O—$CH_3$; W is $CH_2$; $Z^0, Z^1, Z^3, Z^4, Z^6$ and $Z^7$ are O; $Z^2, Z^5, Z^8$ and $Z^9$ are OH; and R is O-tetrahydrofuranyl. In another preferred embodiment of Formula IA, n is 1; A is O; $X^1, X^2, X^3$ and $X^4$ and H; $X^5$=$CH_3$; W is $CH_2$; $Z^0, Z^1, Z^3, Z^4, Z^6$ and $Z^7$ are O; $Z^2, Z^5, Z^8$ and $Z^9$ are OH; and R is O-tetrahydrofuranyl. In another preferred embodiment of Formula IA, n is 1; A is O; $X^1, X^2, X^3, X^4$ and $X^5$ are H; W is $CH_2$; $Z^0, Z^1, Z^3, Z^4, Z^6$ and $Z^7$ are O; $Z^2$ is SH; $Z^5, Z^8$ and $Z^9$ are OH; and R is O-tetrahydrofuranyl. In another preferred embodiment of Formula IA, n is 1; A is O; $X^1, X^2, X^3, X^4$ and $X^5$ are H; W is $CH_2$; $Z^0, Z^1, Z^3, Z^6$ and $Z^7$ are O; $Z^2, Z^5, Z^8$ and $Z^9$ are OH; $Z^4$ is S; and R is O-tetrahydrofuranyl. In another preferred embodiment of Formula IA, n is 1; A is O; $X^1, X^2, X^3, X^4$ and $X^5$ are H; W is $CH_2$; $Z^0, Z^1, Z^3, Z^4, Z^6$ and $Z^7$ are O; $Z^2, Z^5$ and $Z^8$ are OH; $Z^9$ is SH; and R is O-tetrahydrofuranyl.

Certain preferred embodiments of Formula IA are shown below (left to right, top to bottom). In one preferred embodiment of Formula IA, n is 1; A is O; $X^1, X^2, X^3, X^4$ and $X^5$ are H; W is $CH_2$; $Z^0, Z^1, Z^3, Z^4, Z^6$ and $Z^7$ are O; $Z^2, Z^5, Z^8$ and $Z^9$ are OH; and R is O-[4-methoxyl]-tetrahydropyranyl. In another preferred embodiment of Formula IA, n is 1; A is O;

$X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O-tetrahydropyranyl. In another preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O-tetrahydrofuranyl. In another preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O-[4-methoxy]-tetrahydrothiopyranyl. In another preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O-tetrahydrothiopyranyl. In another preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O-[5-methyl]-tetrahydrofuranyl. In another preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O-[2-methyl, 4-methoxy]-tetrahydropyranyl. In another preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O-[5-methyl]-tetrahydropyranyl. In another preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O-tetrahydrothiofuranyl.

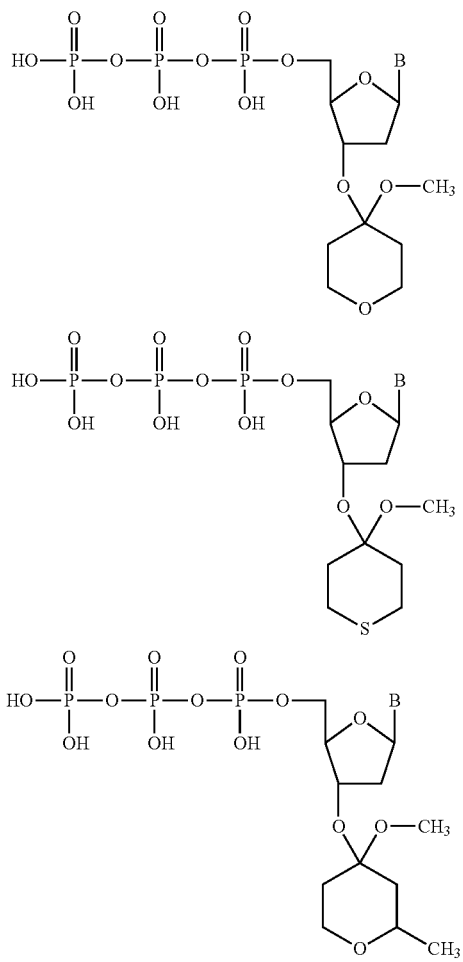

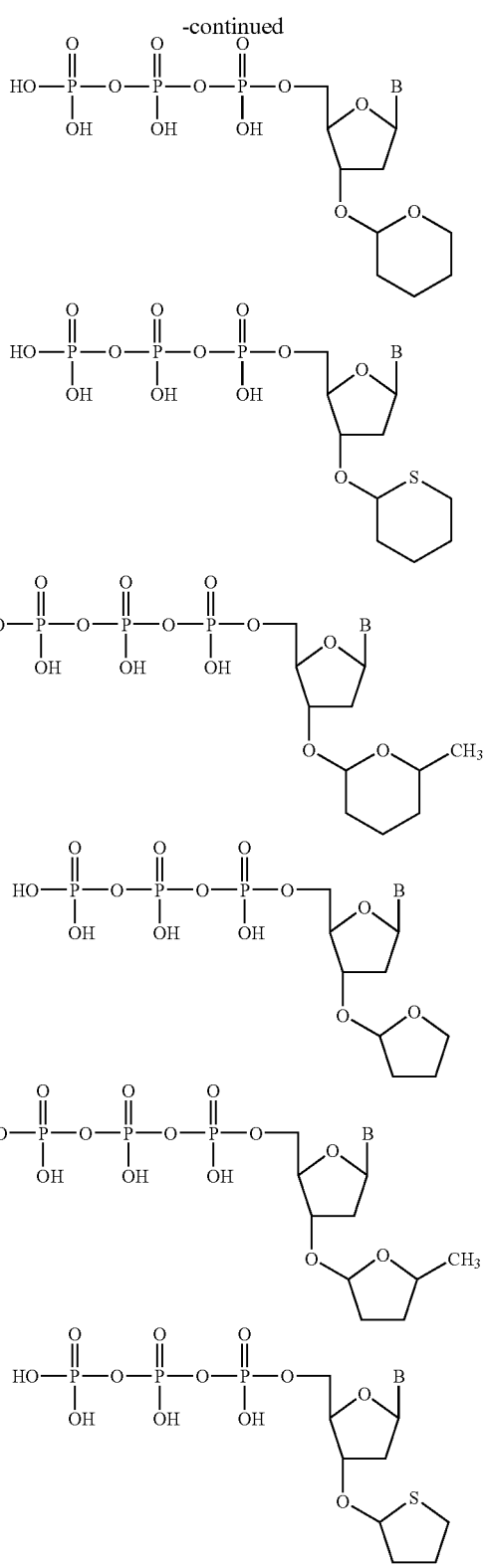

Even more preferred embodiments of Formula IA are as follows. In one preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O-[4-methoxy]-tetrahydropyranyl. In another preferred embodiment of Formula IA, n is 1; A is O; $X^1$, $X^2$, $X^3$, $X^4$ and $X^5$ are H; W is $CH_2$; $Z^0, Z^1, Z^3, Z^4, Z^6$ and $Z^7$ are O; $Z^2, Z^5, Z^8$ and $Z^9$ are OH; and R is O-tetrahydropyranyl. In another preferred embodiment of Formula IA, n is 1; A is O; $X^1, X^2, X^3, X^4$ and $X^5$ are H; W is $CH_2$; $Z^0, Z^1, Z^3, Z^4, Z^6$ and $Z^7$ are O; $Z^2, Z^5, Z^8$ and $Z^9$ are OH; and R is O-tetrahydrofuranyl.

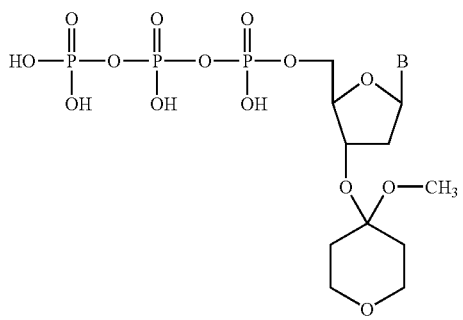

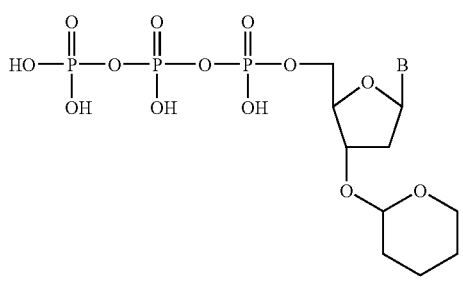

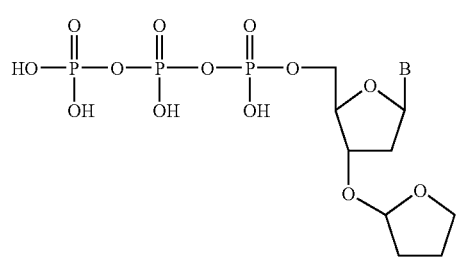

Certain preferred embodiments of Formula IA are shown below (left to right, top to bottom). In one preferred embodiment of Formula IA, n is 1; A is S; $X^1, X^2, X^3, X^4$ and $X^5$ are H; W is $CH_2$; $Z^0, Z^1, Z^3, Z^4, Z^6$ and $Z^7$ are O; $Z^2, Z^5, Z^8$ and $Z^9$ are OH; and R is O-phenoxyacetyl. In another preferred embodiment of Formula IA, n is 1; A is O; $X^1, X^2, X^3, X^4$ and $X^5$ are H; $X^2$ is O—$CH_3$; W is $CH_2$; $Z^0, Z^1, Z^3, Z^4, Z^6$ and $Z^7$ are O; $Z^2, Z^5, Z^8$ and $Z^9$ are OH; and R is O-phenoxyacetyl. In another preferred embodiment of Formula IA, n is 1; A is O; $X^1, X^2, X^3$ and $X^4$ are H; $X^5$ is $CH_3$; W is $CH_2$; $Z^0, Z^1, Z^3, Z^4, Z^6$ and $Z^7$ are O; $Z^2, Z^5, Z^8$ and $Z^9$ are OH; and R is O-phenoxyacetyl. In another preferred embodiment of Formula IA, n is 1; A is O; $X^1, X^2, X^3, X^4$ and $X^5$ are H; W is $CH_2$; $Z^0, Z^1, Z^3, Z^4, Z^6$ and $Z^7$ are O; $Z^5, Z^8$ and $Z^9$ are OH; $Z^2$ is SH; and R is O-phenoxyacetyl. In another preferred embodiment of Formula IA, n is 1; A is O; $X^1, X^2, X^3, X^4$ and $X^5$ are H; W is $CH_2$; $Z^0, Z^1, Z^3, Z^6$ and $Z^7$ are O; $Z^4$ is S; $Z^5, Z^8$ and $Z^9$ are OH; and R is O-phenoxyacetyl. In another preferred embodiment of Formula IA, n is 1; A is O; $X^1, X^2, X^3, X^4$ and $X^5$ are H; W is $CH_2$; $Z^0, Z^1, Z^3, Z^4, Z^6$ and $Z^7$ are O; $Z^2, Z^5, Z^8$ are OH; $Z^9$ is SH; and R is O-phenoxyacetyl.

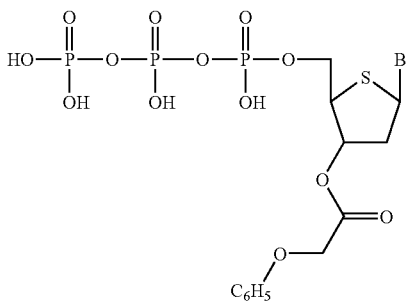

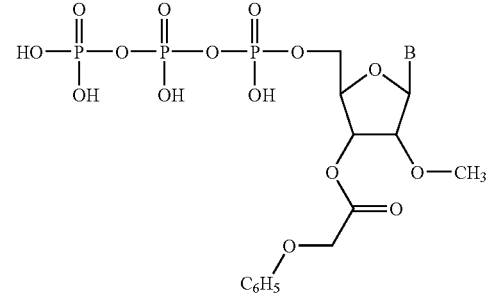

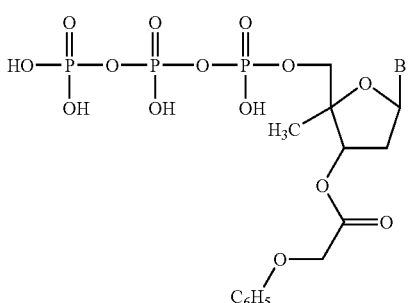

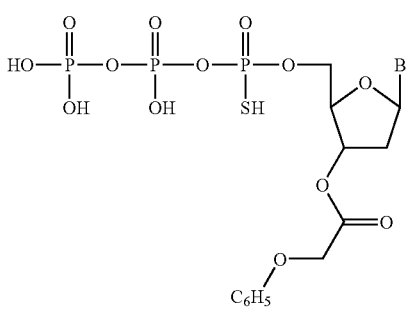

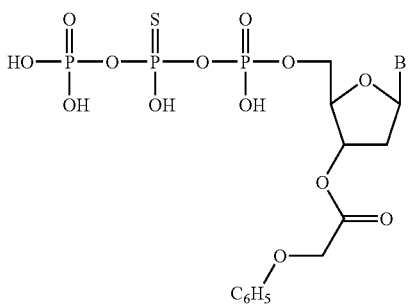

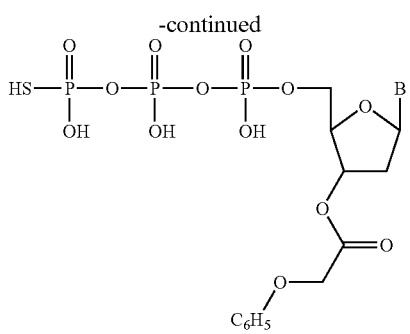

Even more preferred embodiments of Formula IA are shown below. In one preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and OH; and R is O-phenoxyacetyl. In another preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O-methoxyacetyl. In another preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O-acetyl.

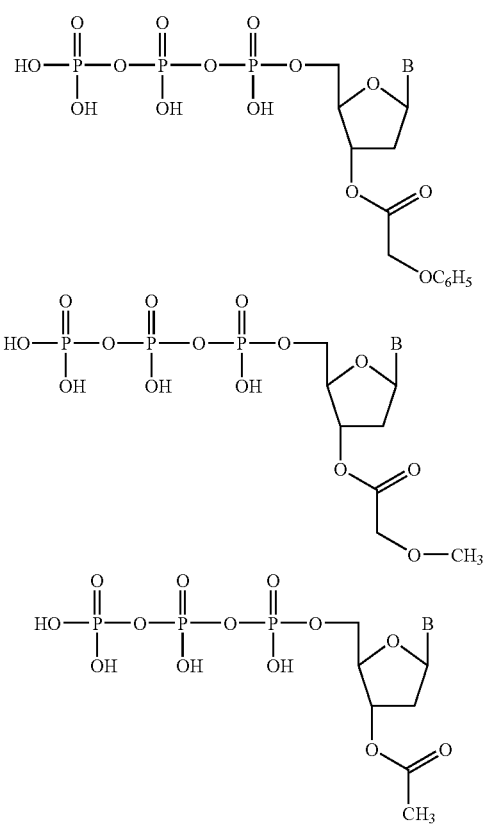

Certain preferred embodiments of Formula IA are shown below (top to bottom, left to right). In one preferred embodiment of Formula IA, n is 1; A is S; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O—C(O)—OCH_3. In another preferred embodiment of Formula IA, n is 1; A is O; $X^1$, $X^3$, $X^4$ and $X^5$ are H; $X^2$ is O—$CH_3$; W is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O—C(O)—OCH_3. In another preferred embodiment of Formula IA, n is 1; A is O; $X^1$, $X^2$, $X^3$ and $X^4$ are H; $X^5$ is $CH_2$; $Z^0$, $Z^1$, $Z^3$, $Z^4$, $Z^6$ and $Z^7$ are O; $Z^2$, $Z^5$, $Z^8$ and $Z^9$ are OH; and R is O—C(O)—OCH_3. In another preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$ is SH; $Z^5$, $Z^8$ and $Z^9$ are OH; and R is O—C(O)—OCH_3. In another preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^6$ and $Z^7$ are O; $Z^4$ is S; $Z^2$, $Z^5$, $Z^8$ and $Z^9$ are OH; and R is O—C(O)—OCH_3. In another preferred embodiment of Formula IA, n is 1; A is O; $X^1$, $X^2$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$ and $Z^8$ are OH; $Z^9$ is SH; and R is O—C(O)—OCH_3.

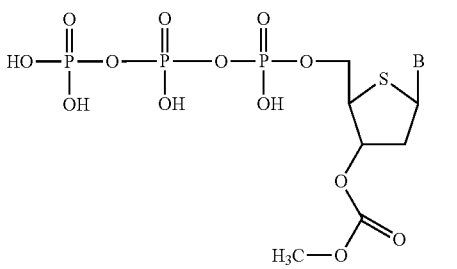

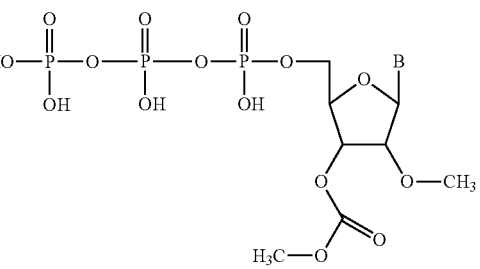

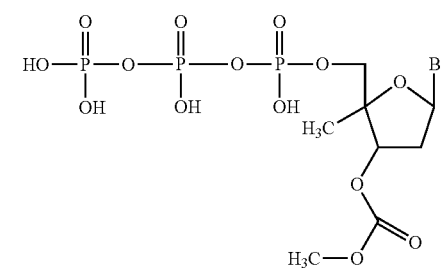

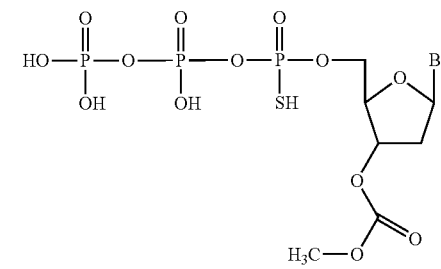

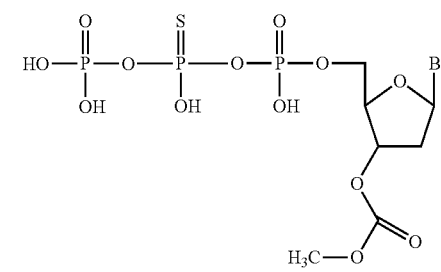

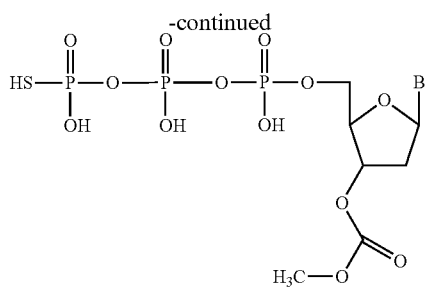

Even more preferred, embodiments of Formula IA are shown below. In one preferred embodiment of Formula IA, n is 1; A is O; $X^1, X^2, X^3, X^4$ and $X^5$ are H; W is $CH_2$; $Z^0, Z^1, Z^3, Z^4, Z^6$ and $Z^7$ are O; $Z^2, Z^5, Z^8$ and $Z^9$ are OH; and R is O—C(O)—$OCH_3$. In another preferred embodiment of Formula IA, n is 1; A is O; $X^1, X^2, X^3, X^4$ and $X^5$ are H; W is $CH_2$; $Z^0, Z^1, Z^3, Z^4, Z^6$ and $Z^7$ are O; $Z^2, Z^5, Z^8$ and $Z^9$ are OH; and R is O—C(O)—$CH_2CH_2CN$. In another preferred embodiment of Formula IA, n is 1; A is O; $X^1, X^2, X^3, X^4$ and $X^5$ are H; W is $CH_2$; $Z^0, Z^1, Z^3, Z^4, Z^6$ and $Z^7$ are O; $Z^2, Z^5, Z^8$ and $Z^9$ are OH; and R is O—C(S)—$OCH_3$.

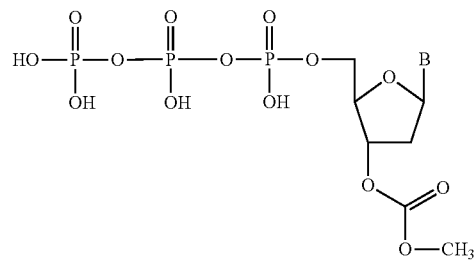

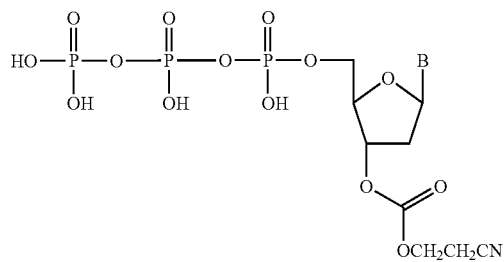

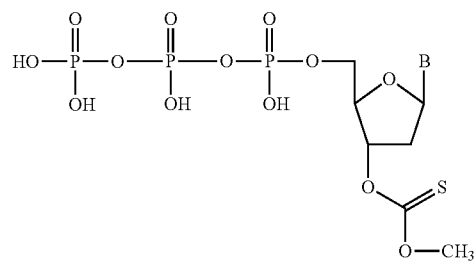

In certain embodiments of Formula IA, n is 0 such that $Z^4, Z^5, Z^6, Z^7, Z^8, Z^9, P^2$, and $P^3$ are not present; and $Z^3$ is a 3'-O-oligonucleotidyl residue or an oligonucleotide primer, thereby providing a "terminated primer".

In one aspect, 3'-substituted NTPs and derivatives thereof, in accordance with the invention provide compounds of Formula IB:

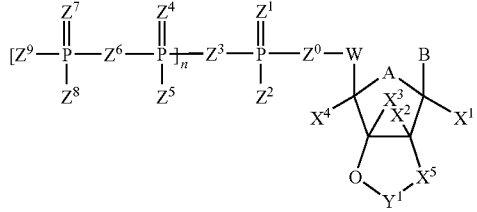

wherein:

n is 0 or 1;

B is selected from a substituted or non-substituted purine or pyrimidine, any aza or deaza derivative thereof, or any "universal base" or "degenerate base" of any NTP analog, which is preferably recognizable by a nucleic acid polymerase;

A is selected from the group consisting of O, S, Se, $CR^1R^2$, and $NR^1$;

W is selected from the group consisting of O, S, Se, $CR^1R^2$, and $NR^1$;

each $R^1$ and each $R^2$ is independently selected from the group consisting of H, F, Cl, Br, I, $OR^3$, $SR^3$, $NR^3R^4$, $C(Y)R^5$, and substituted or non-substituted alkyl, alkenyl, alkynyl, aryl, and aralkyl,
wherein any substituent may each optionally contain one or more heteroatoms;

each Y is independently selected from the group consisting of O, S, Se, $CR^1R^2$ and $NR^1$;

each $R^3$ and each $R^4$ is independently selected from the group consisting of H, substituted or unsubstituted alkyl, substituted or unsubstituted alkenyl, substituted or unsubstituted alkynyl, substituted or unsubstituted aryl, and substituted or unsubstituted aralkyl,
wherein any substituent may each optionally contain one or more heteroatoms;

each $R^5$ is independently selected from the group consisting of H, F, Cl, Br, $OR^3$, $SR^3$, $NR^3R^4$, substituted or unsubstituted substituted or unsubstituted alkyl substituted or unsubstituted alkenyl, substituted or unsubstituted alkynyl, substituted or unsubstituted aryl, and substituted or unsubstituted aralkyl,
wherein any substituent may each optionally contain one or more heteroatoms;

$Z^1, Z^4$ and $Z^7$ are each independently selected from the group consisting of O, S, Se, $CR^1R^2$, and $NR^1$;

$Z^0$ and $Z^6$ are each independently selected from the group consisting of O, S, Se, $O_2$, $CR^1R^2$, $NR^1$, and C(Y);

$Z^3$ is selected from the group consisting of O, S, Se, $O_2$, $CR^1R^2$, $NR^1$, C(Y), a 3'-O-oligonucleotidyl residue, and an oligonucleotide primer,
wherein when n is 0, $Z^3$ is a 3'-O-oligonucleotidyl residue or an oligonucleotide primer, and
wherein when n is 1, $Z^3$ is O, S, Se $O_2$, $CR^1R^2$, $NR^1$, or C(Y);

$Z^2, Z^5$ and $Z^8$ are each independently selected from the group consisting of H, F, $OR^3$, $SR^3$, $SeR^3$, $NR^3R^4$, $NR^3OR^3$, $NR^3$—$NR^3R^4$, CN, $N_3$, $(BH_3)^-M^+$, and $C(Y)R^5$;

$Z^9$ is selected from the group consisting of H, F, $OR^3$, $SR^3$, $SeR^3$, $NR^3R^4$, $NR^3OR^3$, $NR^3$—$NR^3R^4$, CN, $N_3$, $(BH_3)^-M^+$, C(Y), and phosphate;

$M^+$ is a cation;

$X^1, X^2, X^3$ and $X^4$ are each independently selected from the group consisting of $R^1$, F, Cl, Br, I, $OR^3$, $SR^3$, $SeR^3$, $NR^3R^4$, $NR^3OR^3$, $NR^3$—$NR^3R^4$, CN, $N_3$, $C(Y)R^5$, $NO_2$, CN, and $SSR^3$;

$X^5$ is selected from the group consisting of O, S, Se, $NR^6$, $N-OR^6$, and $CR^6R^7$;

$Y^1$ is selected from the group consisting of O, S, Se, $NR^6$, $N-OR^6$, $CR^6R^7$, and C(Y);

each $R^6$ and each $R^7$ is independently selected from the group consisting of hydrogen, and a straight or branched optionally substituted hydrocarbyl group having from 1-20 carbon atoms, preferably 1-10 carbon atoms, preferably 1-6 carbon atoms, wherein the hydrocarbyl is alkyl, alkenyl or alkynyl which may optionally include at least one substituent selected from the group consisting of halo, oxo, hydroxyl, alkoxy, amino, amido, cycloalkyl, heterocycloalkyl, aryl, aryloxy, and heteroaryl; and $X^5$ and $Y^1$ may each be optionally covalently attached through appropriate atoms or group of atoms to $X^1, X^2, X^3, X^4, X^5, Z^0, Z^1, Z^2, Z^3, Z^4, Z^5, Z^6, Z^7, Z^8, Z^9$, A, W, or B portion of the NTP molecule depicted in Formula IB.

In certain embodiments of Formula IB, B is thymine, cytosine, adenine, guanine, uracil, aminoallyl-uracil, 7-deazaguanine, 7-deaza-7-methylguanine, 7-deaza-7-iodoguanine, 7-deaza-7-aminoallyl-guanine, 7-deaza-8-azaguanine, 7-deazadenine, 2,6-diaminopurine, 5-nitro-cytosine, 5-aminoallyl-cytosine, 5-(Biotin-16)-cytosine, 5-(Fluorescein-11)-cytosine, 4-methylamino-cytosine, and 2-thio-5-methyluracil, or 4-thio-5-methyluracil.

In preferred embodiments of Formula IB, B is adenine, guanine, cytosine, thymine, or uracil.

In certain embodiments of Formula IB, A is NH, O, $CH_2$ or S; $X^1, X^2$, and $X^3$ are H; W is $CH_2$; $Z^0, Z^1, Z^6$ and $Z^7$ are O; $Z^5$ and $Z^8$ are OH, as shown below.

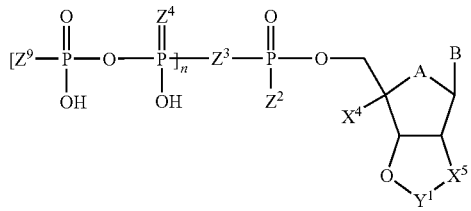

In certain embodiments of Formula IB, A is NH, O, $CH_2$ or S; $X^1, X^2, X^3$ and $X^4$ are H; W is $CH_2$; $Z^0, Z^1, Z^3, Z^4, Z^6$ and $Z^7$ are O; $Z^2, Z^5, Z^8$, and $Z^9$ are OH, as shown below.

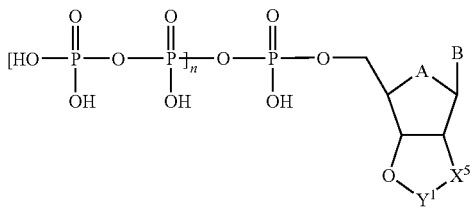

In certain embodiments of Formula IB, $X^4$ is H, SH, $CH_3$, F, $OCH_3$, $NH_2$, or $NHCH_3$; A is O; $X^1, X^2$ and $X^3$ are H; $Z^0, Z^1, Z^3, Z^4, Z^6$ and $Z^7$ are O; $Z^2, Z^5, Z^8$ and $Z^9$ are OH, as shown below.

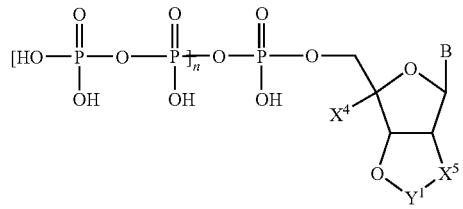

In certain embodiments of Formula IB, $Z^2$ is OH, SH, $BH_3$, $CH_3$, $OCH_3$ or $OCH_2CH_3$; A is O; $X^1, X^2, X^3$ and $X^4$ are H; W is $CH_2$; $Z^0, Z^1, Z^3, Z^4, Z^6$ and $Z^7$ are O; and $Z^5, Z^8$ and $Z^9$ are OH, as shown below.

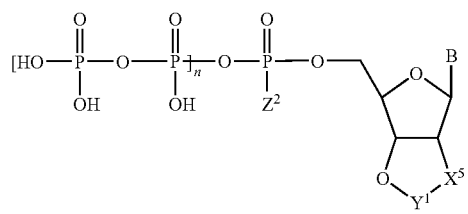

In certain embodiments of Formula IB, $Z^4$ is O or S; n is 1; A is O; $X^1, X^2, X^3$ and $X^4$ are H; W is $CH_2$; $Z^0, Z^1, Z^3, Z^6$ and $Z^7$ are O; $Z^2, Z^5, Z^8$ and $Z^9$ are OH, as shown below

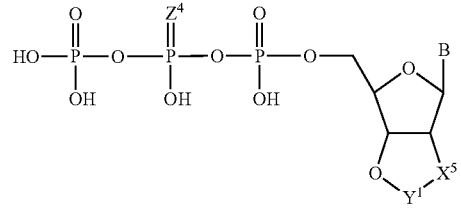

In certain embodiments of Formula IB, $Z^9$ is SH, $SCH_2CH_2CN$, OH, F, $OCH_3$, $OCH_2CH_3$, $NHCH_3$, $NH_2$, $NHCH_2CH_2NH_2$, $NHCH_2CH_2CH_2CH_2CH_2CH_2NH_2$, or a phosphate group; n is 1; A is O; $X^1, X^2, X^3$ and $X^4$ are H; W is $CH_2$; $Z^0, Z^1, Z^3, Z^4, Z^6$ and $Z^7$ are O; $Z^2, Z^5, Z^8$ are OH, as shown below.

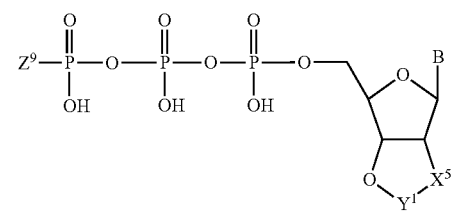

In certain embodiments of Formula IB, n is 1; A is O; $X^1, X^2, X^3$ and $X^4$ are H; W is $CH_2$; $Z^0, Z^1, Z^3, Z^4, Z^6$ and $Z^7$ are O; $Z^2, Z^5, Z^8$ and $Z^9$ are OH, as shown below.

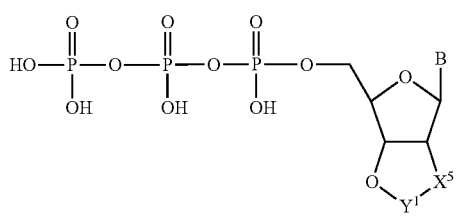

Certain preferred embodiments of Formula IB are as follows (left to right, top to bottom). In one preferred embodiment of Formula IB, n is 1; A is S; $X^1$, $X^2$, $X^3$ and $X^4$ are H; W is $CH_2$; $X^5$, $Z^0$, $Z^1$, $Z^3$, $Z^4$, $Z^6$ and $Z^7$ are O; $Z^2$, $Z^5$, $Z^8$ and $Z^9$ are OH; and $Y^1$ is C=S. In another preferred embodiment of Formula IB, n is 1; A is O; $X^1$, $X^2$ and $X^3$ are H; $X^4$ is $CH_3$; W is $CH_2$; $X^5$, $Z^0$, $Z^1$, $Z^3$, $Z^4$, $Z^6$ and $Z^7$ are O; $Z^2$, $Z^5$, $Z^8$ and $Z^9$ are OH; and $Y^1$ is C=S. In another preferred embodiment of Formula IB, n is 1; A is O; $X^1$, $X^2$, $X^3$ and $X^4$ are H; W is $CH_2$; $X^5$, $Z^0$, $Z^1$, $Z^3$, $Z^4$, $Z^6$ and $Z^7$ are O; $Z^2$, $Z^5$, $Z^8$ and $Z^9$ are OH; and $Y^1$ is C=S. In another preferred embodiment of Formula IB, n is 1; A is O; $X^1$, $X^2$, $X^3$ and $X^4$ are H; W is $CH_2$; $X^5$, $Z^0$, $Z^1$, $Z^3$, $Z^6$ and $Z^7$ are O; $Z^2$, $Z^5$, $Z^8$ and $Z^9$ are OH; $Z^4$ is SH; and $Y^1$ is C=S. In another preferred embodiment of Formula IB, n is 1; A is O; $X^1$, $X^2$, $X^3$ and $X^4$ are H; W is $CH_2$; $X^5$, $Z^0$, $Z^1$, $Z^3$, $Z^4$, $Z^6$ and $Z^7$ are O; $Z^2$, $Z^5$, $Z^8$ are OH; $Z^9$ is SH; and $Y^1$ is C=S.

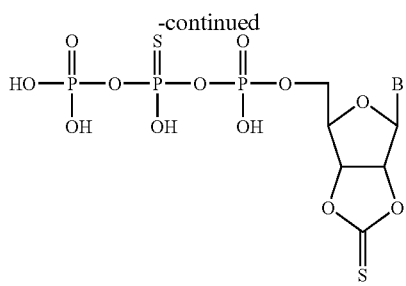

-continued

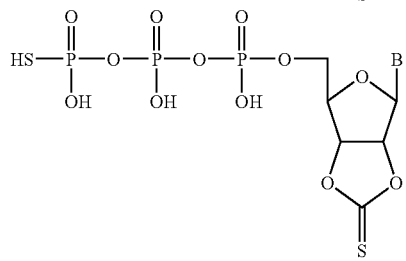

Even more preferred embodiments of Formula IB are as follows. In one preferred embodiment of Formula IB, n is 1; $X^1$, $X^2$, $X^3$ and $X^4$ are H; W is $CH_2$; A, $X^5$, $Z^0$, $Z^1$, $Z^3$, $Z^4$, $Z^6$ and $Z^7$ are O; $Z^2$, $Z^5$, $Z^8$ and $Z^9$ are OH; and $Y^1$ is C=O. In another preferred embodiment of Formula IB, n is 1; $X^1$, $X^2$, $X^3$ and $X^4$ are H; W is $CH_2$; A, $X^5$, $Z^0$, $Z^1$, $Z^3$, $Z^4$, $Z^6$ and $Z^7$ are O; $Z^2$, $Z^5$, $Z^8$ and $Z^9$ are OH; and $Y^1$ is C=S. In another preferred embodiment of Formula IB, n is 1; $X^1$, $X^2$, $X^3$ and $X^4$ are H; $X^5$ is S; W is $CH_2$; A, $Z^0$, $Z^1$, $Z^3$, $Z^4$, $Z^6$ and $Z^7$ are O; $Z^2$, $Z^5$, $Z^8$ and $Z^9$ are OH; and $Y^1$ is C=O.

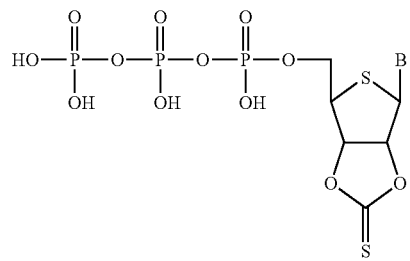

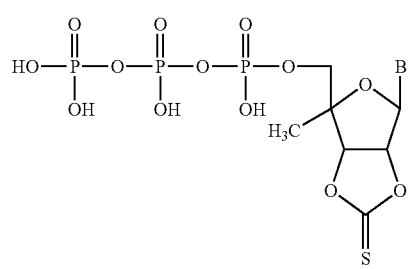

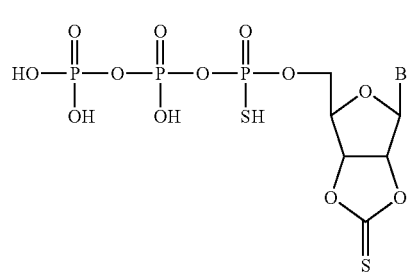

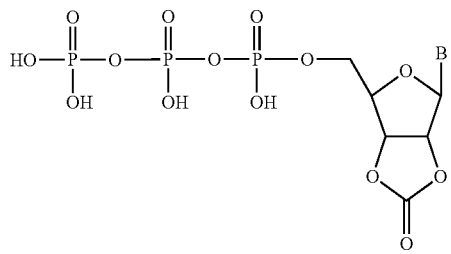

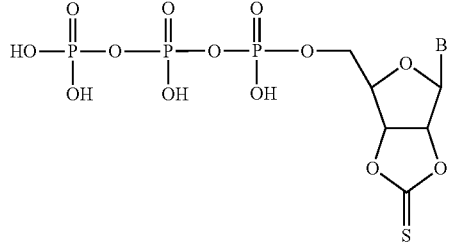

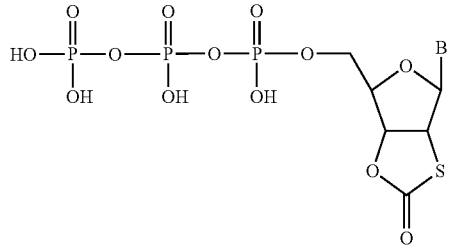

In one embodiment of Formula IB, n is 0 such that $Z^4$, $Z^5$, $Z^6$, $Z^7$, $Z^8$, $Z^9$ and $P^2$ and $P^3$ are not present; and $Z^3$ is a 3'-O-oligonucleotidyl residue or an oligonucleotide primer, thereby providing a "terminated primer."

In one aspect, the methods and compositions herein provide for 3'-substituted NTPs for nucleic acid replication. In some embodiments, the 3'-substituted NTP may have no other modification groups at any position. In other embodiments, the 3'-substituted NTP contain additional modifications such as modifications at the base, triphosphate chain, sugar, or combinations thereof. The 3'-substituted NTP may have a chemical formula of Formulas IA-IB described herein. In preferred embodiments, the 3'-substituted NTP is a 3'-substituted dTTP, dCTP, dATP, dGTP, or dUTP.

In another aspect, provided herein are methods of synthesis of 3'-substituted NTPs having a chemical structure as depicted in Formulas IA-IB further described herein. The modification groups, including 3'-substitution groups, can be integrated into a NTP by using existing synthetic or enzymatic methods. The 3'-substituted NTP of the methods and compositions provided herein may be synthesized by any methods well-known in the art. A comprehensive overviews of a variety of methods for the synthesis of modified and unmodified NTPs have been published (Burgess, K. and Cook. D. 100 Chem. Rev., 2047-2059 (2000); "Nucleoside Triphosphates and Their Analogs: Chemistry, Biotechnology and Biological Applications, Vaghefi, M. ed., Taylor and Francis. Boca Raton (2005). Following synthesis and purification of a 3'-substituted NTP, several different procedures may be utilized to determine the acceptability of the NTP in terms of structure and purity. Examples of such procedures are Nuclear Magnetic Resonance Spectroscopy, Mass Spectrometry. Fluorescent Spectroscopy, Ultra Violet Spectroscopy, High Performance Liquid Chromatography. These procedures are well known to those skilled in the art. Current methods employed for separation, purification and analysis in the art are applicable to the 3'-substituted NTPs of the methods and compositions provided herein as well.

Any 3'-substitution group that accomplishes the purposes of the methods and compositions provided herein may be utilized. The 3'-substitution group should be one that dissociates, is removable, or otherwise converts to an open hydroxyl group under conditions of a replication reaction in which the 3'-substituted NTP is to be employed. On the other hand, the 3'-substitution group should not dissociate or convert to an open 3'-OH group too quickly at ambient temperature. The loss of the 3'-substitution group should be controllable by the user to achieve the benefits of the methods and compositions provided herein. The type and extent of substitution at the 3'-position of the NTP is generally determined empirically with the goal of achieving the above parameters for control of dissociation of the 3'-substitution group of the NTP or terminated primer. In some embodiments, conversion from a 3'-substitution group to an open 3'-OH group is partial (e.g., when the 3'-substitution group dissociates from a fraction of modified (e.g., 3'-substituted) molecules), for example, at least 10%; or at least 20%; or at least 30%; or at least 40%; or at least 50%; or at least 60%; or at least 70%; or at least 80%; or at least 90%; or at least 95; or at least 98%; or at least 99% of modified NTPs (e.g., NTPs with a 3'-substitution group) convert to unmodified NTPs (e.g., NTPs with a 3'-OH). In some embodiments, conversion of a 3'-substitution group occurs at temperatures between about 0-105° C.; or between about 0-100° C.; or between about 20-100° C.; or between about 37-100° C.; or between about 50-100° C.; or between about 70-100° C.; or about 45° C.; or about 50° C.; or about 55° C.; or about 60° C.; or about 65° C.; or about 70° C.; or about 75° C.; or about 80° C.; or about 90° C.; or about 95° C.; or about 96° C.; or about 97° C.; or about 98° C.; or about 99° C.; or about 100° C. In some embodiments, two different types of 3'-substituted NTPs are used and the two different types of 3'-substituted NTPs can either convert at about the same temperature or at different temperatures. In a preferred embodiment, a first 3'-substituted NTP converts at the initial denaturation temperature for a PCR reaction (~95° C.) and a second 3'-substituted NTP converts at the initial denaturation temperature for a reverse transcriptase reaction (~50° C.). The ability to select 3'-substitution groups based on their conversion properties allows a user to combine reagents for different replication reactions in the same reaction vessel (e.g., the user would only need to prepare a single premix for two different reactions instead of the standard practice of preparing one premix for each reaction). Accordingly, various combinations of replication reactions can be performed in a single reaction vessel by utilizing 3-substituted NTPs selective for each different replication reaction.

In another embodiment, the 3'-substituted NTPs of the methods and compositions provided herein may contain chiral atoms in 3'-substitution group or in any other part of the NTP molecule including modification group or groups. The chirally may lead to individual diastereomers of 3'-substituted NTPs or to a mixture of the diastereomers. The 3'-substituted NTP can be racemic or diastereomeric mixture, or 70%, or 80%, or 90%, or 95%, or 99%, or 100% chirally pure compound.

In some replication reactions, not all NTP molecules in the replication reaction will contain a 3'-substitution group. Preferably, even a mixture of both inactive/terminating state or 3'-substituted NTPs and active 3'-unsubstituted NTP improves efficacy and specificity of replication in a mixed population, as compared to not using 3'-substituted NTPs at all. Preferably, prior to incubation at an initial denaturation temperature, 3'-substituted NTPs make up at least 25% of total NTP molecules, preferably at least 50% of total NTP molecules, preferably at least 75% of total NTP molecules and preferably at least 90% of total NTP molecules, preferably at least 95% of total NTP molecules, preferably at least 98% of total NTP molecules, more preferably at least 99% of total NTP molecules, and more preferably 100% of total NTP molecules. In another embodiment, two, three, four or all types of NTPs may be 3'-substituted NTPs.

In one embodiment, only one type of NTP in the replication reaction is 3'-substituted while all other types of NTPs are regular NTP molecules. For example, where dATPs, dTTPs, dGTPs, and dCTPs are the types of NTPs in an replication reaction, only dATPs are 3'-substituted and the dTTPs, dGTPs, and dCTPs are regular NTP molecules. In another embodiment, two or more types of NTPs are 3'-substituted. In another embodiment, three or more types of NTPs are 3'-substituted. In another embodiment, four or more types of NTPs are 3'-substituted.

In another embodiment, more than one type of a 3'-substituted NTP may be present in a replication reaction. A mixture of 3'-substituted NTPs may be used in a replication reaction. In one embodiment, a mixture of non-substrate NTPs and terminating NTPs may be present in the same replication reaction. In another embodiment, a mixture of 3'-substituted NTPs with different substitution groups may be present in the same replication reaction.

In one aspect, the methods and compositions provided herein provide a chemically modified nucleoside with a 3'-substitution group that is removable, or convertible to an open 3'-hydroxyl group by heat. Such modified nucleoside can be converted to the corresponding NTP by methods which are compatible with current synthesis methods. The corresponding 3'-substituted NTP of any nucleoside can be prepared. In contrast, glyoxyl modification (Bonner, et al., U.S. Patent App. No. 20030162199) which also represents a thermolabile group (but is not a 3'-substitution group), can only be added to the heterocyclic base of guanine containing NTP. Therefore the thermolabile glyoxyl modification is restricted to one kind of NTP, while in the methods and compositions provided herein, any or all NTPs can have a thermolabile 3'-substitution group.

In yet another aspect, provided herein is a method of template dependent synthesis of nucleic acids using 3'-substituted NTPs, as described herein.

Thermus aquaticus (Taq) DNA polymerase, a thermostable polymerase, as well as other DNA or RNA polymerases including DNA dependent DNA polymerases, RNA dependent DNA polymerases, DNA dependent RNA polymerases and RNA dependent RNA polymerases may be used in conjunction with the methods and compositions provided herein. In some embodiments, a replication reaction includes a nucleic acid polymerase and one or more additional enzymes including a second nucleic acid polymerase, ligases (e.g., DNA ligases, RNA ligases), synthetases, nucleases (e.g., nucleic acid restriction enzymes, homing endonucleases, nicking endonucleases), DNA repair proteins, methytransferases, kinases, phosphatases, sulfurylases, recombinases, reverse transcriptases, helicases and other enzymes known in the art.

One aspect of the methods and compositions provided herein provide a 3'-substituted non substrate NTP with a 3'-substitution group removable by heat at temperatures that are compatible with replication procedures currently in use or with those that may be developed in future. The presence of 3'-substitution group may impair incorporation of the 3'-substituted NTP by nucleic acid polymerase, or may disrupt the recognition of the 3'-substituted NTP by nucleic acid polymerase or may otherwise prevent polymerase mediated primer extension (FIG. 1A). The oligonucleotide primer will not be extended by nucleic acid polymerase until the replication reaction reaches an optimal hot start temperature to convert the 3'-substitution group of the NTP to 3'-OH group and transform the NTP to the active state. The conversion of the 3'-substituted NTP to its active state preferably coincides with the initial denaturation step of PCR. This "hot start" activation of the nucleic acid replication reaction significantly decreases a formation of unwanted replication products through preventing primer extension a low temperatures.

Another aspect of the methods and compositions provided herein provide a 3'-substituted terminating NTP with a 3'-substitution group removable or convertible to an open hydroxyl group by heat at temperatures compatible with the replication procedures that are currently in use or with those that may be developed in the future. The 3'-substituted terminating NTP is incorporated onto the 3'-end of the primer by a nucleic acid polymerase to generate a terminated primer. The terminated primer is in a terminating state and is not extendable by nucleic acid polymerase, thereby preventing unwanted replication products from being formed. When the replication reaction reaches an optimal high stringency hot start temperature, the 3'-substitution group is removed or converted to open 3'-OH group, resulting in the conversion of the terminated primer to an extendable primer which is compatible with nucleic acid replication and can be further elongated (FIG. 1B).

In addition to being stable at room temperature in buffer solution, the 3'-substituted NTPs, as disclosed herein are preferably stable during conditions for NTP synthesis, separation and purification processes such as chromatography, precipitation, long-term storage, and preparation of replication reaction mixtures.

The methods and compositions provided herein will now be described in greater detail by reference to the following non-limiting examples.

EXAMPLE 1

Preparation of 3'-substituted 2'-deoxyribonucleosides

Six groups were selected for 3'-substitution of dTTP: tetrahydropyranyl (THP), 4-methoxytetrahydropyranyl (MTHP), tetrahydrofuranyl (THF), acetyl (Ac), methoxyacetyl (CH₃OAc) and phenoxyacetyl (PhOAc).

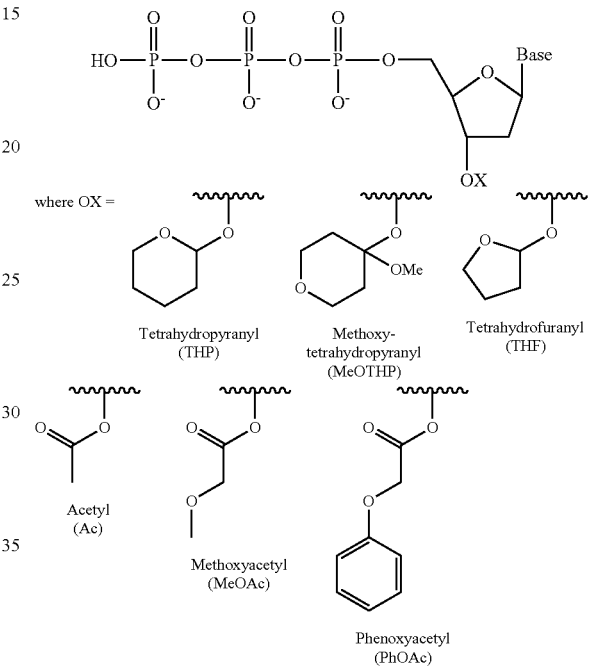

The 3'-ether derivatives of thymidine were synthesized according to general synthetic route as follows. First, thymidine was reacted with 1.2 equiv. of acetic anhydride in pyridine. The resulting mixture of 3'-O-acetyl, 5'-O-acetyl and 3', 5'-O-bis-acetyl substituted thymidines was separated into individual compounds using silica gel chromatography. The isolated 5'-O-acetylthymidine was reacted with 2,3-dihydrofuran, 3,4-dihydro-2H-pyran or 5,6-dihydro-4-methoxy-2H-pyran in the presence of p-toluenesulfonic acid in dioxane for 5 hours. Subsequent treatment with methanolic ammonia to remove 5'-O-acetyl protecting group produced 3'-THF, 3'-THP or 3'-MTHP derivatives of thymidine, respectively. The 3'-THF substituted deoxyribonucleosides dA and dC were prepared starting from N-benzoyl-2'-deoxyadenosine and N-benzoyl-2'-deoxycytidine using an approach similar to the synthesis of 3'-THF-dT, where required protection of the 5'-position was achieved by reaction of the above nucleosides with benzoyl chloride in pyridine. The 3'-THF-2'-deoxyguanosine was synthesized starting from commercially available 5'-levulinyl N-isobutyryl-2'-deoxyguanosine using the same general synthetic route outline above for synthesis of 3'-THF-dT.

The 3'-O-methoxyacetyl and 3'-O-phenoxyacetyl ester of thymidine were prepared according to another general route as follows. The 5'-DMT-thymidine was treated with methoxyacetyl chloride or phenoxyacetic anhydride in pyridine, followed by acid removal of DMT group to form the corresponding 3'-ester derivative of thymidine. 3'-O-acetylthymidine was isolated by silica gel chromatography as specified above.

Overall, the 3'-substituted 2'-deoxynucleosides were isolated in 12-60% overall yields.

EXAMPLE 2

5'-triphosphorylation of 3'-substituted 2'-deoxyribonucleosides

The 3'-substituted 2'-deoxynucleoside 5'-triphosphates were prepared from the 3'-ether and 3'-ester substituted 2'-deoxynucleosides according to the Ludwig-Eckstein procedure (J. Org. Chem., 54, 631-635 (1989)) as follows.

The 3'-substituted 2'-deoxynucleoside was reacted with 1.1 equiv. of 2-chloro-4H-1,3,2-benzodioxaphosphorin-4-one in dioxane-pyridine solution followed by reaction with 1.6 equiv. of tributylammonium pyrophosphate, subsequent iodine oxidation of P(III) to P(V), and a final treatment with aqueous triethylammonium bicarbonate. The resulting 3'-substituted dNTPs were isolated and purified by a combination of anion-exchange and reverse-phase chromatography to obtain 98-99% pure 3'-substituted dNTP as either sodium or potassium salt. Structures of synthesized compounds were confirmed by proton and phosphorus NMR and mass-spectrometry.

EXAMPLE 3

Figure 3:
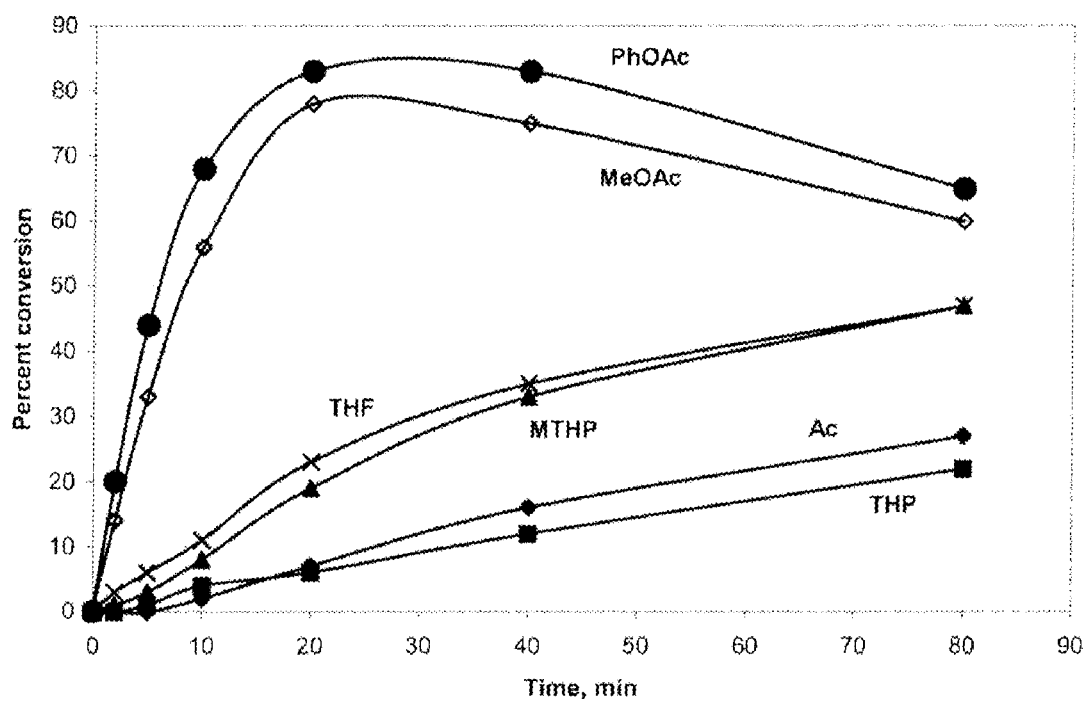
FIG. 3 shows the kinetics of formation of dTTP from 3'-substituted dTTPs in PCR buffer at 95° C.

Kinetics of Conversion of dTTP Containing a 3'-substituted Group to the Corresponding Natural dTTP Conversion of the 3'-substituted dTTP to the corresponding unmodified dTTP was investigated in PCR buffer (pH 8.4 at 25° C., Table 1) at 20° C. and 95° C. The reactions were monitored by analysis of the incubated mixtures by reverse-phase and anion-exchange HPLC. The resultant formation of dTTP versus time at 95° C. is presented in FIG. 3. The estimated concentration of the dTTP that formed from 3'-substituted dTTP after 2, 10, and 20 minutes of incubation at 95° C. are presented in Table 1.

At room temperature (ca. 20° C.) in PCR buffer, all 3'-ether substituted dTTP were stable for at least several days. Among the 3'-ester derivatives of dTTP the 3'-O[CH₃OAc] and 3'-O [PhOAc] derivatives of d TP showed 4% and 10% cleavage of the 3'-ester group, respectively, within 60 minutes of incubation in PCR buffer at room temnperature, whereas for 3'-O-[Ac] derivative of dTTP only 6% cleavage of the 3'-acetyl group was detected after 24 hours of incubation.

TABLE 1

Estimated concentration of unmodified dTTP forming in 250 μM solution of 3'-substituted dTTP during incubation at 95° C. in PCR buffer (50 mM KCl, 1.5 mM MgCl₂, 20 mM Tris (pH 8.4 at 25° C.)).

| | Concentration of unmodified dTTP, μM | | |
|---|---|---|---|
| 3'-substitution group | 2 min | 10 min | 20 min |
| —O(Ac) | 0 | 5 | 18 |
| —O(THP) | ≦1 | 10 | 16 |
| —O(MTHP) | 2 | 21 | 47 |
| —O(THF) | 7 | 39 | 57 |

TABLE 1-continued

Estimated concentration of unmodified dTTP forming in 250 μM solution of 3'-substituted dTTP during incubation at 95° C. in PCR buffer (50 mM KCl, 1.5 mM MgCl₂, 20 mM Tris (pH 8.4 at 25° C.)).

| | Concentration of unmodified dTTP, μM | | |
|---|---|---|---|
| 3'-substitution group | 2 min | 10 min | 20 min |
| —O(CH₃OAc) | 35 | 140 | 195 |
| —O(PhOAc) | 50 | 170 | 209 |

EXAMPLE 4

Figure 4:
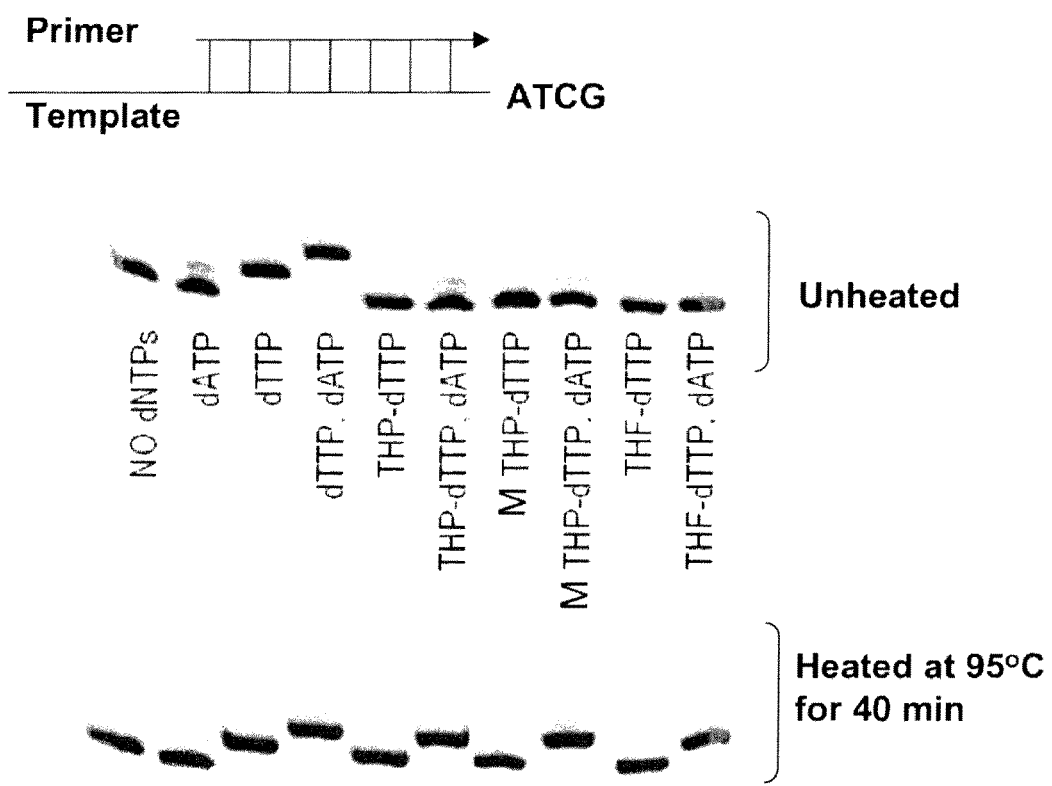
FIG. 4 shows the results of challenged incorporation of 3'-ether substituted dTTP by Klenow DNA polymerase in primer extension experiments with unheated (top) and preheated (bottom) 3'-substituted dTTPs.

Incorporation of the 3'-Substituted dTTPs by Thermus aquaticus (Taq) and Klenow DNA Polymerases in Primer Extension Experiments The ability of Klenow (exo-) DNA polymerase to perform room temperature primer extensions of a pre-annealed primer/template duplex was evaluated in 50 mM NaCl, 10 mM Tris-HCl (pH 7.9), 10 mM MgCl, 1 mM DTT, 0.5 units of enzyme, 0.2 mM dATP and in the presence of one of the following 3'-substituted dTTP derivatives: 3'-THP-dTTP, 3'-MTHP-dTTP or 3'-THF-dTTP (FIG. 4 (top)). In the incorporation and extension experiments, it was found that none of the 3'-substituted derivatives of dTTP (3'-THP-dTTP, 3'-MTHP-dTTP, and 3'-THF-dTTP) were incorporated into the primer (consistent with "no dTTP" negative control). These findings that 3'-substituted dTTP derivatives were not substrates for Klenow (exo-) DNA polymerase are consistent with the proposed mechanism of FIG. 1A. As an added control, we found that after a 40 minute preheating step at 95° C., all of the above 3'-substituted dTTP analogs became substrates for enzyme and behaved in a similar fashion to unmodified dTTP (FIG. 4 (bottom)). This confirms that a preheating step does convert 3'-substituted dTTP into dTTP suitable for incorporation and extension reactions.

Time course incorporation extension experiments were performed with 3'-O-acetyl-dTTP, and it was shown that 3'-O-acetyl dTTP is not a substrate for Klenow (exo-) DNA polymerase in agreement with published data (Metzker, et al., 22 Nucleic Acids Res., 4259-4267 (1994)). The 3'-O-methoxyacetyl and 3'-O-phenoxyacetyl derivatives of dTTP were not tested because the kinetic experiments (Example 3) showed these 3'-substitution groups would not be stable during extension reaction.

The extension experiments were repeated with Taq DNA polymerase at room temperature utilizing 25 units of enzyme and either 3'-THF-dTTP or 3'-Ac-dTTP. The results were similar to that obtained using Klenow (exo-) DNA polmerase, as both 3'-substituted dTTP derivatives were not substrates for Taq DNA polymerase.

The performance of 3'-THF-dCTP in primer extension experiments was also evaluated. The results generated for this analog were similar to that of 3'-THF-dTTP, suggesting that the 3'-substituted DATP and dGTP derivatives are not suitable substrates for Klenow (exo-) or Taq DNA polymerase.

EXAMPLE 5

Formation of Non-specific Amplification Products in the Absence of DNA Template During PCR in the Presence of 3'-substituted dTTPs To explore the effect of 3'-substituted NTPs on PCR performance, experiments were performed using PCR conditions that favor formation of non-specific amplification products, in the absence of template. Oligonucleotide primers targeted to the either a 365 bp fragment of the HIV-1 that gene or to a 1.9 kb fragment of Lambda DNA were employed (Table 2). Both systems are known to yield high levels of non-specific amplification products, including primer dimers, during PCR. The amplification reactions were performed in the absence of template. Each PCR mixture (50 μL) contained both forward and reverse HIV-1 primers (0.5 μM each), dATP, dCTP, and dGTP (200 μM each), Taq polymerase (0.5 units), 1× PCR buffer (see caption to Table 1) and Human genomic DNA (50 ng). Different 3'-derivatives of dTTP were added at 200 μM final concentration to each reaction. PCR cycling parameters included an initial step of 95° C. for 2 min; followed by 40 cycles of [95° C. for 40 sec; 56° C. for 30 sec; 72° C. for 2 min]; followed by 72° C. for 7 min. Non-specific amplification products, including primer dimers, were detected by agarose gel electrophoresis as ~50 base pair fragments in the HIV DNA system and ~500 base pair fragments in the Lambda DNA system (FIGS. 5 (lanes 5 and 6) and 6 (lanes 6-9)).

Figure 5:
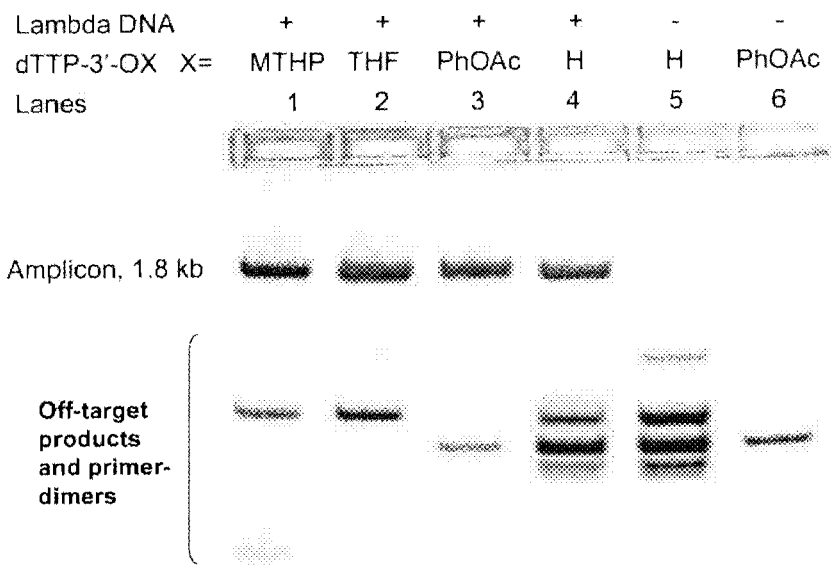
FIG. 5 shows the results of a Hot Start PCR experiment with several 3'-substituted dTTP derivatives in an Lambda system: gel electrophoresis analysis (top) and graphic representation of ratios of amplicon to off-target products (bottom).
Figure 5:
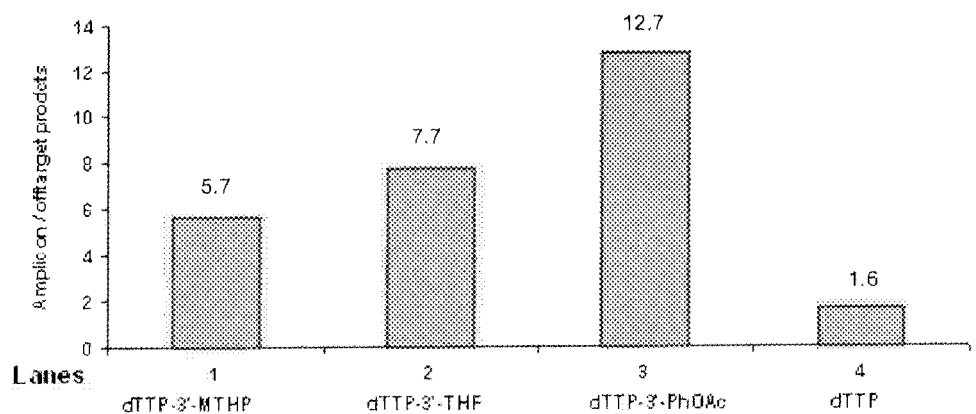
Figure 6:
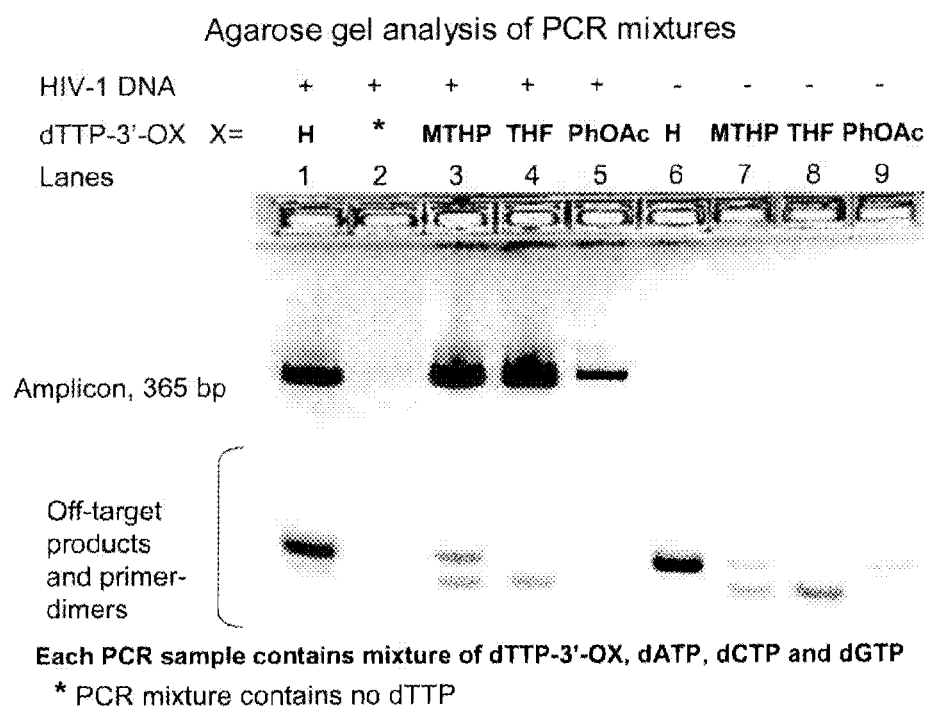
FIG. 6 shows the results of a Hot Start PCR experiment with several 3'-substituted dTTP derivatives in an HIV DNA system: gel electrophoresis analysis (top) and graphic representation of ratios of amplicon to off-target products (bottom).
Figure 6:
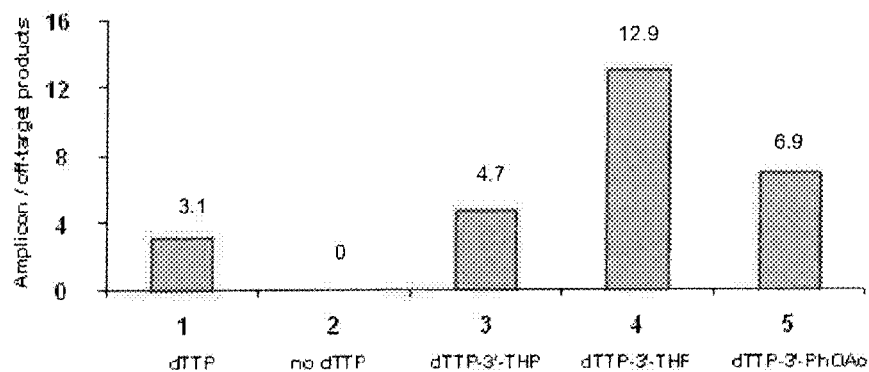

The 3'-substituted dTTP derivatives (acetyl, phenoxyacetyl, tetrahydropyranyl, methoxytetrahydropyranyl and tetrahydrofuranyl) were investigated in the amplification system described above. Overall, analysis of agarose gel electrophoresis data (FIGS. 5 and 6) revealed that in the absence of template, the level of non-specific amplification products in PCR was diminished several fold when 3'-substituted dTTPs were used in place of natural dTTP. The 3'-substituted dTTPs diminished the accumulation of non-specific amplification products including primer dimers.

natural dNTPs were used (compare lanes 4 and 1-3 in FIG. 5 and lanes 1 and 3-5 in FIG. 6). In both the Lambda and HIV-1 template systems, analyses showed not only a decrease in the amount of non-specific amplification products, including primer dimers, but also showed a corresponding increase in amplicon formation. With 3'-THF and 3'-PhOAc-derivatives of dTTP a 3-8 fold improvement resulted in the ratio of amplicon to non specific products, including primer dimers (FIGS. 5 and 6) as compared to dTTP, while with 3'-THP and 3'-Ac derivatives of dTTP, the overall PCR performance was not as good as with natural dTTP (not shown).

Figure 7:
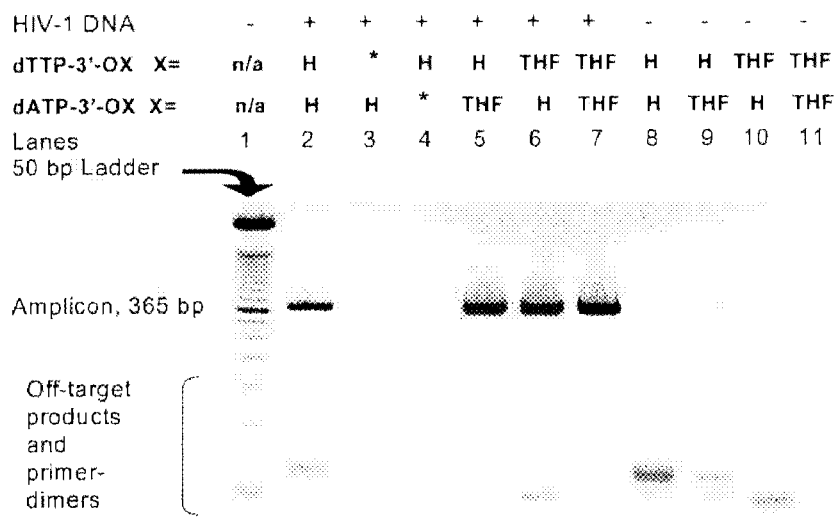
FIG. 7 shows the combined effect of 3'-THF substituted dTTP and dATP on the efficiency of Hot Start PCR amplification of a 365 bp HIV-1 fragment: gel electrophoresis analysis (top) and graphic representation of ratios of amplicon to off-target products (bottom).
Figure 7:
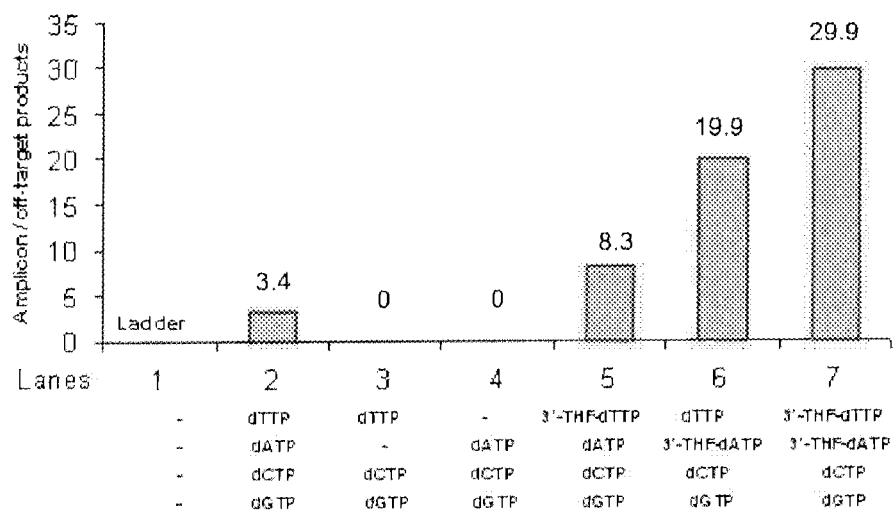

All permutations of substitution of one, two, three or four 3'-THF-dNTPs (from the group of 3'-THF-dATP, 3'-dGTP, 3'-THF-dCTP and 3'-THF-dTTP) were examined for their natural counterpart and the resultant effect on reducing primer dimer formation. In general, any single substitution of 3'-THF dNTP for its natural dNTP was found to improve the PCR performance. Thus, for 3'-THF-dATP derivative, a strong reduction of both non-specific amplification products and an increase of specific amplicon formation was observed (FIG. 7). A combined substitution of two or more 3'-THF derivatives of dNTPs for natural dNTPs further improved PCR performance. Thus, combination of 3'-THF-dTTP and 3'-THF-dATP, as a replacement for dTTP and dATP, nearly completely eliminated non-specific amplification products in the HIV-1 system (approximately 10-fold improvement, FIG. 7). Overall, there was a strong correlation between using more than one type of 3'-substituted dNTP in a PCR mixture with an efficiency and specificity of amplicon production.

TABLE 2

Primer/template PCR systems investigated

| System | Forward primer (5'-3') | Reverse primer (5'-3') | Amplicon length |
|---|---|---|---|
| HIV-1 | GAATTGGGTGTCAACATAGCAGAAT (SEQ ID NO: 1) | AATACTATGGTCCACACAACTATTGCT (SEQ ID NO: 3) | 365 bp |
| Lambda DNA | AAGGAGCTGGCTGACATTTTCG (SEQ ID NO: 2) | CGGGATATCGACATTTCTGCACC (SEQ ID NO: 4) | 1.9 kb |

EXAMPLE 6

Formation of Non-specific Amplification Products in the Presence of DNA Template During PCR in the Presence of 3'-substituted dNTPs For the Lambda DNA and HIV-1 DNA systems (Table 2), PCR conditions were used where non-specific amplification products, including primer dimers, readily formed in the presence of template. These conditions employed 1 μM concentration of both the forward and reverse oligonucleotide primers, 10 HIV-1 or 10,000 Lambda DNA copies of template, 0.2 mM each of dNTP or 3'-substituted dNTP, and 2.0 mM $MgCl_2$. Each mixture contained 50 ng of Human Genomic DNA. The thermal cycling parameters were as follows: 95° C. for 2 min; 40 cycles of [95° C. for 40 sec; 56° C. for 30 sec; 72° C. for 2 min]; 72° C. for 7 min. The reactions were analyzed by agarose gel electrophoresis (FIGS. 5 and 6).

In all cases, the substitution of one 3'-substituted dTTP derivative for natural dTTP improved the performance of PCR, as compared to a control PCR reaction where all four

EXAMPLE 7

Real-Time "Hot Start" PCR with 3'-substituted dNTPs

The performance of 3'-THF dNTPs in Real-time PCR amplification was examined in the model HIV-1 system in the presence of human genomic DNA as a prototypal experiment for pathogen detection. In particular, the performance of a triply substituted set of dNTPs (3'-THF-dATP, 3'-THF-dCTP, and 3'-THF-dTTP and unmodified dGTP) was compared to a set containing all four unmodified dNTPs. On examination of the sigmoidal amplification plots that reflect amplicon accumulation, it was found that the shape of the curve for the 3'-THF dNTP data set was much sharper than the corresponding curve for the unmodified natural dNTP. The curve shape is an indication (Ramakers C, Ruijter J M, Deprez R H, and Moorman A F. 339 Neurosci Lett. 62-6 (2003)) that the efficiency of the PCR amplification is better in the presence of the 3'-THF dNTPs compared to the natural dNTPs. Furthermore, it was found that a good correlation existed between the input number of copies of template and the Ct value (an indication that reliable data can be generated using 3'-substituted dNTPs in Real-time experiments).

EXAMPLE 8

"Hot Start" Activation Approaches Applied to SNP Detection Assays

Identification of genetic polymorphisms that correlate to disease susceptibility and/or to drug effectiveness will aid in the development of diagnostics and therapeutics. Many approaches for single nucleotide polymorphism (SNP) discovery and genotyping have been developed (see, for example, Cozza, A., et al., BMC Genomics, 2007. 8: p. 10; Kwok, P. Y., Annu Rev Genomics Hum Genet, 2001. 2: p. 235-58). Some commercialized approaches to SNP discovery include multiplexing capable platforms, such as the Third Wave Invader-Cleavase (Allawi, H. T., et al., J Clin Microbiol, 2006. 44(9), p. 3443-7); Luminex suspension Beads array (Dunbar, S. A., Clin Chim Acta, 2006. 363(1-2), p. 71-82); Biotage Pyrosequencing (Langace T., et al., Mutat Res, 2005. 573(1-2), p. 96-102); Applied Biosystems Taq-Man and SNPlex genotyping (De la Vega, F. M., et al., Mutat Res, 2005. 573(1-2), p. 111-35); and Roche Cobas Allele Specific PCR and template-directed single base extension methods (Chen, X., et al., Genome Res, 1999. 9(5), p. 492-8). There are several high throughput platforms including the Illumina BeadArray-GoldenGate genotyping assay (Shen, R. et al., Mutat Res, 2005. 573(1-2), p. 70-82); ParAllele Molecular Inversion Probe Assay on Affymetrix GeneChip arrays (Matsuzakil, H., et al., Genome Res, 2004. 14(3), p. 414-25); and Perlegen genotyping on high density arrays (Easton, D. F., et al., Nature, 2007. 447(7148), p. 1087-93), each of which is capable of genotyping multiple SNP sites simultaneously.

One of the major challenges of detecting SNPs is the difficulty in developing a robust means to differentiate between a wild-type sequence and the corresponding sequence containing a point mutation. Many successful approaches involve the use of multiple enzymes in a series of sequential reactions, where each successive step further improves the specificity of detection. One of the most notable disadvantages of current multi-enzyme SNP detection protocols is the necessity to open test tubes at intermediate stages of the assay to transfer reaction products and/or to add the reagents and reaction components required for the downstream enzymatic steps. Reduction or elimination of the intermediate user intervention steps will a) improve the assay efficiency, b) reduce the time, cost, and c) reduce the probability of technical errors during sample manipulation.

Figure 8:
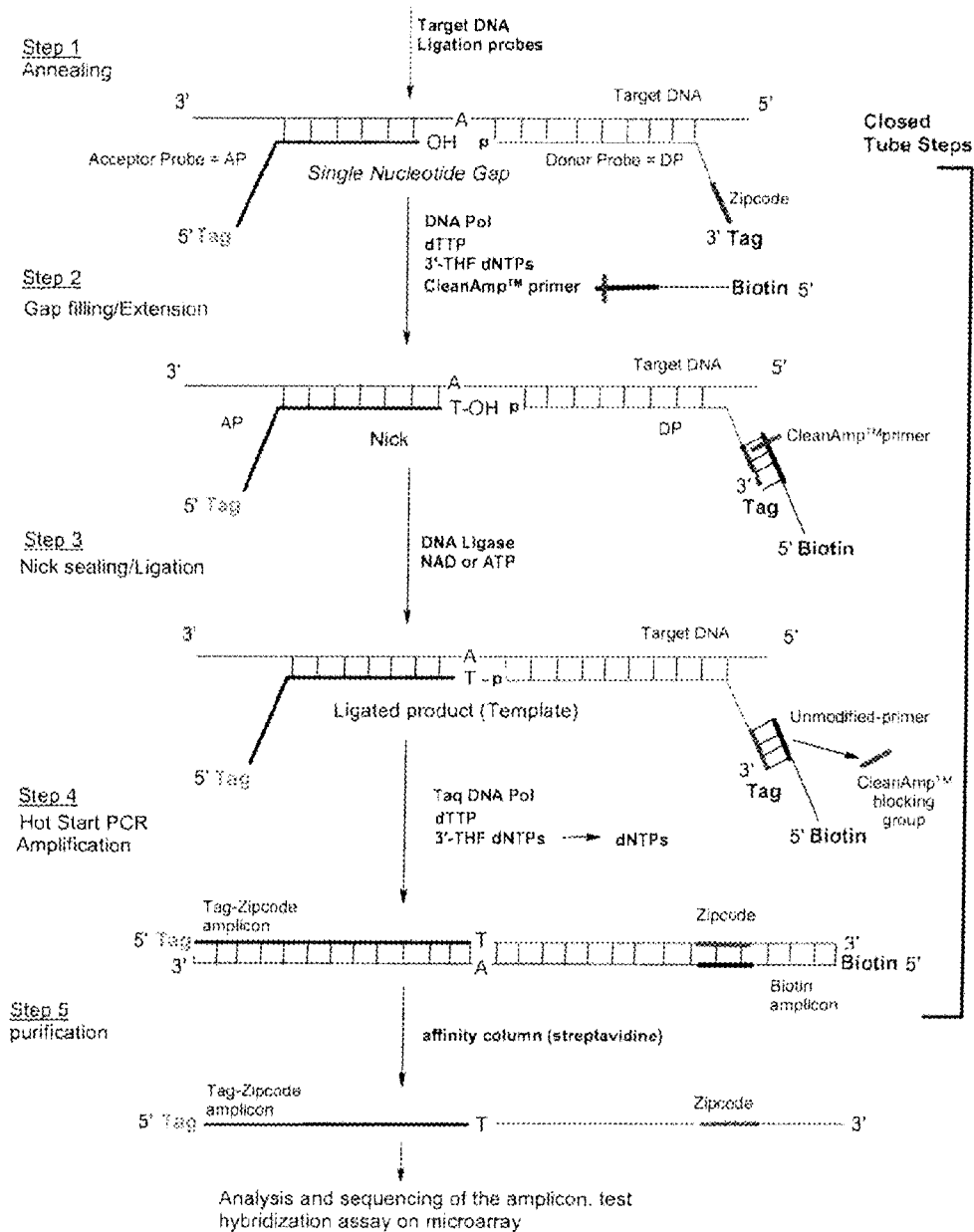
FIG. 8 is a graphic representation of a preferred one-tube Gap EXtension Ligation PCR (GEXL-PCR) approach using 3'-substituted dNTPs in combination with phosphotriester primers.

A scheme of improved closed tube format assay for detection of SNPs is presented in FIG. 8. The GEXL-PCR format combines the utility of 3'-substituted dNTPs and thermolabile phosphotriester-modified primers (Zon, G., et al., US Patent Appl. No. 20070281308) with a gap-filling reaction (DNA polymerase), a nick joining (DNA Ligase) and Hot Start PCR amplification. This approach represents a modified version of SNP assays developed by several companies (ParAllele, Illumina, Applied Biosystems). The key feature that allows for a one-tube format is the ability to include all components for a downstream PCR amplification reaction (enzymes, dNTPs and primers) without their interference in the low-temperature gap-filling and ligation steps. In particular, all of the dNTPs except those needed to fill the gap are substituted with 3'-THF dNTPs. Additionally, the biotinylated phosphotriester primer that binds to the Zipcode region (nucleotide sequence complementary to a 3'-terminal sequence of the phosphotriester primer) of the Donor Probe (the ligating oligonucleotide containing 5'-phosphate group) is blocked from extension using thermolabile phosphotriester primer modification. By performing the gap filling/extension (Step 2) and nick sealing/ligation steps (Step 3) at lower temperatures (0-20° C.), the probability of undesired occurrences such as loss of 3'-substitution group from 3'-substituted dNTPs with a possibility of incorrect dNTP gap-incorporation, with subsequent ligation, or uncontrollable extension of the biotinylated primer is greatly diminished. Upon a thermal activation step (Step 4), the 3'-THF group of 3'-substituted dNTPs and the primer phosphotriester protecting group are removed, allowing for PCR amplification to start and proceed. Overall, the use of substituted components (3'-substituted dNTPs and phosphotriester primers) allows for a more streamlined approach to preparing material for SNP analysis by eliminating the need for a manipulation step between Steps 2 and 4.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

What is claimed is:

1. A method of replicating nucleic acids, said method comprising: replicating nucleic acid, wherein at least one NTP added to a replication reaction mixture comprises a thermally labile 3'-substitution group and wherein said replication reaction mixture does not contain chemical reagents for removal of said thermally labile 3'-substitution group.

2. The method of claim 1, wherein the 3'-substituted NTP does not support, impairs or prevents nucleic acid polymerase extension in the reaction.

3. The method of claim 1, wherein the at least one 3'-substituted NTP is a nonsubstrate NTP.

4. The method of claim 1, wherein the at least one 3'-substituted NTP is a terminating NTP.

5. The method of claim 1, wherein the at least one 3'-substituted NTP incorporates into an oligonucleotide primer resulting in a terminated primer.

6. The method of claim 1, wherein the 3'-substitution group converts to an open 3'-hydroxyl group during the nucleic acid replication.

7. The method of claim 1, wherein the 3'-substitution group converts to an open 3'-hydroxyl group during the initial denaturation step of the nucleic acid replication.

8. The method of claim 6, wherein conversion is partial.

9. The method of claim 6, wherein conversion is complete.

10. The method of claim 1, wherein said conversion occurs at a temperature sufficient to dissociate the 3'-substitution group to form an open 3'-hydroxyl group.

11. The method of claim 1, wherein said 3'-substitution group converts to an open 3'-hydroxyl group at a temperature between about 37° C.-100° C.

12. The method of claim 1, wherein said 3'-substitution group converts to an open 3'-hydroxyl group at a temperature between about 70° C.-100° C. or at about 50° C.

13. The method of claim 1, wherein $t^{1/2}$ of conversion of said 3'-substitution group to an open 3'-hydroxyl group is between about 1-120 minutes at about 95° C. or at about 50° C.

14. The method of claim 1, wherein the amplification reaction comprises 3'-substituted NTPs with two or more different 3'-substitution groups.

15. The method of claim 14, wherein the different 3'-substitution groups convert to open 3'-hydroxyl groups at different temperatures.

16. The method of claim 15, wherein a first 3'-substitution group converts to an open 3'-hydroxyl group at about 50° C. and a second 3'-substitution group converts at about 95° C.

17. The method of claim 1, wherein nucleic acid replication is polymerase chain reaction (PCR), Allele-specific PCR, Assembly PCR or Polymerase Cycling Assembly (PCA), Asymmetric PCR, Colony PCR, Emulsion PCR, Fast PCR, Gap Extension Ligation PCR (GEXL-PCR), Gap Ligation Chain Reaction (Gap LCR), Helicase-dependent amplification, Hot-start PCR, Intersequence-specific (ISSR) PCR, Inverse PCR, Ligation-mediated PCR, Linear-After-The-Exponential-PCR (LATE-PCR), Methylation-specific PCR (MSP), Multiplex Ligation-dependent Probe Amplification, (MLPA), Multiplex-PCR, Nested PCR, Overlap-extension PCR, PAN-AC, Quantitative PCR (Q-PCR), Quantitative real-time PCR (QRT-PCR), Real-Time PCR, Reverse Transcription (RT), Rapid Amplification of cDNA Ends (RACE PCR), Single molecule amplification PCR (SMA PCR), Thermal asymmetric interlaced PCR (TAIL-PCR), Touchdown PCR, long PCR, nucleic acid ligation, DNA sequencing or reverse transcription-PCR (RT-PCR).

18. The method of claim 1, wherein nucleic acid replication reaction comprises one or more enzymes selected from the group consisting of DNA dependent DNA polymerases, RNA dependent DNA polymerases, DNA dependent RNA polymerases, RNA dependent RNA polymerases, DNA ligases, RNA ligases, synthetases, nucleases, and restrictases.

19. The method of claim 1, wherein said nucleic acid is DNA, RNA, LNA, PNA or a combination thereof.

20. The method of claim 1, wherein said NTPs are one or more 3'-substituted NTPs selected from the group consisting of 3'-substituted dATP, 3'-substituted dTTP, 3'-substituted dGTP, 3'-substituted dCTP, and 3'-substituted dUTP.

21. The method of claim 1, wherein said 3-substituted NTPs comprise 3'-substituted dATP, 3'-substituted dTTP, 3'-substituted dGTP, and 3'-substituted dCTP.

22. The method of claim 1, wherein said 3'-substituted NTPs comprise 3'-substituted dATP, 3'-substituted dUTP, 3'-substituted dGTP, and 3'-substituted dCTP.

23. The method of claim 1, wherein said 3'-substituted NTPs comprise 25% or less of total NTPs in the replication reaction.

24. The method of claim 1 wherein said 3'-substituted NTPs comprise 25% to 100% of total NTPs in the replication reaction.

25. The method of claim 1, further comprising one or more modification groups on a sugar or phosphate group of said 3'-substituted NTPs.

26. The method of claim 1, wherein said 3'-substituted NTP further comprises a detectable label.

27. The method of claim 1, wherein the 3'-substituted NTPs are a chirally pure, racemic or diastereomeric mixture.

28. The method of claim 1, wherein the presence of the 3'-substituted NTPs in a replication reaction reduces formation and subsequent replication of nonspecific products as compared with replication using a corresponding unsubstituted NTP.

29. The method of claim 1, wherein the 3'-substitution group is selected from the group consisting of O-phenoxyacetyl; O-methoxyacetyl; O-acetyl; O-(p-toluene)sulfonate; O-phosphate; O-nitrate; O-[4-methoxy]-tetrahydrothiopyranyl; O-tetrahydrothiopyranyl; O-[5-methyl]-tetrahydrofuranyl; O-[2-methyl,4-methoxy]-tetrahydropyranyl; O-[5-methyl]-tetrahydropyranyl; and O-tetrahydrothiofuranyl.

30. The method of claim 1, wherein the 3'-substituted NTP and derivatives thereof has the structure of

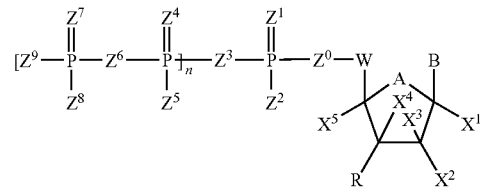

wherein: n is 0 or 1;
B is selected from a substituted or non-substituted purine or pyrimidine, any aza or deaza derivative thereof, or any "universal base" or "degenerate base" of any NTP analog;
A is selected from the group consisting of O, S, Se, $CR^1R^2$, and $NR^1$;
W is selected from the group consisting of O, S, Se, $CR^1R^2$, and $NR^1$;
each $R^1$ and each $R^2$ is independently selected from the group consisting of H, F, Cl, Br, I, $OR^3$, $R^3$, $SeR^3$, $NR^3R^4$, $C(Y)R^5$, and substituted or non-substituted alkyl, alkenyl, alkynyl, aryl, and aralkyl, wherein any substituent may each optionally contain one or more heteroatoms;
each $R^3$ and each $R^4$ is independently selected from the group consisting of H or substituted or non-substituted alkyl, alkenyl, alkynyl, aryl, and aralkyl, wherein any substituent may each optionally contain one or more heteroatoms;
each $R^5$ is selected from the group consisting of H, F, Cl, Br, $OR^3$, $SR^3$, $SeR^3$, $NR^3R^4$, $C(Y)R^3$ and substituted or non-substituted alkyl, alkenyl, alkynyl, aryl, and aralkyl, wherein any substituent may each optionally contain one or more heteroatoms;
each Y is selected from the group consisting of O, S, Se, $CR^1R^2$, and $NR^1$;
$Z^1$, $Z^4$ and $Z^7$ are each independently selected from the group consisting of O, S, Se, $CR^1R^2$, and $NR^1$;
$Z^0$ and $Z^6$ are each independently selected from the group consisting of O, S, Se, $O_2$, $CR^1R^2$, $NR^1$, and $C(Y)$;
$Z^3$ is selected from the group consisting of O, S, Se, $O_2$, $CR^1R^2$, $NR^1$, $C(Y)$, a 3'-O-oligonucleotidyl residue, and an oligonucleotide primer, wherein when n is 0, $Z^3$ is a 3'-O-oligonucleotidyl residue or an oligonucleotide primer, and wherein when n is 1, $Z^3$ is O, S, Se, $O_2$, $CR^1R^2$, $NR^1$, or $C(Y)$;
$Z^2$, $Z^5$, and $Z^8$ are each independently selected from the group consisting of H, F, $OR^3$, $SR^3$, $SeR^3$, $NR^3R^4$, $NR^3OR^3$, $NR^3$—$NR^3R^4$, CN, $N_3$, $(BH_3)^-$ $M^+$, and $C(Y)R^5$;
$Z^9$ is selected from the group consisting of H, F, $OR^3$, $SR^3$, $SeR^3$, $NR^3R^4$, $NR^3OR^3$, $NR^3$—$NR^3R^4$, CN, $N_3$, $(BH_3)^-$ $M^+$, $C(Y)R^5$, and phosphate;
$Z^{10}$ is selected from the group consisting of O, S, and Se;
$M^+$ is a cation;

$X^1$, $X^2$, $X^3$, $X^4$ and $X^5$ are each independently selected from the group consisting of $R^1$, $NR^3OR^3$, $NR^3$—$NR^3R^4$, CN, $N_3$, NO, $NO_2$, NCO, NCS, OCN, SCN, and $SSR^3$; R is selected from the group consisting of

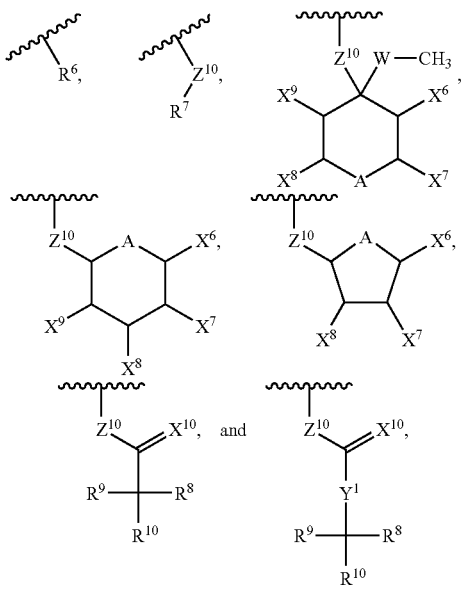

R may be optionally covalently attached through appropriate atoms or group of atoms to $X^1$, $X^2$, $X^3$, $X^4$, $X^5$, $Z^0$, $Z^2$, $Z^3$, $Z^4$, $Z^5$, $Z^6$, $Z^7$, $Z^8$, $Z^9$, A, W, or B portion of the NTP molecule depicted in Formula IA, each $R^6$ is independently selected from the group consisting of inorganic acid residue, or derivative thereof, with the exception of carbonic acid, where the derivatives may include but are not limited to halogen, sulfonate, thio-sulfonate, seleno-sulfate, seleno-sulfonate, sulfate ester, sulfate thioester, sulphite, sulphinate, sulphinic ester, nitrate, nitrite, phosphorus, selenium and boron containing acids;

each $R^7$, each $R^8$, each $R^9$, and each $R^{10}$ is independently selected from the group consisting of hydrogen, and a straight or branched optionally substituted hydrocarbyl group having from 1-20 carbon atoms, wherein the hydrocarbyl is alkyl, alkenyl or alkynyl which may optionally include at least one substituent selected from the group consisting of hydroxyl, alkoxy, amino, amido, cycloalkyl, heterocycloalkyl, aryl, aryloxy, and heteroaryl;

each $X^6$, each $X^7$, each $X^8$, and each $X^9$ is independently selected from any substituted or unsubstituted group consisting of acyl, acyloxy, alkenyl, alkenylaryl, alkenylene, alkyl, lower alkyl, alkylene, alkynyl, alkynylaryl, alkoxy, lower alkoxy, aikylaryl, alkylcarbonylamino, alkylsulfinyl, alkylsulfonyl, alkylsulfonylamino, alkylthio, alkynylene, amido, amidino, amino, arylalkynyl, aralkyl, aroyl, arylalkyl, aryl, arylcarbonylamino, arylene, aryloxy, arylsulfonylamino, carbamate, dithiocarbamate, cycloalkenyl, cycloalkyl, cycloalkylene, guanidinyl, halo, halogen, heteroaryl, heteroarylcarbonylamino, heteroaryloxy, heteroarylsulfonylamino, heterocycle, heterocycle, hydrocarbyl, hydrocarbyl, hydrocarbylcarbonyl, hydrocarbyloxycarbonyl, hydrocarbylcarbonyloxy, hydrocarbylene, organosulfinyl, hydroxyl, organosulfinyl, organosulfonyl, sulfinyl, sulfonyl, sulfonylamino, and sulfuryl;

each $X^{10}$ is independently selected from the group consisting of O, S, Se, $NR^{11}$, N—$OR^{11}$, and $CR^{11}R^{12}$;

each $R^{11}$ and each $R^{12}$ is independently selected from any substituted or unsubstituted group consisting of acyl, acyloxy, alkenyl, alkenylaryl, alkenylene, alkyl, lower alkyl, alkylene, alkynyl, alkynylaryl, alkoxy, lower alkoxy, alkylaryl, alkylcarbonylamino, alkylsulfinyl, alkylsulfonyl, alkylsulfonylamino, alkylthio, alkynylene, amido, amidino, amino, arylalkynyl, aralkyl, aroyl, arylalkyl, aryl, arylcarbonylamino, arylene, aryloxy arylsulfonylamino carbamate, dithiocarbamate, cycloalkenyl, cycloalkyl, cycloalkylene, guanidinyl, halo, halogen, heteroaryl, heteroarylcarbonylamino, heteroaryloxy, heteroarylsulfonylamino, heterocycle, heterocycle, hydrocarbyl, hydrocarbyl, hydrocarbylcarbonyl, hydrocarbyloxycarbonyl, hydrocarbylcarbonyloxy, hydrocarbylene, organosulfinyl, hydroxyl, organosulfinyl, organosulfonyl, sulfinyl, sulfonyl, sulfonylamino, and sulfuryl; and each $Y^1$ is independently selected from the group consisting of O, S, Se, $NR^6$, N—$OR^6$, and $CR^6R^7$.

31. The method of claim 30, wherein $X^1$, $X^3$, and $X^4$ are H; W is $CH_2$; $Z^0$, $Z^1$, $Z^6$ and $Z^7$ are O; and $Z^5$ and $Z^8$ are OH.

32. The method of claim 30, wherein A is NH, O, $CH_2$, or S; $X^1$, $X^2$, $X^3$, $X^4$ and $X^5$ are H: W is $CH_2$; $Z^0$, $Z^1$, $Z^3$, $Z^4$, $Z^6$ and $Z^0$ are O; and $Z^2$, $Z^5$, $Z^8$ and $Z^9$ are OH.

33. The method of claim 30, wherein $X^2$ is H, OH, F, $CH_3$, $OCH_3$, $N_3$, $NH_2$, or $NHCH_3$; A is O; $X^1$, $X^3$, $X^4$ and $X^5$ are H; W is $CH_2$; $Z^0$, $Z^1$, $Z^3$, $Z^4$, $Z^6$ and $Z^7$ are O; $Z^2$, $Z^5$, $Z^8$ and $Z^9$ are OH.

34. The method of claim 30, wherein $X^5$ is H, SH, $CH_3$, F, $OCH_3$, $NH_2$, or $NHCH_3$; A is O; $X^1$, $X^2$, $X^3$ and $X^4$ are H; W is $CH_2$; $Z^0$, $Z^1$, $Z^3$, $Z^4$, $Z^6$, and $Z^7$ are O; and $Z^2$, $Z^5$, $Z^8$ and $Z^9$ are OH.

35. The method of claim 30, wherein $Z^2$ is OH, SH, $BH_3$, $CH_3$, $OCH_3$, or $OCH_2CH_3$; A is O; $X^1$, $X^2$, $X^3$ $X^4$ and $X^5$ are H; W is $CH_2$; $Z^0$, $Z^1$, $Z^3$, $Z^4$, $Z^6$ and $Z^7$ are O; and $Z^5$, $Z^8$ and $Z^9$ are OH.

36. The method of claim 30, wherein $Z^4$ is O or S; n is 1; A is O; $X^1$, $X^2$, $X^3$ $X^4$ and $X^5$ are H, W is $CH_2$; $Z^0$, $Z^1$, $Z^3$, $Z^6$ and $Z^7$ are O; and $Z^2$, $Z^5$, $Z^8$ and $Z^9$ are OH.

37. The method of claim 30, wherein $Z^9$ is SH, $SCH_2CH_2CN$, OH, F, $OCH_3$, $OCH_2CH_3$, OCH , $NHCH_3$, $NH_2$, $NHCH_2CH_2NH_2$, $NHCH_2CH_2CH_2CH_2CH_2CH_2CH_2$ or a phosphate group; n is 1; A is O; $X^1$, $X^2$, $X^3$ $X^4$ and $X^5$ are H; W is $CH_2$; $Z^0$, $Z^1$, $Z^3$, $Z^4$, $Z^6$ and $Z^7$ are O; and $Z^2$, $Z^5$ and $Z^8$ are OH.

38. The method of claim 30, wherein n is 1; A is O; $X^1$, $X^2$, $X^3$ $X^4$ and $X^5$ are H; W is $CH_2$; $Z^0$, $Z^1$, $Z^3$, $Z^4$, $Z^6$ and $Z^7$ are O; and $Z^2$, $Z^5$, $Z^8$ and $Z^9$ are OH.

39. The method of claim 30, wherein B is thymine, cytosine, adenine, guanine, uracil, 5-aminoallyl-uracil, 7-deazaguanine, 7-deaza-7-methylguanine, 7-deaza-7-iodoguanine, 7-deaza-7-aminoallyl-guanine, 7-deaza-8-azaguanine, 7-deazadenine, 2,6-diaminopurine, 5-nitro-cytosine, 5-aminoallyl-cytosine, 5-(Biotin-16)-cytosine, 5-(Fluorescein-11)-cytosine, 4-methylamino-cytosine, 2-thio-5-methyluracil, or 4-thio-5-methyluracil.

40. The method of claim 30, wherein B is recognizable by a nucleic acid polymerase.

41. A kit for nucleic acid amplification comprising one or more 3'-substituted NTPs of claim 1.

42. The kit of claim 41 further comprising one or more selected from the group consisting of instructions for performing a method using said one or more 3'-substituted NTPs to perform said method, container marked for nucleic acid amplification, unmodified dNTPs, modified NTPs, nucleic acid polymerase, magnesium chloride or other divalent cation, and reaction buffer.

43. The kit of claim 42, comprising nucleic acid polymerase and one or more additional enzymes.

44. The method of claim 30, wherein R is:

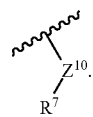

45. The method of claim 44, wherein $Z^{10}$ is O.

46. The method of claim 45, wherein $R^7$ is an optionally substituted alkyl group having 1-6 carbon atoms.

47. The method of claim 46, wherein the alkyl includes an alkoxy substituent.

48. The method of claim 46, wherein the alkyl includes a cycloalkyl substituent.

49. A method for improving specificity of replicating nucleic acids, said method comprising: replicating nucleic acid, wherein at least one NTP added to a replication reaction mixture comprises a thermally labile 3'-substitution group and wherein said replication reaction mixture does not contain chemical reagents for removal of said thermally labile 3'-substitution group.

50. A method for improving efficiency of replicating nucleic acids, said method comprising: replicating nucleic acid, wherein at least one NTP added to a replication reaction mixture comprises a thermally labile 3'-substitution group and wherein said replication reaction mixture does not contain chemical reagents for removal of said thermally labile 3'-substitution group.

51. The method of claim 1, wherein the 3'-substitution group is O-tetrahydrofuranyl, O-tetrahydropyranyl or O-[4-methoxy]-tetrahydropyranyl.

52. The method of claim 1, wherein the 3'-substitution group is O-(1-cyclohexoxy)ethyl, O-(tert-butoxy)ethyl or 2-(iso-butoxy)ethyl.

53. The method of claim 30, wherein R is

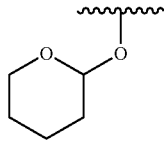

$X^1, x^2, X^3, X^4$ and $X^5$ are H; W is $CH_2$; $Z^0$ through $Z^9$ are O; A is O; and n=1.

54. The method of claim 30, wherein R is

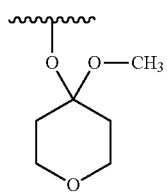

$X^1, X^2, X^3, X^4$ and $X^5$ are H; W is $CH_2$; $Z^0$ through $Z^9$ are O; A is O; and n=1.

55. The method of claim 30, wherein R is

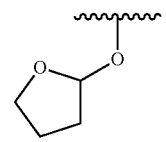

$X^1, X^2, X^3, X^4$ and $X^5$ are H; W is $CH_2$; $Z^0$ through $Z^9$ are O; A is O; and n=1.

56. The method of claim 30, wherein R is

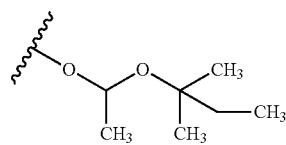

$X^1, X^2, X^3, X^4$ and $X^5$ are H; W is $CH_2$; $Z^0$ through $Z^9$ are O; A is O; and n=1.

57. The method of claim 30, wherein R is

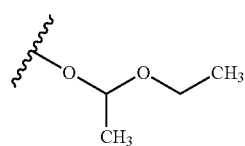

$X^1, X^2, X^3, X^4$ and $X^5$ are H; W is $CH_2$; $Z^0$ through $Z^9$ are O; A is O; and n=1.

58. The method of claim 30, wherein R is

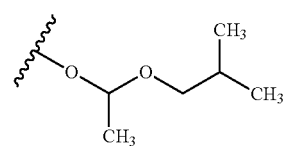

$X^1, X^2, X^3, X^4$ and $X^5$ are H; W is $CH_2$; $Z^0$ through $Z^9$ are O; A is O; and n=1.

59. The method of claim 30, wherein R is

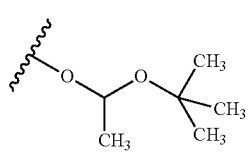

$X^1, X^2, X^3, X^4$ and $X^5$ are H; W is $CH_2$; $Z^0$ through $Z^9$ are O; A is O; and n=1.

60. The method of claim 30, wherein R is

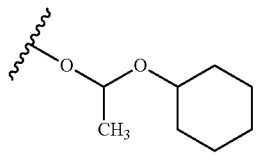

$X^1, X^2, X^3, X^4$ and $X^5$ are H; W is $CH_2$; $Z^0$ through $Z^9$ are O; A is O; and n=1.

61. The method of claim 30, wherein R is

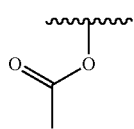

$X^1, X^2, X^3, X^4$ and $X^5$ are H; W is $CH_2$; $Z^0$ through $Z^9$ are O; A is O; and n=1.

62. The method of claim 30, wherein R is

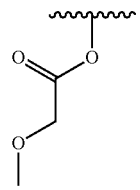

$X^1, X^2, X^3, X^4$ and $X^5$ are H; W is $CH_2$; $Z^0$ through $Z^9$ are O; A is O; and n=1.

63. The method of claim 30, wherein R is

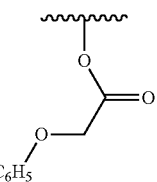

$X^1, X^2, X^3, X^4$ and $X^5$ are H; W is $CH_2$; $Z^0$ through $Z^9$ are O; A is O; and n=1.

* * * * *

UNITED STATES PATENT AND TRADEMARK OFFICE
CERTIFICATE OF CORRECTION

| | | |
|---|---|---|
| PATENT NO. | : 8,133,669 B2 | Page 1 of 1 |
| APPLICATION NO. | : 12/470449 | |
| DATED | : March 13, 2012 | |
| INVENTOR(S) | : Alexandre Lebedev and Inna Koukhareva | |

It is certified that error appears in the above-identified patent and that said Letters Patent is hereby corrected as shown below:

In the Specification:

At Column 1, please replace lines 16-20 with the following:

-- STATEMENT AS TO RIGHTS TO INVENTIONS MADE UNDER FEDERALLY SPONSORED RESEARCH OR DEVELOPMENT

This invention was made with Government support under contract GM079836 awarded by the National Institute for General Medical Science, the National Institutes of Health. The Government has certain rights in this invention. --

Signed and Sealed this
Twenty-fourth Day of June, 2014

Michelle K. Lee
*Deputy Director of the United States Patent and Trademark Office*

SEQUENCE LISTING

<160> NUMBER OF SEQ ID NOS: 4

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gaattgggtg tcaacatagc agaat                                              25

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aaggagctgg ctgacatttt cg                                                 22

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
aatactatgg tccacacaac tattgct                                            27

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cgggatatcg acatttctgc acc                                                23